(12) United States Patent
Hammock et al.

(10) Patent No.: US 9,096,532 B2
(45) Date of Patent: Aug. 4, 2015

(54) PYRAZOLE INHIBITORS OF COX-2 AND SEH

(75) Inventors: Bruce D. Hammock, Davis, CA (US); Sung Hee Hwang, Davis, CA (US); Karen Wagner, Davis, CA (US); Christophe Morisseau, West Sacramento, CA (US); Aaron Wecksler, Davis, CA (US); Guodong Zhang, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/993,317

(22) PCT Filed: Dec. 12, 2011

(86) PCT No.: PCT/US2011/064474
§ 371 (c)(1),
(2), (4) Date: Oct. 21, 2013

(87) PCT Pub. No.: WO2012/082647
PCT Pub. Date: Jun. 21, 2012

(65) Prior Publication Data
US 2014/0038923 A1  Feb. 6, 2014

Related U.S. Application Data

(60) Provisional application No. 61/471,395, filed on Apr. 4, 2011, provisional application No. 61/422,554, filed on Dec. 13, 2010.

(51) Int. Cl.
| | | |
|---|---|---|
| *A61K 31/635* | (2006.01) | |
| *C07D 231/10* | (2006.01) | |
| *C07D 231/12* | (2006.01) | |
| *C07D 231/40* | (2006.01) | |
| *C07D 231/14* | (2006.01) | |

(52) U.S. Cl.
CPC ............ *C07D 231/12* (2013.01); *C07D 231/14* (2013.01); *C07D 231/40* (2013.01)

(58) Field of Classification Search
CPC ............................ C07D 231/10; A61K 31/635
See application file for complete search history.

(56) References Cited

U.S. PATENT DOCUMENTS

| | | |
|---|---|---|
| 6,156,781 A | 12/2000 | Talley et al. |
| 2005/0197338 A1 | 9/2005 | Huang et al. |
| 2005/0209297 A1 | 9/2005 | Sanner et al. |
| 2006/0178347 A1 | 8/2006 | Hammock et al. |
| 2008/0207699 A1 | 8/2008 | Hoelzemann et al. |
| 2009/0227588 A1 | 9/2009 | Fleck et al. |
| 2009/0326039 A1 | 12/2009 | Hammock et al. |

OTHER PUBLICATIONS

Hwang, Sung Hee. Synthesis and Structure—Activity Relationship Studies of Urea-Containing Pyrazoles as Dual Inhibitors of Cyclooxygenase-2 and Soluble Epoxide Hydrolase. Journal of Medicinal Chemistry, 2011, 54, 3037-3050.*
International Search Report and Written Opinion for PCT/US2011/064474, mailed Apr. 10, 2012, 13 pages.

* cited by examiner

*Primary Examiner* — Samantha Shterengarts
(74) *Attorney, Agent, or Firm* — Kilpatrick Townsend and Stockton LLP

(57) ABSTRACT

The present invention provides compounds and compositions, e.g., a series of compounds wherein a 1,5-biarylpyrazole group is conjugated to a urea group by a non-cleavable covalent chain, that are useful as dual COX-2/sEH inhibitors. The compounds disclosed herein have activity associated with the arachidonate cascade. The activity of these compounds was demonstrated using a lipopolysaccharide (LPS) induced model of pain in the rat. The compounds of the present invention demonstrated superior anti-allodynic activity as compared to the same dose of celecoxib, i.e., a COX-2 inhibitor, also as compared to the same dose of t-AUCB, i.e., a sEH inhibitor, and also as compared to the co-administered same dose of both celecoxib and t-AUCB. The dual inhibitors of the present invention demonstrate enhanced in vivo anti-allodynic activity in a nociceptive behavioral assay. In addition, the compounds of the present invention also demonstrated to have potent anti-angiogenic effects toward endothelial cells (HUVEC) and inhibit angiogenesis in vitro, ex vivo and in vivo. The dual inhibitors of the present invention also demonstrate anti-angiogenic effect to slow breast tumor growth in vivo.

23 Claims, 12 Drawing Sheets

Celecoxib

Rofecoxib

Indomethacin t-AUCB

1770 a.

b.

a.

b.

Celecoxib          $ED_{50} = 65 \pm 9 \mu M$

Celecoxib + t-TUCB (1:1)   $ED_{50} = 35 \pm 5 \mu M$

SHH07009B          $ED_{50} = 20 \pm 4 \mu M$

Control  5 µM 21i

Ctrl  2.5 µM 21i

5 µM 21i  10 µM 21i

PYRAZOLE INHIBITORS OF COX-2 AND SEH

CROSS-REFERENCES TO RELATED APPLICATIONS

This application claims priority to U.S. Provisional Application Nos. 61/422,554, filed Dec. 13, 2010, and 61/471,395, filed Apr. 4, 2011, which are incorporated in its/their entirety herein for all purposes.

BACKGROUND OF THE INVENTION

The arachidonic acid (AA) cascade is the target of many pharmaceuticals that are therapies for various conditions such as cardiovascular and inflammatory diseases. For example, nonsteroidal anti-inflammatory drugs (NSAIDs) and selective cyclooxygenase-2 (COX-2) inhibitors block the conversion of AA to prostaglandins (PGs). Also, lipoxygenase (LOX) inhibitors, especially 5-LOX inhibitors, block the conversion of AA to leukotrienes (LTs). Several dual inhibitors that inhibit cyclooxygenase, e.g., COX-1, COX-2, or both COX isozymes, and 5-lipoxygenase are reported as potential agents for the treatment of inflammation (See Kirchner, T.; et al., Evaluation of the Antiinflammatory Activity of a Dual Cyclooxygenase-2 Selective/5-Lipoxygenase Inhibitor, RWJ 63556, in a Canine Model of Inflammation. *J. Pharmacol. Exp. Ther.* 1997, 282, 1094-1101), pain (See Praveen Rao, P. N.; et al., Synthesis and Structure-Activity Relationship Studies of 1,3-Diarylprop-2-yn-1-ones: Dual Inhibitors of Cyclooxygenases and Lipoxygenases. *J. Med. Chem.* 2006, 49, 1668-1683), and cancers (See (a) Barbey, S.; et al., Synthesis and Activity of a New Methoxytetrahydropyran Derivative as Dual Cyclooxygenase-2/5-Lipoxygenase Inhibitor. *Bioorg. Med. Chem. Lett.* 2002, 12, 779-782; and (b) Pommery, N.; et al., New COX-2/5-LOX Inhibitors: Apoptosis-Inducing Agents Potentially Useful in Prostate Cancer Chemotherapy. J. Med. Chem. 2004, 47, 6195-6206). However, there is a third major metabolic pathway involving cytochrome P450 metabolism in this same cascade, which metabolizes AA to epoxyeicosatrienoic acids (EETs). The soluble epoxide hydrolase (sEH) enzyme catalyzes the conversion of epoxyeicosatrienoic acids (EETs), which are cytochrome P450-mediated epoxides of arachidonic acid, into the corresponding dihydroxyeicosatrienoic acids (DHETs). EETs are known to exhibit vasodilatory, cardioprotective, anti-inflammatory, and anti-hyperalgesic effects while the DHETs are largely inactive (See (a) Spector, A. A.; Norris, A. W. Action of epoxyeicosatrienoic acids on cellular function. *Am. J. Physiol. Cell Physiol.* 2007, 292, C996-C1012; (b) Chaudhary, K. R.; et al., Inhibition of Soluble Epoxide Hydrolase by trans-4-[4-(3-adamantan-1-yl-ureido)-cyclohexyloxy]-benzoic acid Is Protective Against Ischemia-Reperfusion Injury. *J. Cardiovasc. Pharmacol.* 2010, 55, 67-73; (c) Li, N.; et al. Beneficial effects of soluble epoxide hydrolase inhibitors in myocardial infarction model: Insight gained using metabolomic approaches. *J. Mol. Cell. Cardiol.* 2009, 47, 835-845; (d) Node, K.; et al., Anti-inflammatory Properties of Cytochrome P450 Epoxygenase-Derived Eicosanoids. *Science* 1999, 285, 1276-1279; (e) Campbell, W. B. New role for epoxyeicosatrienoic acids as anti-inflammatory mediators. *Trends Pharmacol. Sci.* 2000, 21, 125-127; and (f) Inceoglu, B.; et al., Soluble epoxide hydrolase and epoxyeicosatrienoic acids modulate two distinct analgesic pathways. *Proc. Natl. Acad. Sci. U.S.A.* 2008, 105, 18901-18906).

NSAIDs target key enzymes involved in prostaglandin (PG) biosynthesis from arachidonic acid. However, morbidity and mortality due to NSAID-induced gastrointestinal (GI) toxicity are significant and frequent enough to limit the therapeutic use of this drug class. To mitigate this side effect caused primarily by COX-1 inhibition, COX-2 selective inhibitors, i.e., Coxibs, e.g., celecoxib (Celebrex) and rofecoxib (Vioxx), were designed to retain the beneficial anti-inflammatory and anti-hyperalgesic properties of NSAIDs but enhance GI tolerance. In spite of this design, at higher doses and long-term use, COX-2 selective inhibitors may lose selectivity and inhibit COX-1 in vivo, resulting in the aforementioned undesirable side effects. It has been demonstrated that drug combinations with low doses of NSAIDs and soluble epoxide hydrolase inhibitors (sEHIs) produce synergistic effects, with regard to anti-hyperalgesia and anti-inflammation, while decreasing side effects of Coxibs, e.g., cardiovascular toxicity.

Despite their benefits, there are practical challenges to developing combination therapies due to the cost and complexity of identifying optimal as well as safe dose regiments, dose ranges, and drug-drug interactions. Many of these challenges cannot be predicted a priori because two drugs that are safe when used independently of each other are not necessarily safe in combination. However, many of the challenges related to developing combination therapies, e.g., the prediction of pharmacodynamic and pharmacokinetic relationships, are substantially less complex if the polypharmacological action is derived from a single agent.

To prepare these single agents, there is a growing interest in a practice known as designed multiple ligands (DMLs) (See (a) Morphy, R.; et al., From magic bullets to designed multiple ligands. *Drug Discovery Today* 2004, 9, 641-651; (b) Morphy, R.; Rankovic, Z. Designed multiple ligands, an emerging drug discovery paradigm. *J. Med. Chem.* 2005, 48, 6523-6543; and (c) Morphy, R.; Rankovic, Z. The physicochemical challenges of designing multiple ligands. *J. Med. Chem.* 2006, 49, 4961-4970). DMLs are intended to enhance drug efficacy and optionally to improve drug safety relative to drugs that address only a single target by acting specifically on multiple targets, i.e., targeted polypharmacology. Also, DMLs have advantages over combination therapies because they circumvent the inherent problems associated with the formulation and administration of two or more agents. Furthermore, DMLs do not present safety issues that result from the differences in the pharmacodynamic and pharmacokinetic properties of individual agents. Therefore dual inhibition of COX-2 and sEH through a single molecule is likely to be more advantageous than co-administration of the drugs using combination therapy.

To date the Applicants are aware of only one example of a dual inhibitor related to sEH which was designed by GlaxoSmithKline, e.g., sEH/11β-HSD1 dual inhibitors (See International Patent Application No. PCT/US2009/051678, filed Jul. 24, 2009). As such, there is currently an unmet need in the field to which the present invention relates regarding the development of dual inhibitors that affect the P450 branch of the AA cascade. Surprisingly, the present invention meets this as well as other needs by providing a new class of DMLs, which are dual inhibitors of COX-2 and sEH.

BRIEF SUMMARY OF THE INVENTION

In a first embodiment, the present invention provides a compound of Formula I:

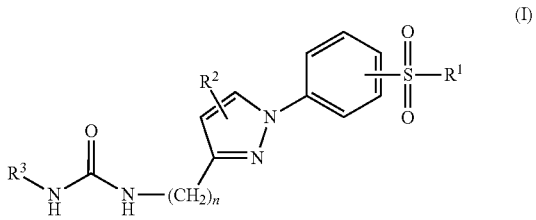

wherein $R^1$ is $C_{1-6}$ alkyl, —$NR^{1a}R^{1b}$ or cycloalkyl; $R^{1a}$ and $R^{1b}$ are each independently H or $C_{1-6}$ alkyl; $R^2$ is $C_{1-6}$ alkyl, cycloalkyl or aryl, wherein the cycloalkyl and aryl are each optionally substituted with $C_{1-6}$ alkyl; $R^3$ is cycloalkyl or aryl, each optionally substituted with from 1 to 3 $R^{3a}$ groups wherein each $R^{3a}$ is independently $C_{1-6}$ alkyl, $C_{1-6}$ alkoxy, halogen, $C_{1-6}$ haloalkyl or $C_{1-6}$ haloalkoxy; and subscript n is an integer from 0 to 6. Also included are the salts and isomers of a compound of Formula I.

In a second embodiment, the present invention provides a pharmaceutical composition including a compound of Formula I and a pharmaceutically acceptable excipient.

In a third embodiment, the present invention provides a method for inhibiting a soluble epoxide hydrolase, the method including contacting the soluble epoxide hydrolase with a therapeutically effective amount of a compound of Formula I, thereby inhibiting the soluble epoxide hydrolase.

In a fourth embodiment, the present invention provides a method for inhibiting a cyclooxygenase enzyme selected from the group consisting of cyclooxygenase-1 (COX-1) and cyclooxygenase-2 (COX-2), the method including contacting a cyclooxygenase enzyme with a therapeutically effective amount of a compound of Formula I, thereby inhibiting the cyclooxygenase enzyme.

In a fifth embodiment, the present invention provides a method for monitoring the activity of a soluble epoxide hydrolase, the method including contacting the soluble epoxide hydrolase with an amount of a compound of Formula I sufficient to produce a detectable change in the fluorescence of the soluble epoxide hydrolase by interacting with one or more tryptophan residues present in the catalytic site of said soluble epoxide hydrolase, thereby monitoring the activity of the soluble epoxide hydrolase.

In a sixth embodiment, the present invention provides a method of treating cancer, the method including administering to a subject in need thereof, a therapeutically effective amount of a compound of Formula I, thereby treating cancer.

In a seventh embodiment, the present invention provides a method of treating cancer, the method including contacting cancer cells with a therapeutically effective amount of a compound of Formula I, thereby treating cancer

DETAILED DESCRIPTION OF THE INVENTION

I. General

Figure 1:
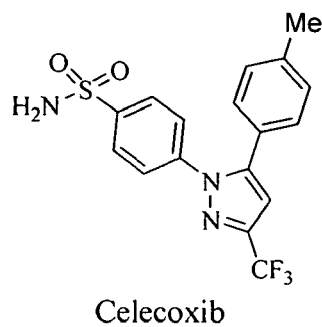
FIG. 1 shows structures of reference compounds for COX and sEH Inhibitors.
Figure 1:
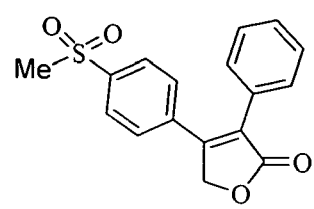
Figure 1:
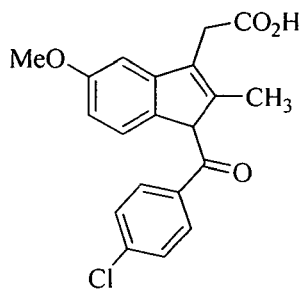
Figure 1:
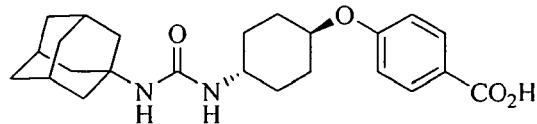
Figure 1:
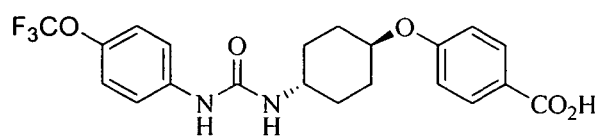

The present invention provides compounds and compositions, e.g., a series of compounds wherein a 1,5-biarylpyrazole group is conjugated to a urea group by a non-cleavable covalent chain, that are useful as dual COX-2/sEH inhibitors. These compounds and compositions recited herein demonstrate activity associated with the arachidonate cascade. The activity was demonstrated using a lipopolysaccharide (LPS) induced model of pain in the rat.

II. Definitions

The abbreviations used herein have their conventional meaning within the chemical and biological arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

As used herein, the term "alkyl" refers to a straight or branched, saturated, aliphatic radical having the number of carbon atoms indicated. For example, C$_1$-C$_6$ alkyl includes, but is not limited to, methyl, ethyl, propyl, butyl, pentyl, hexyl, iso-propyl, iso-butyl, sec-butyl, tert-butyl, etc.

As used herein, the term "alkoxy" refers to an alkyl radical as described above which also bears an oxygen substituent capable of covalent attachment to another hydrocarbon for example, methoxy, ethoxy or t-butoxy group.

As used herein, the term "halogen," by itself or as part of another substituent, means, unless otherwise stated, a fluorine, chlorine, bromine, or iodine atom.

As used herein, the term "haloalkyl" refers to alkyl as defined above where some or all of the hydrogen atoms are substituted with halogen atoms. Halogen (halo) preferably represents chloro or fluoro, but may also be bromo or iodo. For example, haloalkyl includes trifluoromethyl, fluoromethyl, 1,2,3,4,5-pentafluoro-phenyl, etc. The term "perfluoro" defines a compound or radical which has at least two available hydrogens substituted with fluorine. For example, perfluorophenyl refers to 1,2,3,4,5-pentafluorophenyl, perfluoromethane refers to 1,1,1-trifluoromethyl, and perfluoromethoxy refers to 1,1,1-trifluoromethoxy.

As used herein, the term "haloalkoxy" refers to alkoxy as defined above where some or all of the hydrogen atoms are substituted with halogen atoms. "Haloalkoxy" is meant to include monohaloalkyl(oxy) and polyhaloalkyl(oxy).

As used herein, the term "cycloalkyl" refers to a saturated or partially unsaturated, monocyclic, fused bicyclic or bridged polycyclic ring assembly containing from 3 to 12 ring atoms, or the number of atoms indicated. For example, C$_3$-C$_8$ cycloalkyl includes cyclopropyl, cyclobutyl, cyclopentyl, cyclohexyl, cycloheptyl, and cyclooctyl. Cycloalkyl also includes norbornyl and adamantyl.

As used herein, the term "aryl" means, unless otherwise stated, a polyunsaturated, aromatic, hydrocarbon substituent which can be a single ring or multiple rings (preferably from 1 to 3 rings) which are fused together or linked covalently. Examples include, but are not limited to, phenyl, biphenyl, naphthyl, and benzyl.

Substituents for the aryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O) NR"R''', —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro(C$_1$-C$_4$)alkoxy, and perfluoro(C$_1$-C$_4$)alkyl, in a number ranging from zero to the total number of open valences on the aromatic ring system; and where R', R" and R''' are independently selected from hydrogen, C$_1$-C$_8$ alkyl and heteroalkyl, unsubstituted aryl and heteroaryl, (unsubstituted aryl)-(C$_1$-C$_4$)alkyl, and (unsubstituted aryl)oxy-(C$_1$-C$_4$)alkyl.

As used herein, the phrases "pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors and colors, and the like. One of skill in the art will recognize that other pharmaceutical excipients are useful in the present invention.

As used herein, the phrase "soluble epoxide hydrolase" (sEH) refers to an enzyme which in endothelial, smooth muscle and other cell types converts EETs to dihydroxy derivatives called dihydroxyeicosatrienoic acids ("DHETs"). The cloning and sequence of the murine sEH is set forth in Grant et al., J. Biol. Chem. 268(23):17628-17633 (1993). The cloning, sequence, and accession numbers of the human sEH sequence are set forth in Beetham et al., Arch. Biochem. Biophys. 305(1):197-201 (1993). The amino acid sequence of human sEH is also set forth as SEQ ID NO:2 of U.S. Pat. No. 5,445,956; the nucleic acid sequence encoding the human sEH is set forth as nucleotides 42-1703 of SEQ ID NO:1 of that patent. The evolution and nomenclature of the gene is discussed in Beetham et al., DNA Cell Biol. 14(1):61-71 (1995). Soluble epoxide hydrolase represents a single highly conserved gene product with over 90% homology between rodent and human (Arand et al., FEBS Lett., 338:251-256 (1994)).

As used herein, the terms "cyclooxygenase" and "COX" refers to an enzyme that is associated with the formation of biological mediators called prostanoids, i.e., prostaglandin biosynthesis. Inhibition of COX is associated with relief from the symptoms of inflammation and pain. The terms "COX-1" and "COX-2" refer to two exemplary cyclooxygenase enzymes, i.e., isozymes of COX. COX-1 and COX-2 differ from each other in their regulation of expression and tissue distribution.

As used herein, the term "contacting" refers to the process of bringing into contact at least two distinct species such that they can react. It should be appreciated, however, the resulting reaction product can be produced directly from a reaction between the added reagents or from an intermediate from one or more of the added reagents which can be produced in the reaction mixture.

As used herein, the phrase "therapeutically effective amount" refers to an amount of a conjugated functional agent or of a pharmaceutical composition useful for treating or ameliorating an identified disease or condition, or for exhibiting a detectable therapeutic or inhibitory effect. The effect can be detected by any assay method known in the art.

As used herein, the terms "treat", "treating" and "treatment" refer to any indicia of success in the treatment or amelioration of an injury, pathology or condition, including any objective or subjective parameter such as abatement;

remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation.

As used herein, the term "modulate" refers to the ability of a compound to increase or decrease the function, or activity, of the associated activity (e.g., soluble epoxide hydrolase, i.e. sEH. "Modulation", as used herein in its various forms, is meant to include antagonism and partial antagonism of the activity associated with sEH.

As used herein, the terms "patient" or "subject" refers to a living organism suffering from or prone to a condition that can be treated by administration of a pharmaceutical composition as provided herein. Non-limiting examples include humans, other mammals and other non-mammalian animals.

As used herein the term "inhibiting," refers to the partial or total blocking of the function or associated activity. Inhibitors of sEH are compounds that bind to, partially or totally block the sEH enzyme's activity.

As used herein, the term "reduce or inhibit," when used in reference to angiogenesis, means that the amount of new blood vessel formation that occurs in the presence of an antagonist is decreased below the amount of blood vessel formation that occurs in the absence of an exogenously added antagonist. The terms "reduce" and "inhibit" are used together because it is recognized that the amount of angiogenesis can be decreased below a level detectable by a particular assay method and, therefore, it may not be possible to determine whether angiogenesis is reduced to a very low level or completely inhibited.

The terms "a," "an," or "a(n)", when used in reference to a group of substituents or "substituent group" herein, mean at least one. For example, where a compound is substituted with "an" alkyl or aryl, the compound is optionally substituted with at least one alkyl and/or at least one aryl, wherein each alkyl and/or aryl is optionally different. In another example, where a compound is substituted with "a" substituent group, the compound is substituted with at least one substituent group, wherein each substituent group is optionally different.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, or physiological conditions.

III. Compounds

In some embodiments, the present invention provides a compound of Formula I:

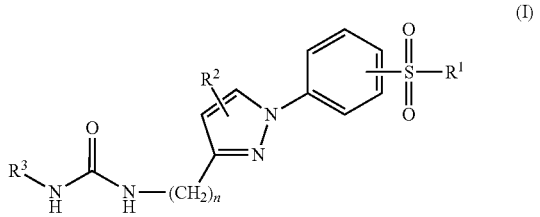

wherein $R^1$ is $C_{1-6}$ alkyl, $-NR^{1a}R^{1b}$ or cycloalkyl; $R^{1a}$ and $R^{1b}$ are each independently selected from the group consisting of H and $C_{1-6}$ alkyl; $R^2$ is $C_{1-6}$ alkyl, cycloalkyl or aryl, wherein the cycloalkyl and aryl are each optionally substituted with $C_{1-6}$ alkyl; $R^3$ is cycloalkyl or aryl, each optionally substituted with from 1 to 3 $R^{3a}$ groups wherein each $R^{3a}$ is independently selected from $C_{1-6}$ alkyl, $C_{1-6}$ alkoxy, halogen, $C_{1-6}$ haloalkyl or $C_{1-6}$ haloalkoxy; and subscript n is an integer from 0 to 6. Also included are the salts and isomers of a compound of Formula I.

In some other embodiments, the present invention provides a compound having the formula Ia:

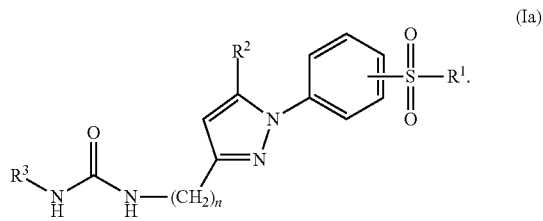

In some embodiments, the present invention provides a compound having the formula Ib:

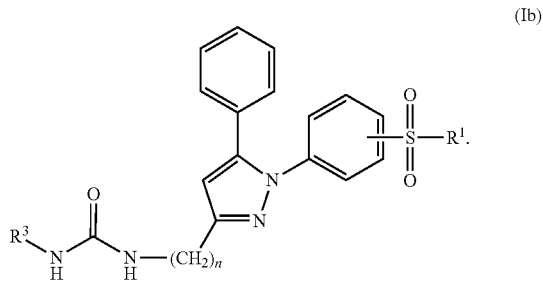

In some other embodiments, the present invention provides a compound having the formula Ic:

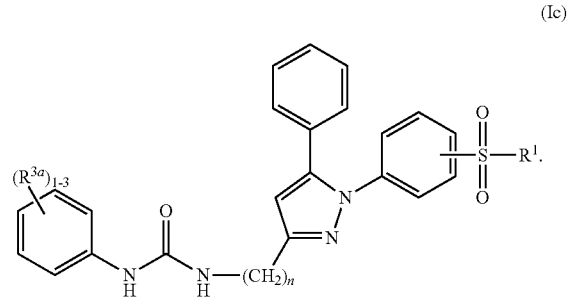

In some embodiments, the present invention provides a compound of Formula I, wherein $R^1$ is $C_{1-6}$ alkyl or $-NR^{1a}R^{1b}$; $R^{1a}$ and $R^{1b}$ are each independently H and $C_{1-6}$ alkyl; $R^2$ is aryl, optionally substituted with $C_{1-6}$ alkyl; and $R^3$ is cycloalkyl or aryl, each optionally substituted with from 1 to 3 $R^{3a}$ groups wherein each $R^{3a}$ is independently $C_{1-6}$ alkyl, halogen, $C_{1-6}$ haloalkyl and $C_{1-6}$ haloalkoxy. In some other embodiments, $R^1$ is methyl, ethyl, propyl, $-NH_2$ and $-NMe_2$; $R^2$ is phenyl, optionally substituted with a member selected from methyl, ethyl or propyl; and $R^3$ is selected from cyclohexyl, cycloheptyl, cyclooctyl, adamantyl or phenyl, wherein the phenyl is optionally substituted with from 1 to 3 $R^{3a}$ groups wherein each $R^{3a}$ is independently methyl, ethyl, propyl, Cl, Br, I, $-CF_3$ or $-OCF_3$.

In some other embodiments, the present invention provides a compound of Formula I, wherein the compound is selected from:
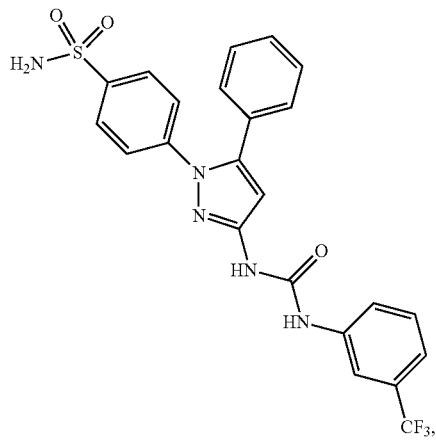
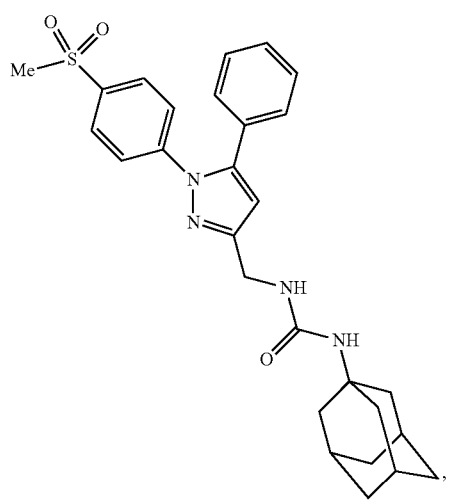
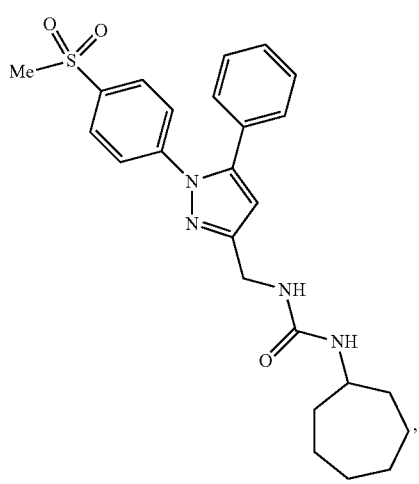
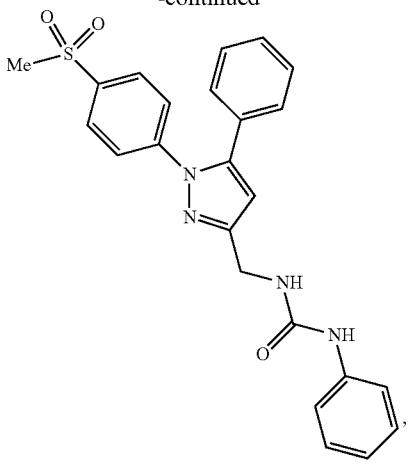
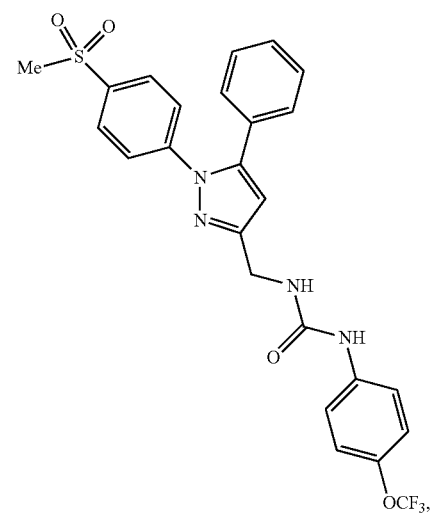
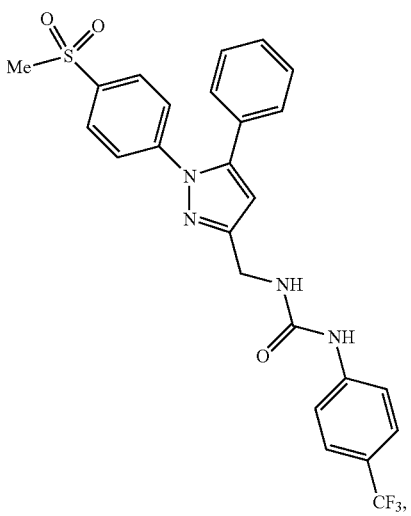

11
-continued
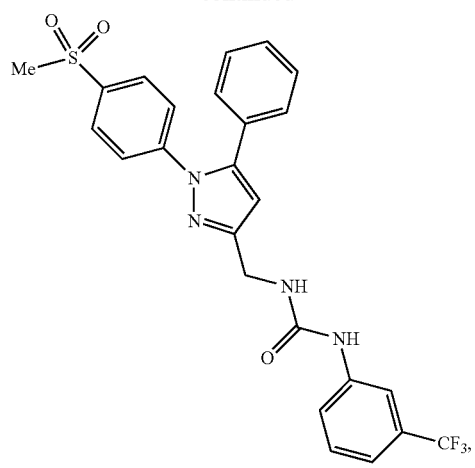
12
-continued
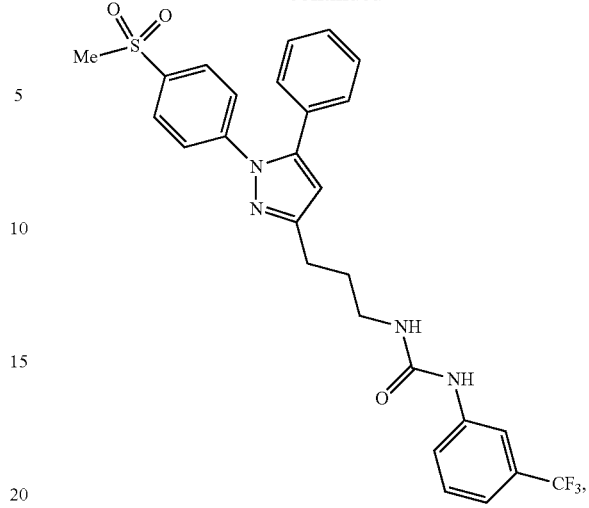
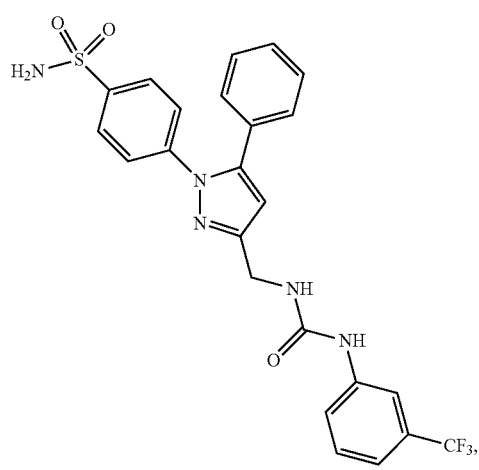
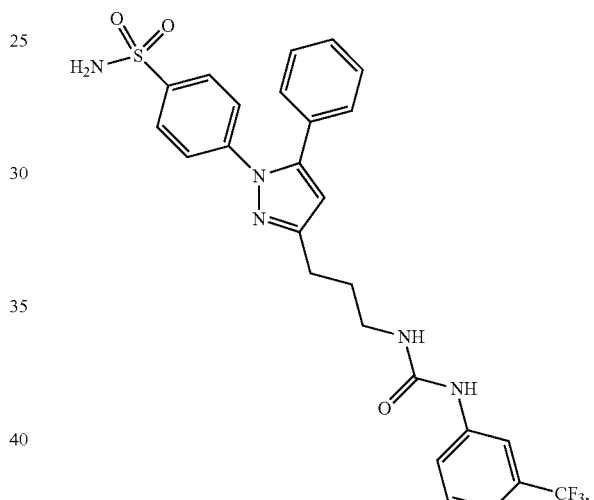
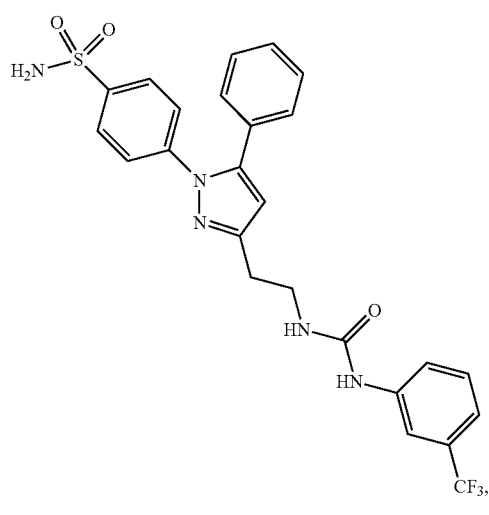
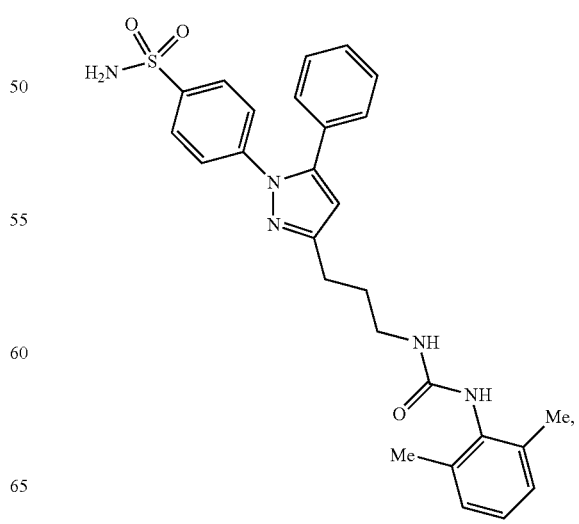

13
-continued
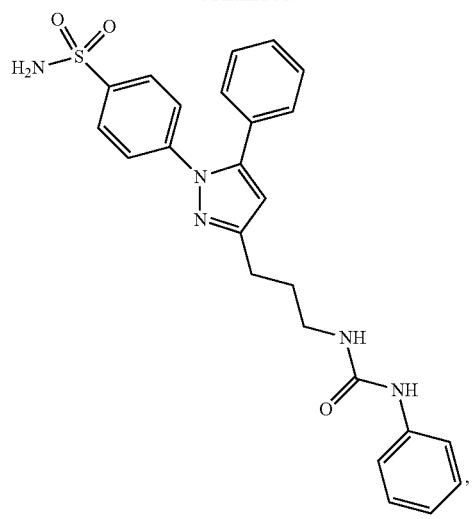
14
-continued
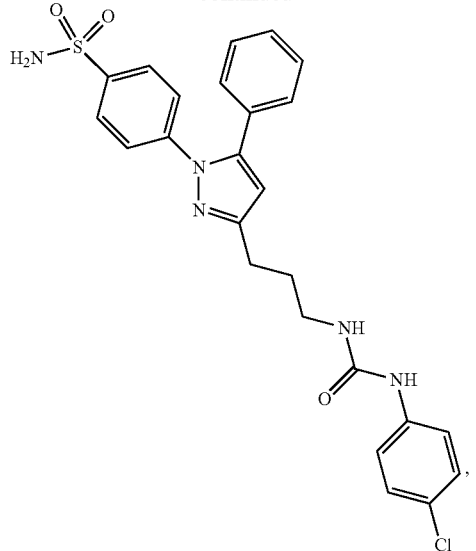
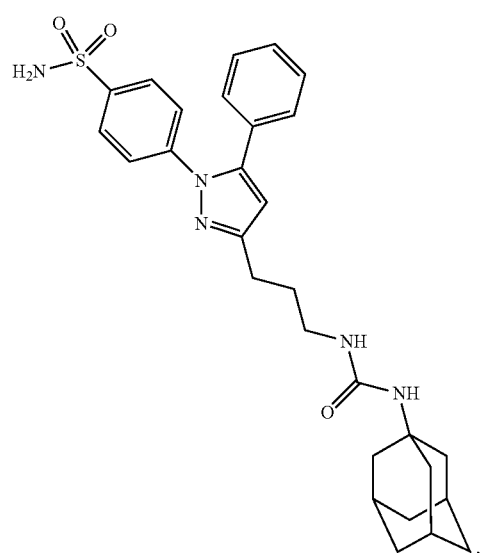
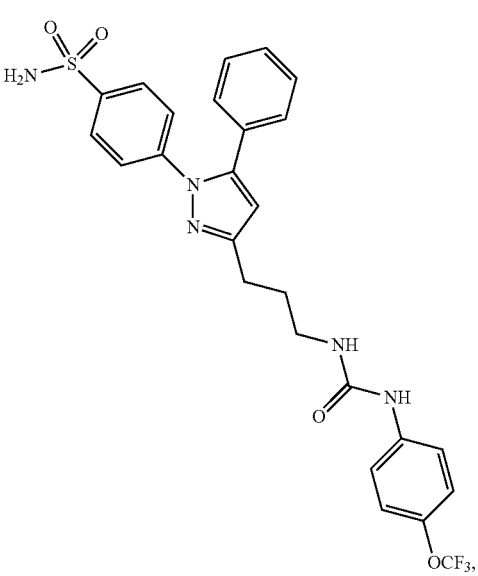
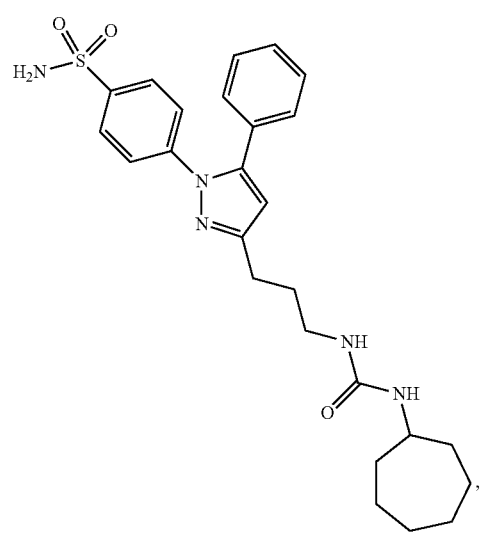

-continued

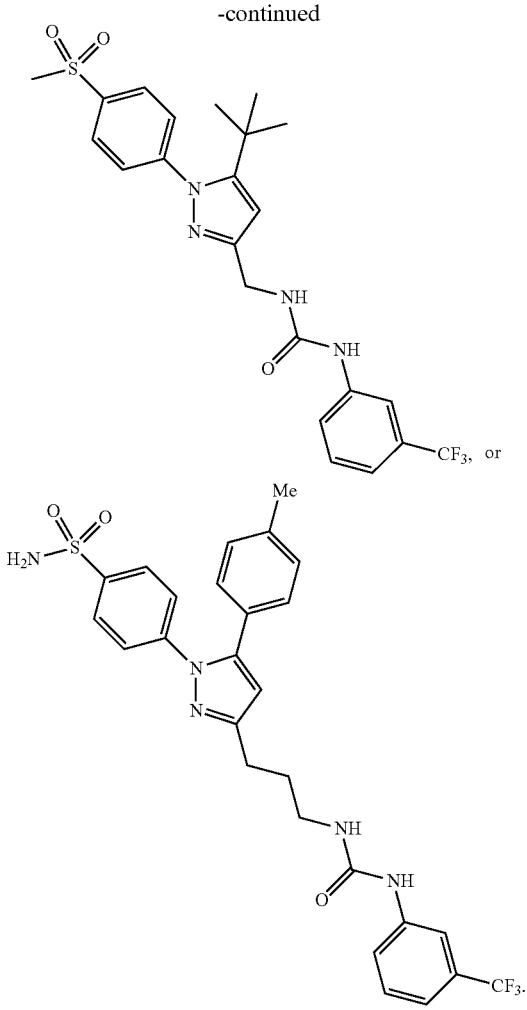

In other embodiments, the compound can be:

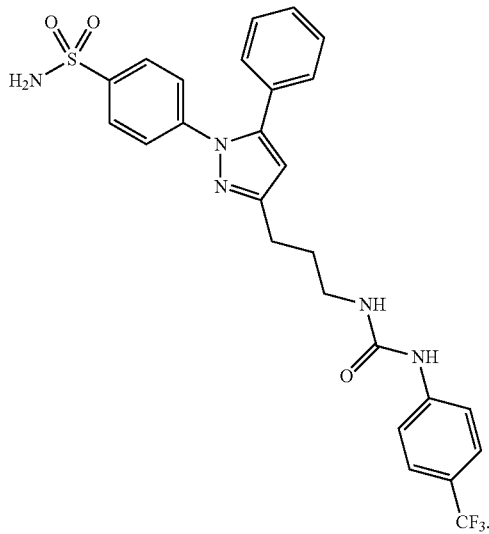 [SMILES: NS(=O)(=O)c1ccc(-n2nc(CCCNC(=O)Nc3ccc(C(F)(F)F)cc3)cc2-c2ccccc2)cc1]

The compounds of the present invention may exist as salts. The present invention includes such salts. Examples of applicable salt forms include hydrochlorides, hydrobromides, sulfates, methanesulfonates, nitrates, maleates, acetates, citrates, fumarates, tartrates (eg (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present invention contain both basic and acidic functionalities that allow the compounds to be converted into either base or acid addition salts.

Other salts include acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, and quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

Pharmaceutically acceptable salts include salts of the active compounds which are prepared with relatively non-toxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques.

Isomers include compounds having the same number and kind of atoms, and hence the same molecular weight, but differing in respect to the structural arrangement or configuration of the atoms.

It will be apparent to one skilled in the art that certain compounds of this invention may exist in tautomeric forms, all such tautomeric forms of the compounds being within the scope of the invention. Tautomer includes one of two or more structural isomers which exist in equilibrium and which are readily converted from one isomeric form to another.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, the compounds of the present invention may also contain unnatural proportions of atomic isotopes at one or more of the atoms that constitute such compounds. For example, the compounds of the present invention may be radiolabeled with radioactive isotopes, such as for example deuterium ($^2$H), tritium ($^3$H), iodine-125 ($^{125}$I), carbon-13 ($^{13}$C), or carbon-14 ($^{14}$C). All isotopic variations of the compounds of the present invention, whether radioactive or not, are encompassed within the scope of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Figure 4:
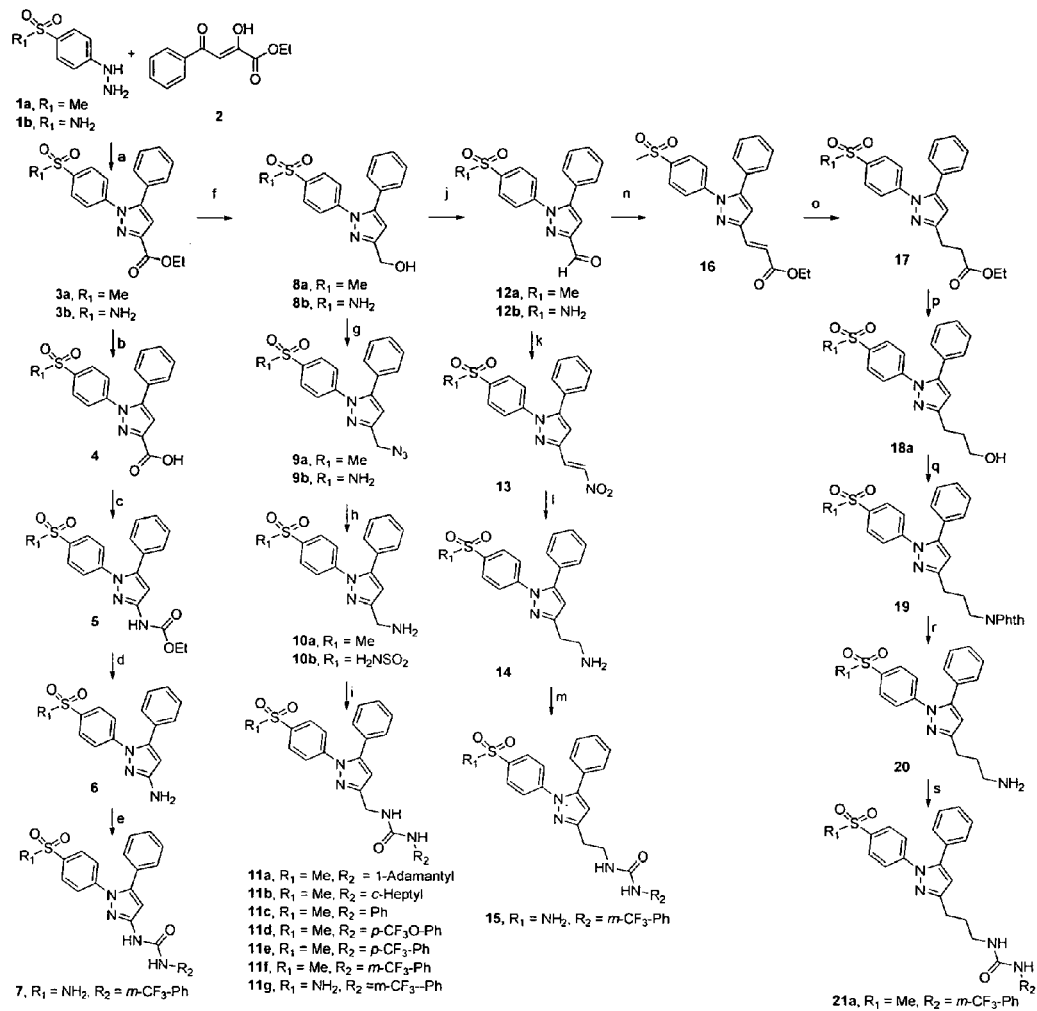
FIG. 4 shows an example synthesis of sEH/COX-2 Dual Inhibitors 7, 11a-g, 15, 21a. The letters associated with the reaction arrows indicate the following reagents and conditions: (a) EtOH, AcOH, reflux, 2 hours; (b) LiOH, THF, water, room temperature, 12 hours; (c) DPPA, $Et_3N$, EtOH, 1,4-dioxane, reflux, 12 hours; (d) 10% NaOH, EtOH, reflux, 5 hours; (e) $R_2$—NCO, $Et_3N$, DMF, 0° C. to room temperature, 12 hours; (f) LAH, THF, room temperature, 6 hours; (g) i) MSCl, $Et_3N$, 0° C., 2 hours, ii) $NaN_3$, 1,4-dioxane, water, 80° C., 2 hours; (h) Pd/C, $H_2$, EtOAc, 2 hours; (i) $R_2$—NCO, DMF, room temperature, 12 hours; (j) PCC, DCM, room temperature, 6 hours; (k) i) $MeNO_2$, $AcONH_4$, reflux, 1 hours; (l) LAH, THF, room temperature, 6 hours; (m) R—NCO, DMF, room temperature, 12 hours; (n) triethyl phosphonoacetate, NaH, THF, 0° C., 1 hours; (o) Pd/C, $H_2$, EtOAc, 2 hours; (p) LAH, THF, 6 hours; (q) $PPh_3$, phthalimide, DIAD, THF, room temperature, 12 hours; (r) 35% hydrazine, $CH_2Cl_2$, MeOH, room temperature, 1 day; (s) $R_2$—NCO, DMF, room temperature, 12 hours.
Figure 5:
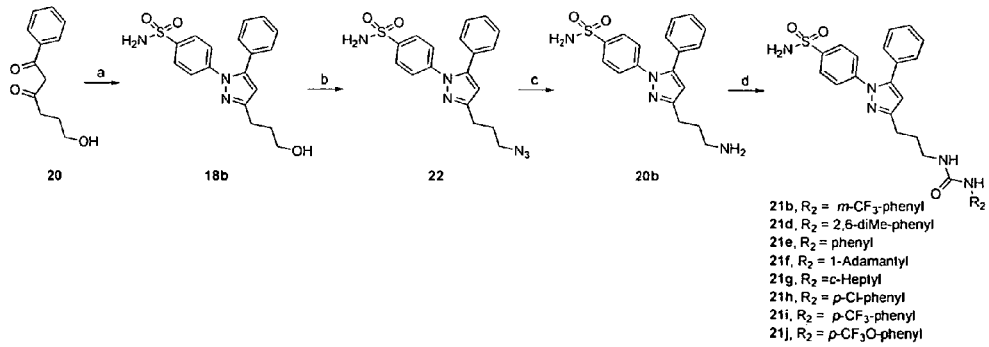
FIG. 5 shows an example synthesis of sEH/COX-2 Dual Inhibitors 21b, d-j. The letters associated with the reaction arrows indicate the following reagents and conditions: (a) p-sulfoamidophenylhydrazine hydrochloride, EtOH, AcOH, reflux, 2 hours; (b) i) MSCl, $Et_3N$, DCM, 0° C., 2 hours, ii) $NaN_3$, 1,4-dioxane, water, reflux, 6 hours; (c) Pd/C, $H_2$, EtOAc, room temperature, 2 hours; (d) $R_3$—NCO, DMF, room temperature, 12 hours.
Figure 6:
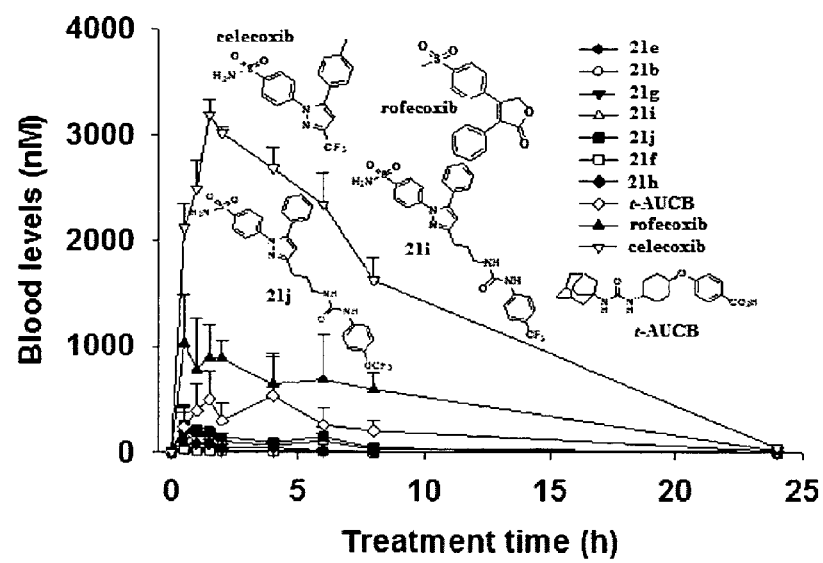
FIG. 6 shows PK analyses of selected dual COX-2/sEH inhibitors 21b, e-j in mice.
Figure 6:
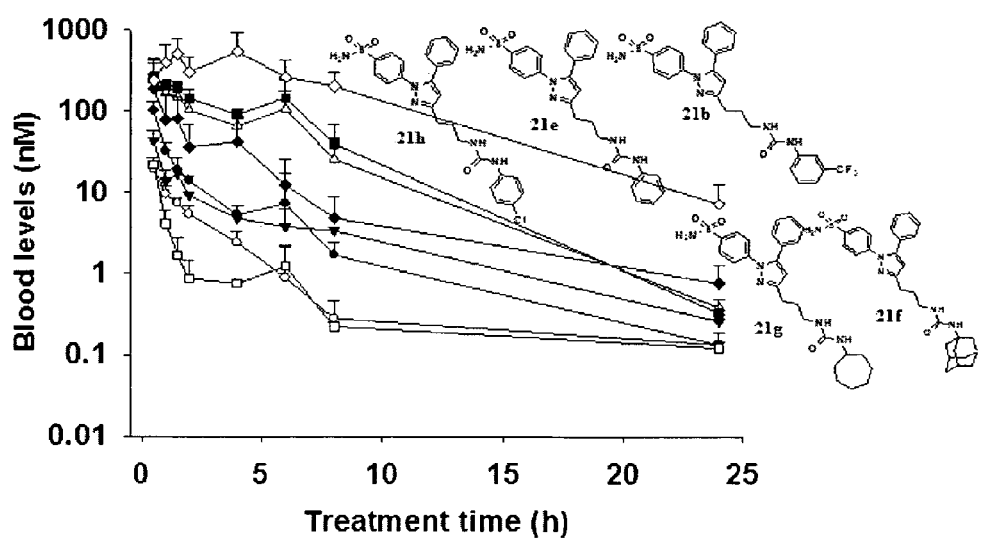
Figure 7:
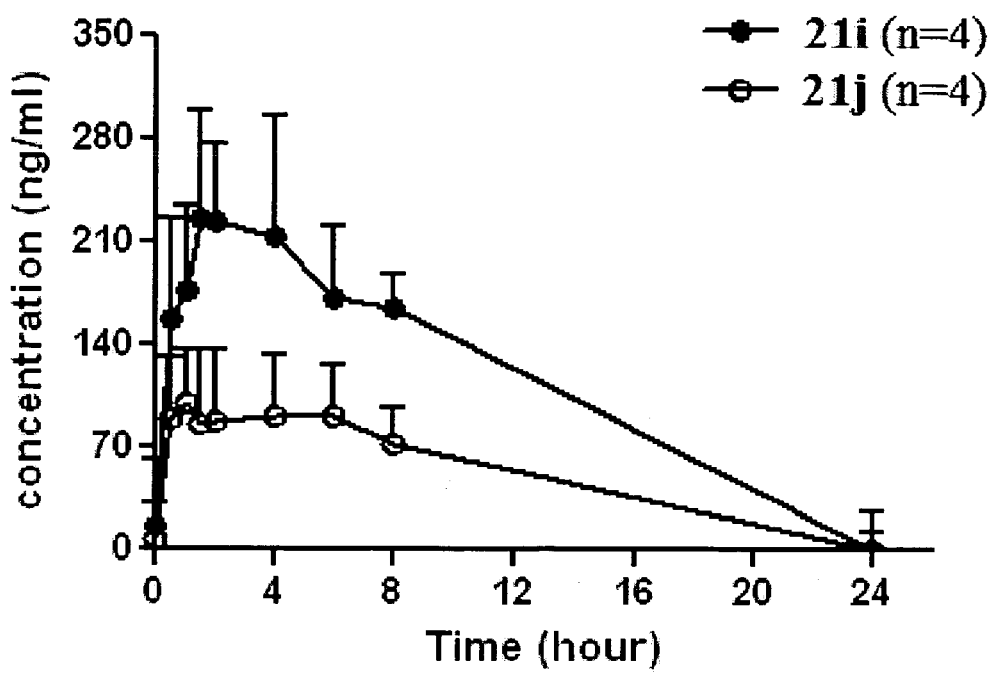
FIG. 7 shows PK analyses of dual COX-2/sEH inhibitors 21i and 21j in rats.
Figure 8:
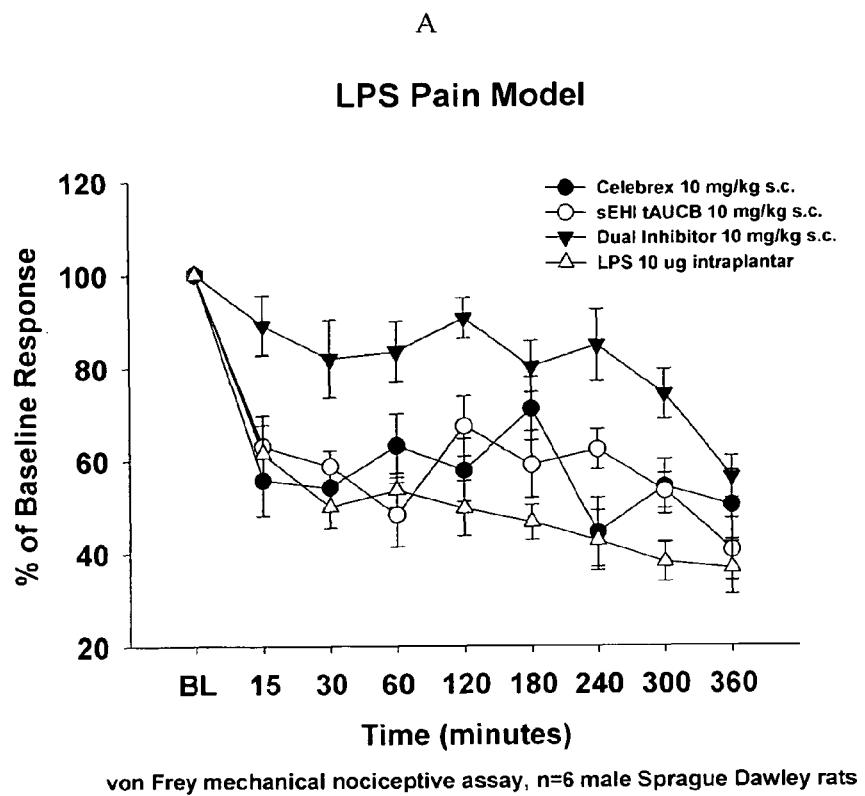
FIG. 8 shows Von Frey mechanical nociceptive assay with COX-2/sEH inhibitor 21i.
Figure 8:
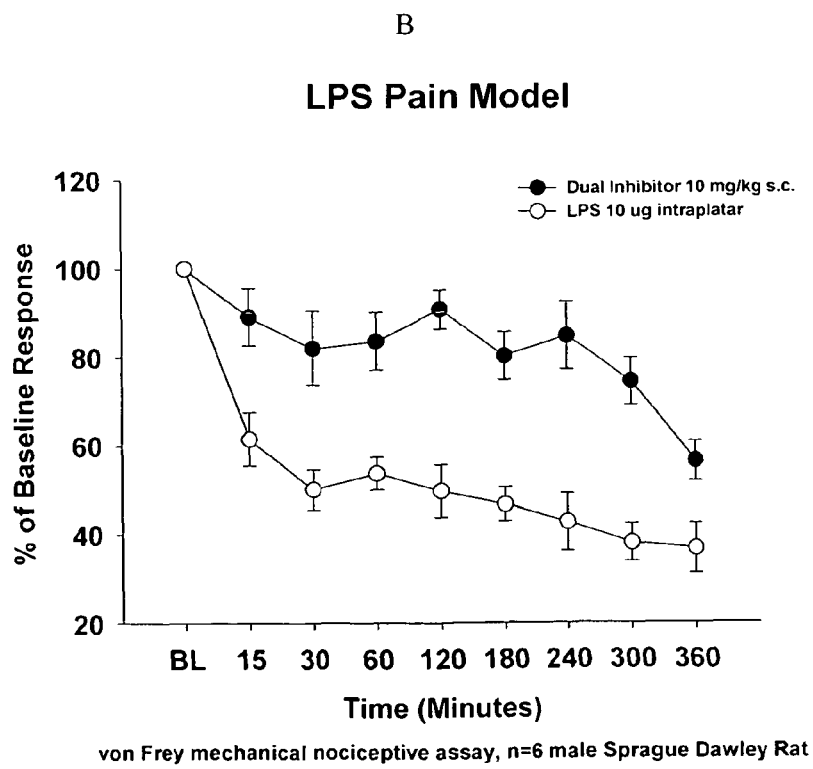
Figure 9:
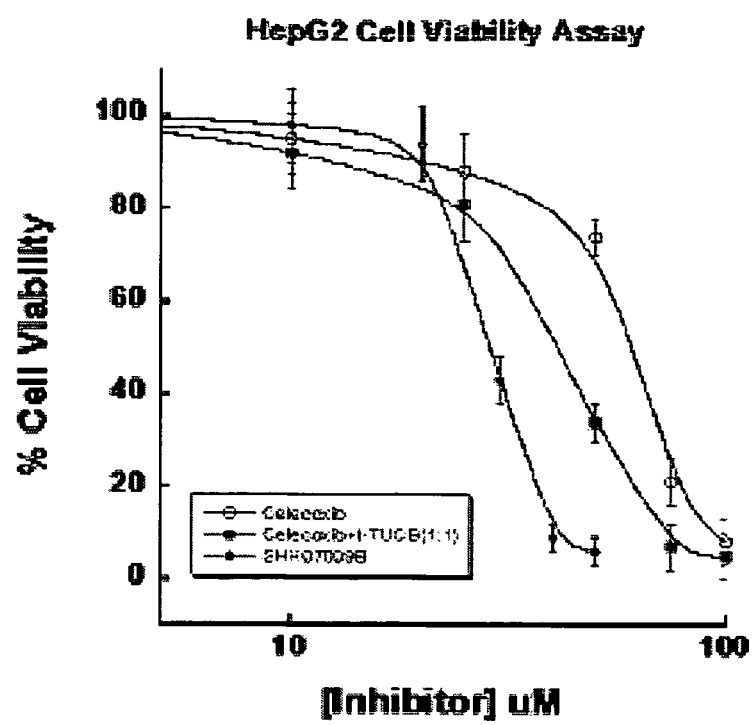
FIG. 9 shows dose dependence of dual inhibitor SHH07009B (compound 21i), a combination of Celecoxib and t-TUCB, and Celecoxib alone on HepG2 cell viability. The COX-2 selective inhibitor, Celecoxib, alone has an anti-cancer effect. However, when combined with the sEH inhibitor, t-TUCB, it increases this latter compound ability to kill cancer cells. Dual inhibitor SHH07009B (compound 21i), which inhibits both sEH and COX-2 (see Table 1) is more efficient than Celecoxib in combination or not with t-TUCB in killing the cancer cells.
Figure 10:
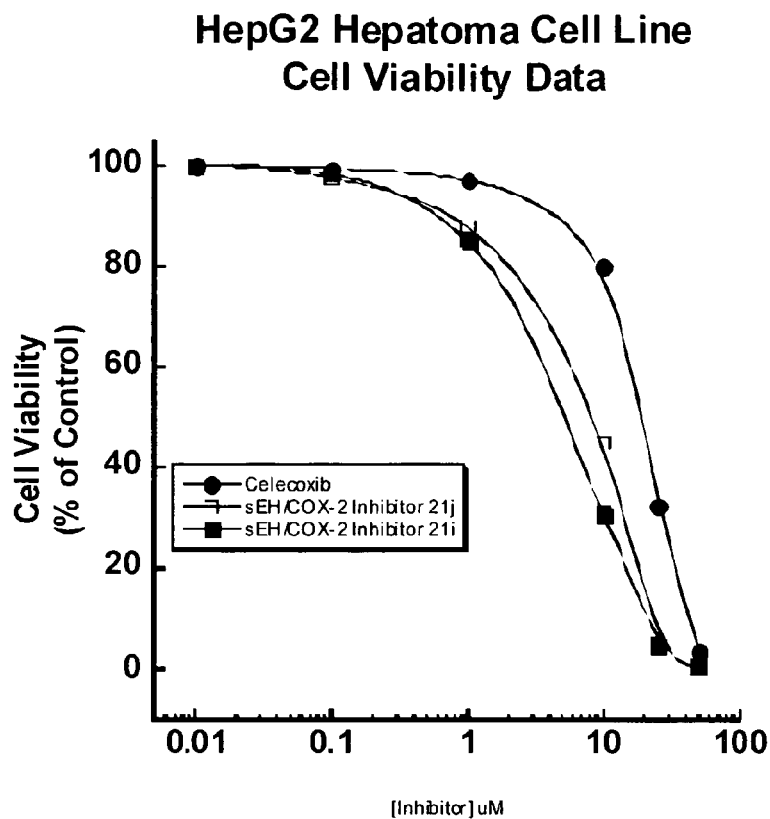
FIG. 10 shows COX-2/sEHi dual inhibitors are more potent than celecoxib in inhibiting HepG2 cell growth. Cell viability was determined using MTT cell viability detection reagent after 24 hours of incubation. Effective concentrations ($EC_{50}$) values for celecoxib=20±4 µM, sEH/COX-2 Inhibitor 21j=10±2 µM, sEH/COX-2 Inhibitor 21i=4.5±0.5 µM.
Figure 11:
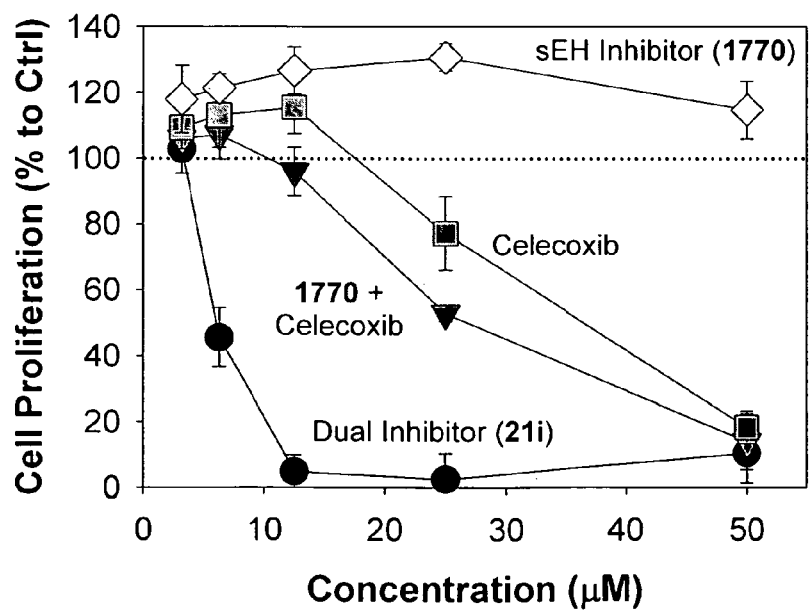
FIG. 11 shows HUVEC cell proliferation of compound 1770, celecoxib and dual inhibitor 21i. HUVEC cells are treated with test compounds for 3 days, cell proliferation was assessed by MTT assay, expressed as % to controls.
Figure 12:
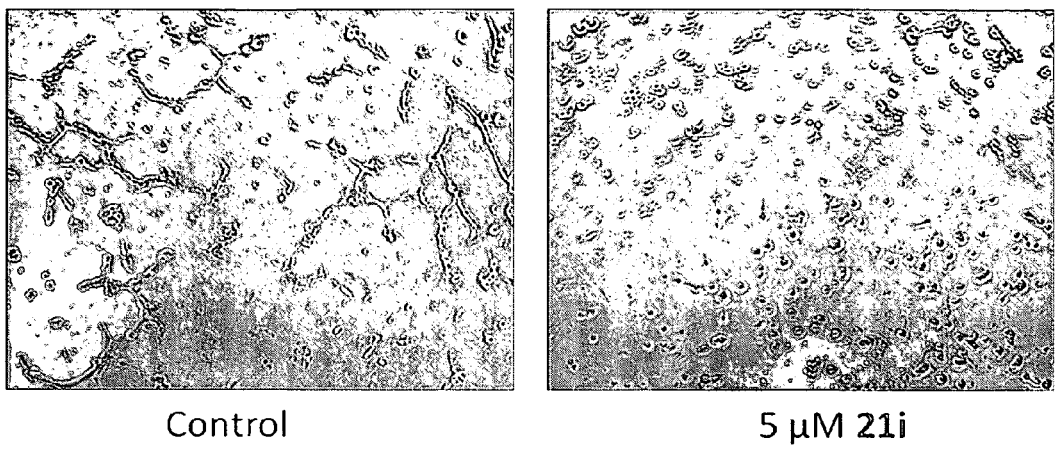
FIG. 12 shows HUVEC tube formation assay of dual inhibitor 21i. HUVEC cells are treated with 21i for 4-6 hours. 21i inhibits endothelial proliferation assay of HUVEC cells.
Figure 13:
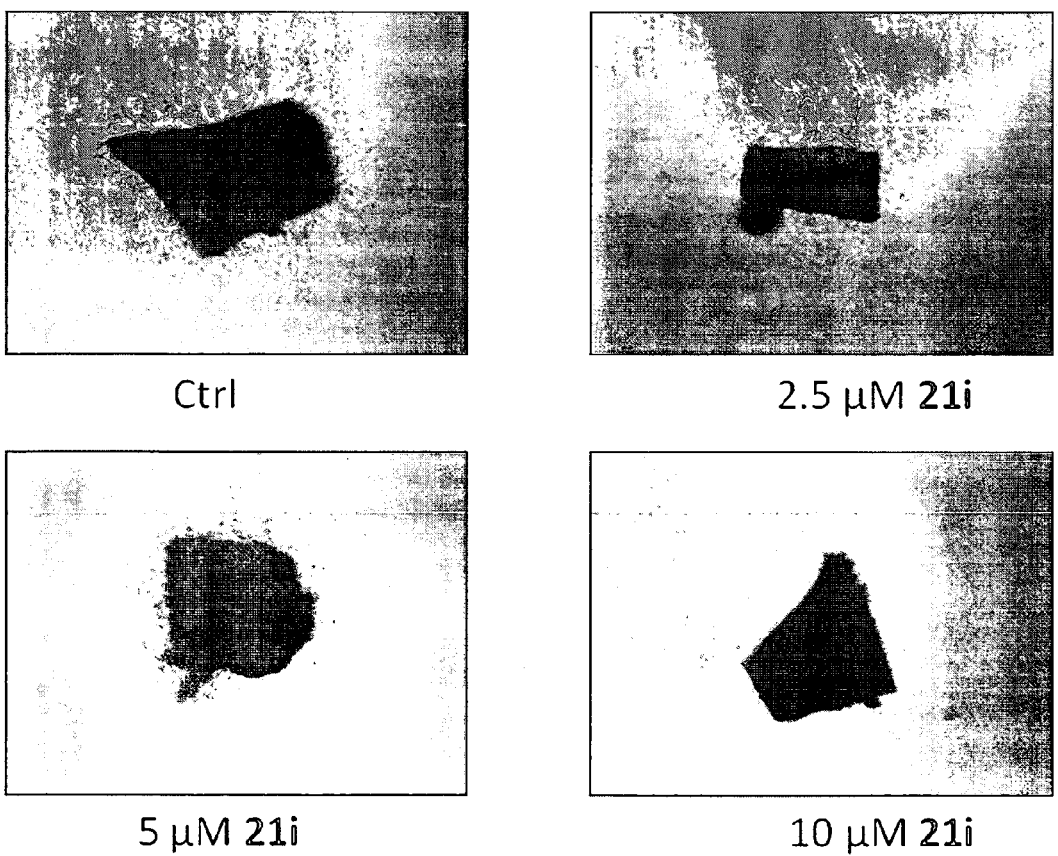
FIG. 13 shows mouse aortic ring assay of 21i. 21i inhibited vessel sprouting in mouse aortic ring assay in a dose-dependent manner.
Figure 14:
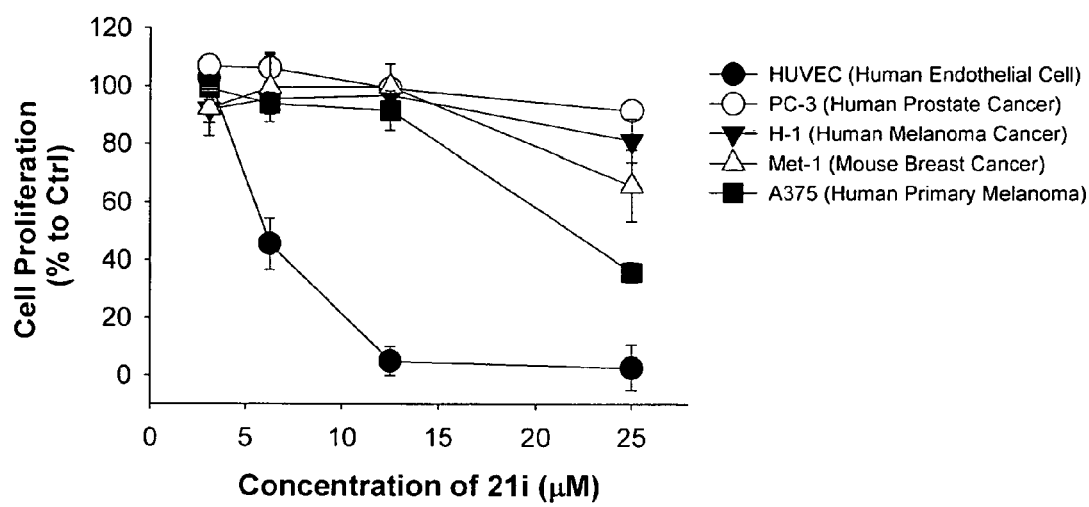
FIG. 14 shows compound 21i selectively inhibits endothelial proliferation but not cancer cells, its $IC_{50}$ values in cancer cells are 5-10 times higher than that of endothelial cells. This result demonstrates 21i is a new class of selective inhibitor of endothelial proliferation.
Figure 15:
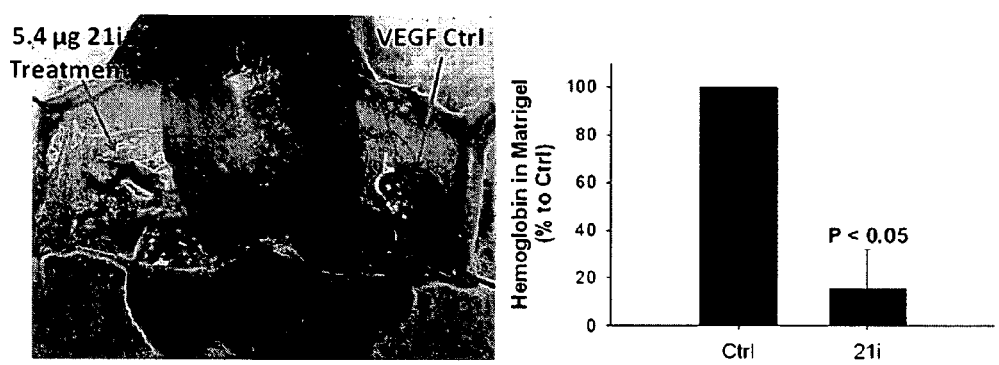
FIG. 15 shows compound 21i inhibits VEGF-induced angiogenesis in C57BL/6 mice. (Left) animal picture, (Right) hemoglobin content inside the Matrigel, expressed as % to Ctrl (n=6 mice per group).
Figure 16:
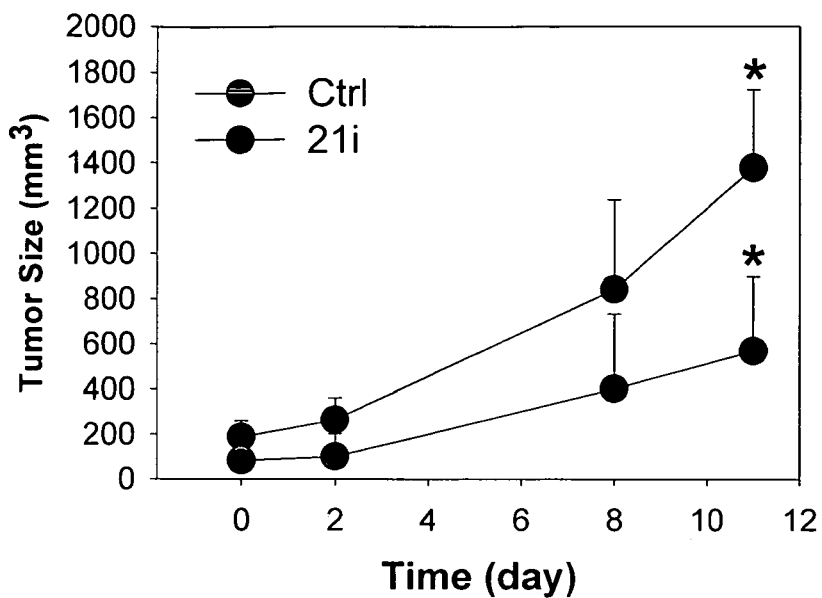
FIG. 16 shows compound 21i inhibits primary tumor growth of Met-1 breast cancer in FVB mice at dose=0.1 mg/kg/day administered by mini-pump.
Figure 17:
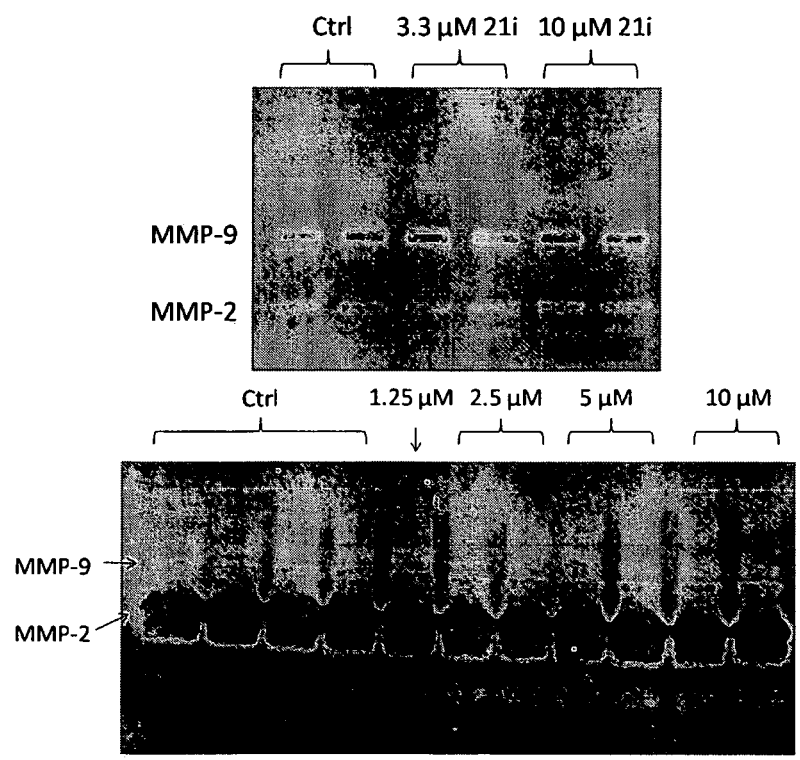
FIG. 17 shows compound 21i has no effect on MMP activity in PC-3 (left) and HUVEC (right) cells. This result demonstrates that 21i inhibits angiogenesis via an MMP-independent mechanism.

The compounds of the present invention can be made by a variety of methods known in the art. For example, compounds 7, 11a-g, 15, and 21a, presented in FIG. 4 and elsewhere herein, can be prepared with a non-cleavable methylene chains between a pyrazole ring, as a COX-2 fragment, and a urea, as a sEH fragment. See FIG. 4 wherein compound 3a and 3b can be prepared by regioselective cyclization of either 4-methylsulfonylphenylhydrazine 1a or 4-amidosulfonylphenylhydrazine 1b with β-diketone 2. Compounds 21b, d-j can also be prepared from the β-diketone 20. Compounds 9h and 21b can be prepared using similar methods. Compound 7 can be prepared by the reaction with 3-(trifluoromethyl)phenyl isocyanate and an aminopyrazole 6. The aminopyrazole 6 can be obtained by hydrolysis from corresponding ethyl carbamate 5. The Curtius reaction can be employed to convert the carboxylic acid 4, in the presence of EtOH, into compound 5. Compounds 11a-h can be prepared by the reaction of various isocyanates with amine 11a or 11b, which can be obtained by LAH reduction, mesylation, azide formation and Pd/C catalysed hydrogenation starting from the common intermediate 3a or 3b. Compound 15 can be prepared by the reaction of 3-(trifluoromethyl)phenyl isocyanates with amine 14, which can be obtained via the Henry reaction, followed by LAH reduction from aldehyde 12b. Compound 21a can be obtained by the reaction of 3-(trifluoromethyl)phenyl isocyanates with amine 20, which can be obtained, sequentially, via the Horner-Wadsworth-Emmons reaction, Pd/C hydrogenation, LAH reduction, Mitsunobu reaction and hydrazine hydrolysis from the aldehyde 12a. Compounds 21b, d-j can be prepared using the reactions shown in FIG. 5. The three-carbon linker in compound 18b can be introduced by the reaction of p-amidosulfonylphenylhydrazine hydrochloride with 1-phenyl-1,3-dione-3-propanol 17, which can be obtained by the reaction of acetophenone with γ-butyrolactone. The amine 20b can be prepared by hydrogenation on Pd/C from an azide 22. A series of dual inhibitors 21b, d-j possessing three methylene chain as a linker can be obtained by reacting amine 21 with various isocyanates.

IV. Pharmaceutical Composition

In some embodiments, the present invention provides a pharmaceutical composition including a pharmaceutically acceptable excipient and the compound of formula I.

The compounds of the present invention can be prepared and administered in a wide variety of oral, parenteral and topical dosage forms. Oral preparations include tablets, pills, powder, dragees, capsules, liquids, lozenges, gels, syrups, slurries, suspensions, etc., suitable for ingestion by the patient. The compounds of the present invention can also be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. The compounds described herein of this invention can also be administered by intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995). Accordingly, the present invention also provides pharmaceutical compositions including a pharmaceutically acceptable carrier or excipient and either a compound of Formula (I), or a pharmaceutically acceptable salt of a compound of Formula (I).

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton Pa. ("Remington's").

In powders, the carrier is a finely divided solid, which is in a mixture with the finely divided active component. In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Suitable solid excipients are carbohydrate or protein fillers include, but are not limited to sugars, including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain the compounds described herein mixed with a filler or binders such as lactose or starches, lubricants such as talc or magnesium stearate, and, optionally, stabilizers. In soft capsules, the compounds described herein may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending a compounds described herein in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compounds described herein can be delivered by transdermally, by a topical route, formulated as applicator sticks, solutions, suspensions, emulsions, gels, creams, ointments, pastes, jellies, paints, powders, and aerosols.

The compounds and compositions described herein can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., *Gao Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

The pharmaceutical formulations of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms.

In another embodiment, the compounds described herein can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compounds described herein into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

The dosage regimen also takes into consideration pharmacokinetics parameters well known in the art, i.e., the rate of absorption, bioavailability, metabolism, clearance, and the like (see, e.g., Hidalgo-Aragones (1996) *J. Steroid Biochem. Mol. Biol.* 58:611-617; Groning (1996) *Pharmazie* 51:337-341; Fotherby (1996) *Contraception* 54:59-69; Johnson (1995) *J. Pharm. Sci.* 84:1144-1146; Rohatagi (1995) *Pharmazie* 50:610-613; Brophy (1983) *Eur. J. Clin. Pharmacol.* 24:103-108; the latest Remington's, supra). The state of the art allows the clinician to determine the dosage regimen for each individual patient, the compound administered and disease or condition treated.

Single or multiple administrations of the compounds described herein can be administered depending on the dosage and frequency as required and tolerated by the patient. The formulations should provide a sufficient quantity of active agent to effectively treat the disease state. Thus, in one embodiment, the pharmaceutical formulations for oral administration of the compounds described herein is in a daily amount of between about 0.5 to about 20 mg per kilogram of body weight per day. In an alternative embodiment, dosages are from about 1 mg to about 4 mg per kg of body weight per patient per day are used. Lower dosages can be used, particularly when the drug is administered to an anatomically secluded site, such as the cerebral spinal fluid (CSF) space, in contrast to administration orally, into the blood stream, into a body cavity or into a lumen of an organ. Substantially higher dosages can be used in topical administration. Actual methods for preparing parenterally administrable compositions of the compounds described herein will be known or apparent to those skilled in the art and are described in more detail in such publications as Remington's, supra. See also Nieman, In "Receptor Mediated Antisteroid Action," Agarwal, et al., eds., De Gruyter, New York (1987).

The compounds described herein can be used in combination with one another, with other active agents known to be suitable for use therewith, or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another.

After a pharmaceutical composition including a compounds described herein has been formulated in an acceptable carrier, it can be placed in an appropriate container and labeled for treatment of an indicated condition. For administration of the compounds described herein, such labeling would include, e.g., instructions concerning the amount, frequency and method of administration.

In another embodiment, the compositions of the present invention are useful for parenteral administration, such as intravenous (IV) administration or administration into a body cavity or lumen of an organ. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

V. Method of Inhibiting sEH and COX

In some embodiments, the present invention provides a method for inhibiting a soluble epoxide hydrolase, the method including contacting the sEH with an amount of a compound of Formula I sufficient to inhibit the sEH, thereby inhibiting the sEH. In some embodiments, the amount of a compound of Formula I is a therapeutically effective amount. In some other embodiments, the compound further inhibits an enzyme. In other embodiments, the enzyme is a cyclooxygenase enzyme selected from cyclooxygenase-1 (COX-1) or cyclooxygenase-2 (COX-2).

A compound of the present invention inhibits sEH when the concentration of the compound is about 10,000 nM or less and the activity of sEH is reduced by at least 50%. In some embodiments, the concentration of the compound is about 5.00 nM or less; 2,500 nM or less; 1,125 nM or less; 500 nM or less; 250 nM or less; 125 nM or less; 75 nM or less; 30 nM or less; 25 nM or less; 10 nM or less; 5 nM or less; 1 nM or less; 0.5 nM or less; or 0.2 nM or less, and the activity of sEH is reduced by at least 50%. In some other embodiments, the activity of sEH is reduced by at least about 50, 55, 60, 65, 70, 75, 80, 85, 90, 95, 96, 97, 98 or 99%.

A compound of the present invention inhibits COX-2 when the concentration of the compound is about 100 $\mu$M or less and the activity of COX-2 is reduced by at least 50%. In some embodiments, the concentration of the compound is about 50 $\mu$M or less; 25 $\mu$M or less; 13 $\mu$M or less; 10 $\mu$M or less; 5 $\mu$M or less; 2 $\mu$M or less; 1 $\mu$M or less; 0.5 $\mu$M or less; or 0.2 $\mu$M or less, and the activity of COX-2 is reduced by at least 50%. In some other embodiments, the activity of COX-2 is reduced by at least about 50, 55, 60, 65, 70, 75, 80, 85, 90, 95, 96, 97, 98 or 99%.

In some other embodiments, the sEH is inhibited without substantially inhibiting a cyclooxygenase enzyme selected from the group consisting of cyclooxygenase-1 (COX-1) and cyclooxygenase-2 (COX-2). In some embodiments, the sEH is inhibited without substantially inhibiting COX-1. For example, COX-1 is considered not substantially inhibited when, in the presence of the composition of the present invention, the activity of COX-1 is not reduced by more than about 50%, relative to the COX-1 activity in the absence of the composition of the present invention. In some embodiments, the activity of COX-1 is not reduced by more than about 40, 35, 30, 25, 20, 15, 10, 5, 2, 1, or 0.5%, relative to the COX-1 activity in the absence of the composition of the present invention.

In some other embodiments, the present invention provides a method for inhibiting a cyclooxygenase enzyme selected from cyclooxygenase-1 (COX-1) or cyclooxygenase-2 (COX-2), the method including contacting a cyclooxygenase enzyme with a compound of Formula I in an amount sufficient to inhibit cyclooxygenase, thereby inhibiting the cyclooxygenase enzyme. In some embodiments, the cyclooxygenase enzyme is COX-2. In some other embodiments, the amount is a therapeutically effective amount. In some embodiments, the COX-2 is inhibited without substantially inhibiting COX-1.

In some embodiments, the present invention provides a method for monitoring the activity of a soluble epoxide hydrolase, the method including contacting the soluble epoxide hydrolase with an amount of a compound of Formula I sufficient to produce a detectable change in the fluorescence of the soluble epoxide hydrolase by interacting with one or more tryptophan residues present in the catalytic site of said soluble epoxide hydrolase, thereby monitoring the activity of the soluble epoxide hydrolase.

The compounds provided herein can be assayed with respect to their ability to inhibit sEH. Additionally, the present invention provides assays and associated methods for monitoring soluble epoxide hydrolase activity, particularly the activity that has been modulated by the administration of one or more of the compounds provided above.

In some embodiments, the present invention provides methods for reducing the formation of a biologically active diol produced by the action of a soluble epoxide hydrolase, the method includes contacting the soluble epoxide hydrolase with an amount of a compound of the present invention, sufficient to inhibit the activity of the soluble epoxide hydrolase and reduce the formation of the biologically active diol. In some other embodiments, the present invention provides methods for stabilizing biologically active epoxides in the presence of a soluble epoxide hydrolase, the method including contacting the soluble epoxide hydrolase with an amount of a compound of the present invention, sufficient to inhibit the activity of the soluble epoxide hydrolase and stabilize the biologically active epoxide. The methods can be carried out as part of an in vitro assay or the methods can be carried out in vivo by monitoring blood titers of the respective biologically active epoxide or diol.

Epoxides and diols of some fatty acids are biologically important chemical mediators and are involved in several biological processes. Epoxy lipids are anti-inflammatory and anti-hypertensive. Additionally, the lipids are thought to be metabolized by beta-oxidation, as well as by epoxide hydration. Soluble epoxide hydrolase is considered to be the major enzyme involved in the hydrolytic metabolism of these oxylipins. The compounds of the present invention can inhibit soluble epoxide hydrolase and stabilize the epoxy lipids both in vitro and in vivo. This activity results in a reduction of hypertension in four separate rodent models. Moreover, the inhibitors show a reduction in renal inflammation associated with, and independent of, the hypertensive models.

The present invention also provides methods for monitoring a variety of lipids in both the arachidonate and linoleate cascade simultaneously in order to address the biology of the system. A GLC-MS system or a LC-MS method can be used to monitor over 740 analytes in a highly quantitative fashion in a single injection. The analytes include the regioisomers of the arachidonate epoxides (EETs), the diols (DHETs), as well as other P450 products including HETEs. Characteristic products of the cyclooxygenase, lipoxygenase, and peroxidase pathways in both the arachidonate and linoleate series can also be monitored. Such methods are particularly useful as being predictive of certain disease states. The oxylipins can be monitored in mammals following the administration of inhibitors of epoxide hydrolase. Generally, EH inhibitors increase epoxy lipid concentrations at the expense of diol concentrations in body fluids and tissues.

sEH inhibition $IC_{50}$ values for the compounds presented herein can be assayed by a recombinant affinity assay using purified sEHs, from human, mouse or rat, in a fluorescent-based assay. In such an assay, enzymes, e.g., ~1 nM human sEH, are incubated with a potential inhibitors for 5 min in 25 mM Bis-Tris/HCl buffer (200 µL; pH 7.0) at 30° C. before a substrate, e.g., cyano(2-methoxynaphthalen-6-yl)methyl trans-(3-phenyl-oxyran-2-yl)methyl carbonate, (CMNPC) is added ($[S]_{final}$=5 µM). Activity is assessed by measuring the appearance of the fluorescent 6-methoxynaphthaldehyde product ($\lambda_{em.}$=330 nm, $\lambda_{ex.}$=465 nm) at 30° C. during a 10 min incubation (Spectramax M2; Molecular Device, Inc., Sunnyvale, Calif.). The $IC_{50}$ values represent the concentration of the inhibitors which reduces the activity by 50%.

A COX Fluorescent Inhibitor Screening Assay Kit (catalog number 700100, Cayman Chemical, Ann Arbor, Mich.) is useful for assaying the ability of the compounds provided herein to inhibit ovine COX-1 and human recombinant COX-2 (% inhibition at 100 µM and $IC_{50}$ values (µM), respectively). Stock solutions of test compounds are dissolved in a minimum volume of DMSO. 10 µl of various concentrations of the test compound solutions, e.g., $[I]_{final}$ between 0.01 and 100 µM, are added to a series of supplied reaction buffer solutions (150 µl, 100 mM Tris-HCl, pH 8.0) with either COX-1 or COX-2 (10 µl) enzyme in the presence of Heme (10 µl) and a fluorometric substrate (10 µl). The reactions are initiated by quickly adding 10 µl of arachidonic acid solution and then incubating the system for two minutes at room temperature. Fluorescence of resorufin, which is produced by the reaction between $PGG_2$ and fluorometric substrate, ADHP (10-acetyl-3,7-dihydroxyphenoxazine), is analyzed with an excitation wavelength of 535 nm and an emission wavelength of 590 nm. The intensity of this fluorescence is proportional to the amount of resorufin, which is proportional to the amount of $PGG_2$ present in the well during the incubation. Percent inhibition is calculated by comparison from the 100% initial activity sample value (no inhibitor). Inhibitory Activities of compounds 7, 11a-h, and 21a-j are presented below in Table 2.

Using the Von Frey mechanical nociceptive assay, the ability of the compounds provided herein to reduce pain can be assayed. See Example 25 below for a description and the results of this assay.

Inhibition of COX and sEH Activities.

Known COX-2 selective inhibitors, e.g., Celecoxib, Rofecoxib, and Indomethacin, as well as a known sEH inhibitor, e.g., t-AUCB, were evaluated for their cross activities against the enzymes, COX-2, COX-1, and sEH. As illustrated in Table 1, selected reference inhibitors showed selective inhibitory activity against each targeted enzyme.

Prior attempts to conjugate two known pharmacophores proved challenging with respect to the effectiveness of the COX-2 inhibition and the sEH inhibition. In contrast, replacement of the adamantyl group of compound 11a with a cycloheptyl group, e.g., compound 11b, improves sEH inhibition by 10-fold. It was found that the aryl group, e.g. R$_3$ groups in compounds 11c-f, especially when substituted with a substituent at the para- or meta-positions, showed beneficial sEH inhibition. The trifluoromethoxy group at the para-position in compound 11d provided the unexpected result of slight COX-2 inhibition with moderate sEH inhibition. However, a trifluoromethyl group at the para-position not only decreases COX-2 inhibition but also, unexpectedly, decreases sEH inhibition by about 20-fold. Because, in general, sulfonamides may have an improved affinity for the COX-2 active site compared with sulfones, compound 11f, which includes a methylsulfone group, and compound 11g, which includes an aminosulfone group, were prepared. Compound 11g demonstrated a 2-fold more potent activity than the reference drug, e.g., Rofecoxib (COX-2 IC$_{50}$=2 μM). However, the sEH inhibition (sEH IC$_{50}$=84±6 nM) was comparable to compound 11f (sEH IC$_{50}$=72±8 nM). The inclusion of a tert-butyl group in compound 11h was observed to increase sEH inhibition (sEH IC$_{50}$=32±13 nM). However, this same change was observed to reduce the compound's COX-2 inhibitory activity.

In order to identify compounds with reduced steric hindrance and improved sEH inhibitory activity, a series of compounds were prepared wherein the linker between the diarylpyrazole group and the urea group was varied. Compound 7, in which a biarylpyrazole ring and a urea group are directly connected, demonstrated non-optimal sEH inhibitory activity (88±5 nM), similar to compound 11g (84±6 nM). Compounds that included two-carbon methylene linkers between the two pharmacophores, e.g., compound 15 (26±3 nM), improved sEH inhibition 3-fold compared to that of compound 11g (84±6 nM). However compound 21b (4.1±0.4 nM), which includes a three-carbon methylene linker between the COX-2 pharmacophore and the sEH pharmacophore, demonstrated improved sEH inhibition which was 20-fold compared to compound 11g (84±6 nM).

A series of COX-2/sEH dual inhibitors which include a three-carbon methylene linker between the two pharmacophores were synthesized and their structure-activity relationship (SAR) was studied. The results provided herein demonstrate that a pharmacophoric grouping of biarypyrazole, i.e., the COX-2 part, and urea, i.e., the sEH part, can improve the inhibitory activity of a molecule with respect to both COX-2 and sEH in vitro and in vivo. In addition, the COX-2/sEH dual inhibitor, compound 21i, not only showed a better in vivo efficacy in a pain model in rats compared to celecoxib and t-AUCB combination therapy, but may also demonstrate a superior safety profile compared to that of the combination therapy. Compound 21b, which has an aminosulfone group, was observed to be more potent than compound 21a, which has a methylsulfone group, with regard to COX-2 inhibition (COX-2 IC$_{50}$=3 μM, sEH IC$_{50}$=3.4±0.2 nM), while sEH inhibition remained the same. Compound 21c, which has methyl group at the para-position on the phenyl group at C-5 on the pyrazole ring, (COX-2 IC$_{50}$=2.8 sEH IC$_{50}$=10±1 nM), demonstrated a 3-fold diminished activity with respect to both COX-2 and sEH inhibition compared to compound 21b, (COX-2 IC$_{50}$=0.71 sEH IC$_{50}$=4.1±0.4 nM). Compound 21d, which includes two sterically hindered ortho-methyl groups close to a urea group, demonstrated non-optimal sEH inhibition. Other compounds provided herein demonstrate that relatively bulky carbocyclic group substituted at the meta- or para-positions of the phenyl group increase the inhibitory activity of sEH inhibitors. Compounds 21f (COX-2 IC$_{50}$=7 μM, sEH IC$_{50}$=0.5±0.1 nM) demonstrated potent inhibitory activity compared to t-AUCB (sEH IC$_{50}$=0.5±0.1 nM).

In order to optimize sEH inhibition activity, compounds possessing bulky groups, e.g., the carbocyclic group in compounds 21f and 21g or the para-substituted phenyl group in compounds 21j, 21i, and 21h, were prepared. Compounds 21f-j, which include carbocyclic or para-substituted phenyl groups, inhibited sEH at picomolar concentrations. In addition, compounds 21a-d, 21g, 21i, and 21j also demonstrated beneficial potency against COX-2. Compounds 21g, 21i (COX-2 IC$_{50}$=1.26 μM, sEH IC$_{50}$=0.9±0.1 nM), and 21j (COX-2 IC$_{50}$=0.92 μM, sEH IC$_{50}$=0.5±0.1 nM), which include, respectively, a relatively flexible cycloheptyl group, a para-substituted phenyl group, e.g. trifluoromethyl, and a trifluoromethoxy group, maintained COX-2 inhibitory activity and sEH inhibitory potency. Compounds that included a CF$_3$ group, e.g., compounds 21b, 21j, and 21i demonstrated superior COX-2 inhibition. Compounds 21b, 21j, and 21i showed IC$_{50}$ values superior to Rofecoxib for COX-2. Compounds 21b, 21j, and 21i also showed beneficial sEH inhibition and COX-1/COX-2 selectivity. The potency of these compounds was observed to be comparable with celecoxib against 5-LOX.

Figure 2:
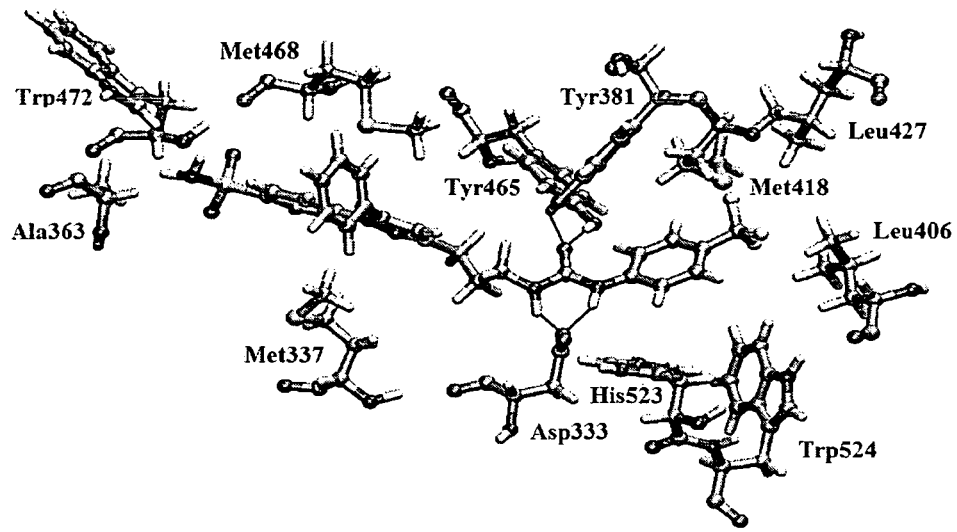
FIG. 2 shows compound 21i docked into (a) the co-crystal structure of human soluble epoxide hydrolase and (b) the co-crystal structure of murine COX-2. Black lines indicate possible hydrogen bonds.
Figure 2:
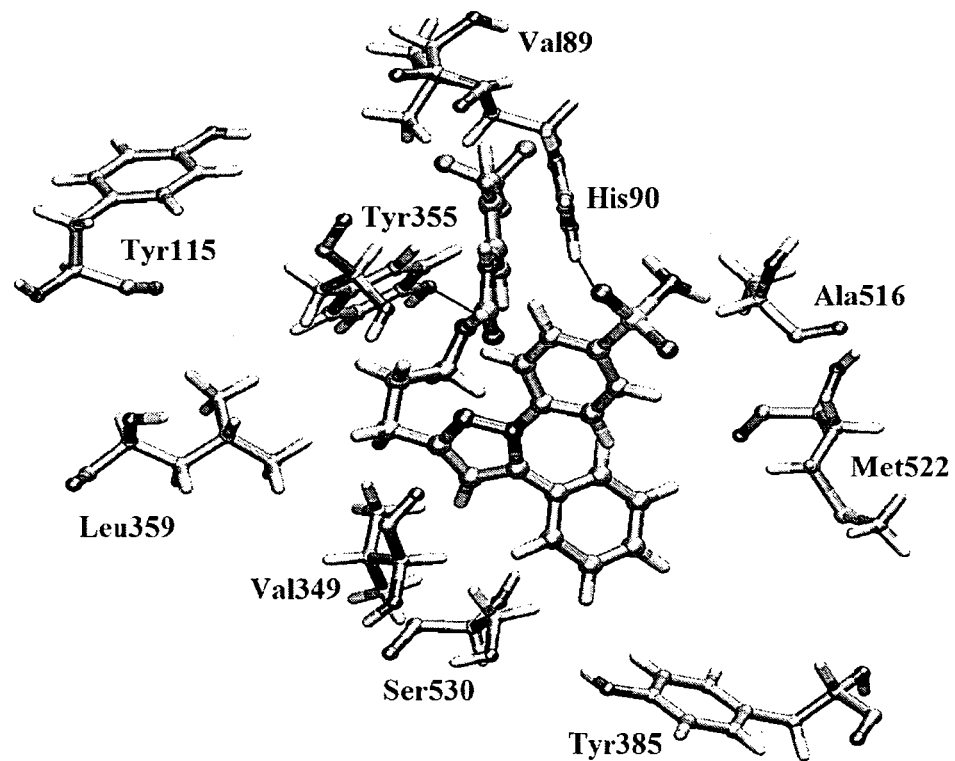

As seen in FIG. 2A, compound 21i was bound primarily through interactions with Tyr$^{387}$, Tyr$^{465}$ and Asp$^{333}$ with the urea pharmacophore. Also, one of the oxygen atoms in the sulfonamide group of compound 16i forms a hydrogen bond to His$^{90}$ as is the case for celecoxib. One of NH group in the urea of compound 21i may form hydrogen bonds with Tyr$^{355}$. The extra H-bonding possible in compound 21i may explain the increased activity of this compound, which include a three-carbon methylene linker, due to the sufficient space provide for the urea group to interact with the corresponding residue.

The pharmacokinetic (PK) properties of the compounds provided herein, e.g., compounds 21b, e-j, were assayed in vivo in mice using oral cassette dosing. As illustrated in Table 2, compounds 21i and 21j showed beneficial PK profiles, in particular the C$_{max}$ and AUC values. Compound 21b demonstrated similar inhibitory activities compared to compounds 21i and 21j, which showed a 15-fold lower C$_{max}$ and 8-fold lower AUC, respectively, in comparison, see Table 2.

The pharmacokinetic (PK) properties of the compounds provided herein, e.g., compounds 21i and 21j, were assayed in vivo in rats, see Table 2. In comparison, compound 21i showed a superior PK profile in rats with a 2-fold higher C$_{max}$ and AUC. Therefore, compound 21i was selected for in vivo study to determine its anti-nociceptive activity in a model of pain, see Example 25.

Figure 3:
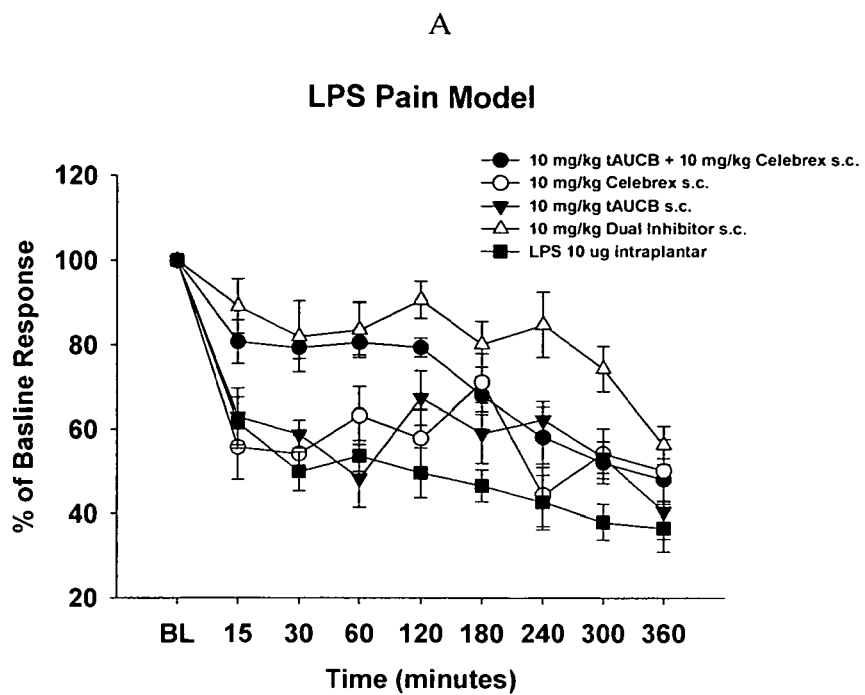
FIG. 3 shows results of the von Frey mechanical nociceptive assay (n=6 male Sprague Dawley Rats per group, inhibitors pretreated 60 minutes before LPS and tested until 6 hours post LPS injection). The sEH inhibitor t-AUCB or COX-2 selective inhibitor celecoxib alone has a limited effect. However, coadministration of both inhibitors increases the ability of the inhibitors to reduce pain. Compound 21i is more efficient than the combination of celecoxib with t-AUCB in LPS pain model in rats. (LPS: 10 mg/rat hindpaw intraplantar injection, t-AUCB: 10 mg/kg bw s.c., Celecoxib: 10 mg/kg s.c. Celecoxib+t-AUCB: Celecoxib 10 mg/kg s.c. and t-AUCB 10 mg/kg both separate s.c., 21i: 10 mg/kg bw s.c.)
Figure 3:
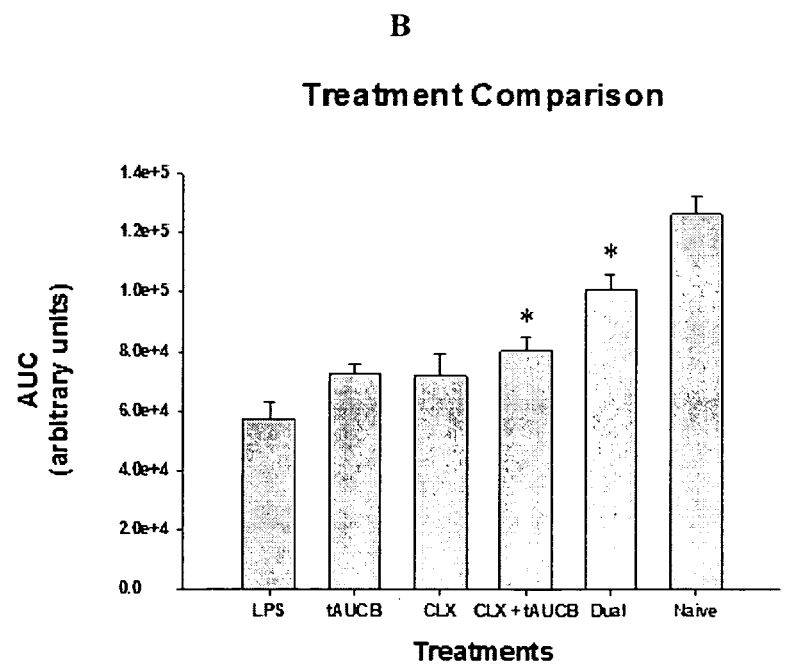

In vivo anti-allodynic effects of the COX-2/sEH dual inhibitors provided herein was assayed. An LPS induced model of inflammatory pain was used to compare the pain reducing activity of the COX-2/sEH dual inhibitors to combination and individual therapies. Specifically, a von Frey mechanical nociceptive assay was used to measure allodynia induced by LPS and the attenuation of this pain by coxibs and sEHI, see FIG. 3. Provided below is a comparison of the dual inhibitor compound 21i, a combination dose of celecoxib and t-AUCB, and individual doses of celecoxib and also t-AUCB. Male SD Rats (n=6) injected with LPS (10 μg per rat; intraplantar) developed allodynia which was indicated by a decrease in paw withdrawal latency to a non-noxious mechanical stimulus. Post LPS challenge, the average latency for hindpaw withdrawal dropped to 53.6±3.7% (SEM) within 60 minutes and remained at or below this score compared to vehicle controls which do not vary significantly from 100% for the entire six hour time-course. Prophylactic subcutaneous administration of the dual inhibitor compound 21i (10 mg/kg), a combination dose of celecoxib and t-AUCB (10 mg/kg, respectively), an individual dose of celecoxib (10 mg/kg), and an individual dose of t-AUCB (10 mg/kg) showed anti-allodynic effects, see FIG. 3. While t-AUCB or celecoxib exerted slight antihyperalgesic effect, both the dual inhibitor compound 21i and the coadministered dose of celecoxib and t-AUCB demonstrated synergistic effects with regard to reducing allodynia. Compound 21i also demonstrates a superior effect compared to the combination therapies, which suggests that the dual inhibitor may compensate for different pharmacokinetic properties of the individually co-administered compounds.

Based on the foregoing, compounds 21b, 21i and 21j demonstrate potent and selective inhibitory activity of COX-2 ($IC_{50}$=0.71, 1.26, and 0.92 µM, respectively) over COX-1 ($IC_{50}$>100 µM) and sEH ($IC_{50}$=4.1, 0.9, and 0.5 nM, respectively). Following subcutaneous administration of 10 mg/kg of compound 21i, this compound exhibited superior anti-allodynic activity as compared to the same dose of celecoxib, i.e., a COX-2 inhibitor, also as compared to the same dose of t-AUCB, i.e., a sEH inhibitor, and also as compared to the co-administered same dose of both celecoxib and t-AUCB. Accordingly, the dual inhibitors of the present invention demonstrate enhanced in vivo anti-allodynic activity in a nociceptive behavioral assay.

VI. Method of Inhibiting Cell Proliferation

In some embodiments, the present invention provides a method of inhibiting cell proliferation, including contacting a cell with an effective amount of a compound of Formula I, thereby inhibiting cell proliferation. Any suitable cells can be inhibited using the compounds of the present invention, including, but not limited to cancer cells derived from any tissue, pre-cancerous, pre-transformed, dysplastic or other abnormal cells, hepatocytes, epithelial cells, and blood vessel cells such as smooth muscle, fibroblasts, and endothelial cells. In some embodiments, the cancer cell is a cell selected from the cancers described herein. In some embodiments the endothelial cell can be from an artery, a vein, or the microvasculature (e.g., capillaries, arterioles and venules). In some embodiments the endothelial cell can be an umbilical artery endothelial cell (e.g., a human umbilical artery endothelial cell HUAEC) or an umbilical vein endothelial cell. In some embodiments, the cell can be a human umbilical vein endothelial cell (HUVEC).

In some embodiments, the present invention provides a method of reducing or inhibiting angiogenesis in a tissue, including contacting the tissue with an effective amount of a compound of Formula I, thereby reducing or inhibiting angiogenesis in the tissue. In some embodiments, the method reduces or inhibits angiogenesis in normal or healthy tissues. In some embodiments, the method reduces or inhibits angiogenesis in tumor or cancer tissues. In some embodiments, the methods reduce or inhibit growth factor (such as VEGF)-induced angiogenesis. In some embodiments, the methods reduce or inhibit angiogenesis by inhibiting endothelial tube formation.

In some other embodiments, the present invention provides a method of treating cancer, the method including administering to a subject in need thereof, a therapeutically effective amount of a compound of Formula I, thereby treating cancer.

In some embodiments, the present invention provides a method of treating cancer, the method including contacting cancer cells with a therapeutically effective amount of a compound of Formula I, thereby treating cancer. In some other embodiments, the contacting is performed in vitro.

In some embodiments, the cancer is selected from AIDS-related cancer, anal cancer, appendix cancer, bladder cancer, brain cancer, breast cancer, bronchial cancer, cervical cancer, colon cancer, endometrial cancer, esophageal cancer, intraocular melanoma, intestinal cancer, glioma, hairy cell lymphoma, head and neck cancer, hepatoma, Hodkin lung cancer, lymphoma, kaposi sarcoma, kidney cancer, leukemia, melanoma, metastatic squamous neck cancer, mouth cancer, multiple myeloma, nasopharengael cancer, neuroblastoma, non-small cell lung cancer, Non-Hodkin lymphoma, oral cancer, oropharyngeal cancer, osteosarcoma, ovarian cancer, pancreatic cancer, papillomatosis, paranasal sinus and nasal cavity cancer, penile cancer, pharyngeal cancer, pituitary tumor, plasma cell neoplasm, pleuropulmonary blastoma, primary central nervous system (CNS) lymphoma, prostate cancer, rectal cancer, renal cell (kidney) cancer, renal pelvis cancer, respiratory tract cancer, retinoblastoma, salivary gland cancer, sarcoma, skin cancer, small cell lung cancer, small intestine cancer, soft tissue sarcoma, squamous cell carcinoma, squamous neck cancer, stomach (gastric) cancer, t-cell lymphoma, testicular cancer, throat cancer, thymoma and thymic carcinoma, thyroid cancer, trophoblastic tumor, urethral cancer, uterine cancer, vaginal cancer, and vulvar cancer.

In some embodiments, the cancer is selected from lung carcinoma, melanoma, glioblastoma, prostate cancer, liver cancer, kidney cancer, or colon cancer.

In some other embodiments, the cancer is selected from lewis lung carcinoma, V6S10 melanoma, human H-1 melanoma, human A375 primary melanoma, UAD7 glioblastoma, human PC3 prostate cancer, DU145 prostate cancer, and CL188 colon cancer.

In some embodiments, the compounds and compositions of the present invention are suitable for treating solid tumors and tumors which are also treatable with coxibs. In some other embodiments, the sEH inhibitors of the present invention may reduce the thrombic side effects of high doses of coxibs. In some embodiments, the sEH inhibitors of the present invention may also improve the efficacy of the coxibs.

VII. Examples

General.

All reagents and solvents were obtained from commercial suppliers and were used without further purification. All reactions, unless otherwise described, were performed under an inert atmosphere of dry nitrogen. Melting points were determined on an OptiMelt melting point apparatus and are uncorrected. $^{1}H$ NMR and $^{13}C$ NMR spectra were recorded at 300 and 75 MHz, respectively. Elemental analyses were determined at Midwest Microlab, Indianapolis, Ind. Mass spectra were measured by LC-MS equipped with a Waters 2790 and a Waters PDA 996 using electrospray (+) ionization. Flash chromatography was performed on silica gel.

Example 1

Preparation of 4-{5-Phenyl-3-[3-(3-trifluoromethyl-phenyl)-ureido]-pyrazol-1-yl}-benzenesulfonamide (7)

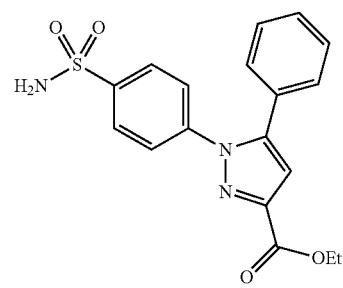 [SMILES: CCOC(=O)c1cc(-c2ccccc2)n(-c2ccc(S(N)(=O)=O)cc2)n1]

5-Phenyl-1-(4-sulfamoyl-phenyl)-1H-pyrazole-3-carboxylic acid ethyl ester (3b). To a solution of potassium bis(trimethylsilyl)amide (8.88 g, 44.5 mmol) in 400 mL of THF was added dropwise acetophenone (4.85 mL, 41.6 mmol) at 78° C. After 1 hour, diethyl oxalate (6.2 mL, 45.8 mmol) was added dropwise at the same temperature. The reaction mixture was allowed to warm up to room temperature and stirred overnight. The solvent was removed in vacuo.

The resulting yellowish solid was filtered and washed with Et₂O to give the title compound 2 (10.5 g, 98%) as a sodium salt of Ethyl 2-hydroxy-4-oxo-4-phenyl-2-butenoate (2). To a solution of sodium salt of 2 in EtOH (300 mL) was added 4-amidosulfonylphenylhydrazine 1b (10 g, 44.7 mmol) at room temperature. The reaction mixture was stirred for 1 hour and then 2.4 mL of AcOH was added. The reaction mixture was refluxed for 2 hours. After cooling, the solvent was removed in vacuo. The resulting solid was purified by recrystallization with MeOH to afford the titled compound (13.5 g, 89% yield) as a white solid. mp 191.5-194.6° C. ¹H NMR (300 MHz, DMSO-d₆): δ 7.87 (d, J=8 Hz, 2H), 7.58-7.48 (m, 4H), 7.44-7.38 (m, 3H), 7.34-7.27 (m, 2H), 7.16 (s, 1H), 4.35 (q, J=7 Hz, 2H), 1.32 (t, J=7 Hz, 3H).

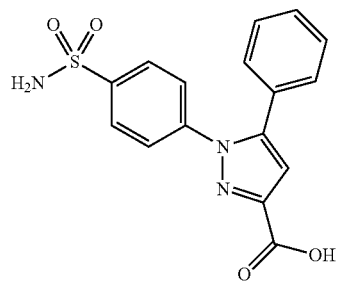 [SMILES: NS(=O)(=O)c1ccc(-n2nc(C(=O)O)cc2-c2ccccc2)cc1]

5-Phenyl-1-(4-sulfamoyl-phenyl)-1H-pyrazole-3-carboxylic acid (4). To a solution of compound 3b (0.37 g, 1 mmol) in THF (10 mL) was added LiOH (35 mg, 1.5 mmol) followed by 2 mL of water at room temperature. The reaction mixture was stirred overnight. The reaction was quenched by adding 1N HCl. The solvent was evaporated in vacuo. The resulting white solids were collected by suction filtration and washed with water. The crude product was recrystallized from MeOH to give the titled compound (0.33 g, 96% yield) as a white solid. mp 188.5-190.9° C. ¹H NMR (300 MHz, DMSO-d₆): δ 13.10 (s, 1H), 7.87 (d, J=8 Hz, 2H), 7.55-7.48 (m, 4H), 7.44-7.37 (m, 3H), 7.34-7.26 (m, 2H), 7.10 (s, 1H).

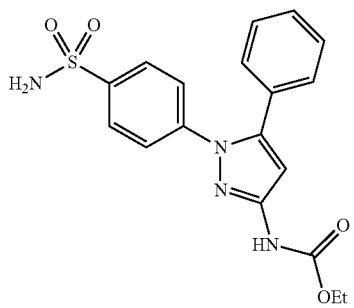 [SMILES: CCOC(=O)Nc1cc(-c2ccccc2)n(-c2ccc(S(N)(=O)=O)cc2)n1]

[5-Phenyl-1-(4-sulfamoyl-phenyl)-1H-pyrazol-3-yl]-carbamic acid ethyl ester (5). To a solution of acid 4 (0.74 g, 2 mmol) in 10 mL of EtOH and 10 mL of 1,4-dioxane was added diphenylphosphonylazide (0.52 mL, 2.4 mmol) followed by Et₃N (0.34 mL, 2.4 mmol). The reaction mixture was refluxed overnight. After cooling the reaction mixture to room temperature, EtOAc and water were added. The organic layer was separated, washed with brine, dried over MgSO₄ and concentrated in vacuo. The residue was purified by column chromatography to give the titled compound (0.48 g, 62%) as a white solid. mp 120.9-127.5° C. ¹H NMR (300 MHz, DMSO-d₆): δ 10.30 (s, 1H), 7.79 (d, J=8 Hz, 2H), 7.50-7.34 (m, 7H), 7.33-7.25 (m, 2H), 6.74 (s, 1H), 4.14 (q, J=7 Hz, 2H), 1.24 (t, J=7 Hz, 3H).

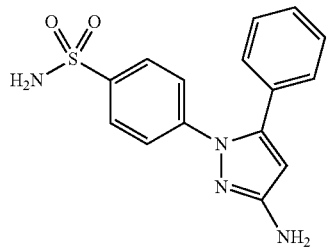 [SMILES: Nc1cc(-c2ccccc2)n(-c2ccc(S(N)(=O)=O)cc2)n1]

4-(3-Amino-5-phenyl-pyrazol-1-yl)-benzenesulfonamide (6). To a solution of an ethyl carbamate 5 (0.39 g, 1 mmol) in EtOH (10 mL) was added 10% NaOH solution (3.2 mL) at room temperature. The reaction mixture was refluxed for 5 hours. The reaction mixture was cooled to room temperature and water was added. The resulting white precipitate was filtered and washed with water thoroughly to give the titled compound (0.22 g, 70%) as a white solid. mp 286.3-290.2° C. ¹H NMR (DMSO-d₆): δ 7.70 (d, J=9 Hz, 2H), 7.43-7.20 (m, 9H), 5.89 (s, 1H), 5.17 (br s, 2H).

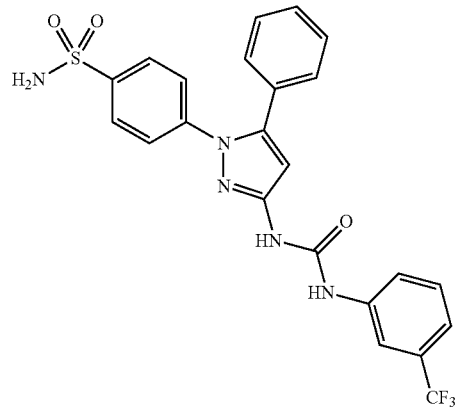 [SMILES: NS(=O)(=O)c1ccc(-n2nc(NC(=O)Nc3cccc(C(F)(F)F)c3)cc2-c2ccccc2)cc1]

4-{5-Phenyl-3-[3-(3-trifluoromethyl-phenyl)-ureido]-pyrazol-1-yl}-benzenesulfonamide (7). To a solution of amine 6 (0.1 g, 0.32 mmol) in 5 mL of DMF was added 3-(trifluoromethyl)phenyl isocyanate (0.12 g, 0.62 mmol) followed by triethylamine (0.05 mL, 0.32 mmol) at 0° C. The reaction mixture was warmed up to room temperature and stirred overnight. The reaction mixture was poured into water, and the resulting precipitates were collected and washed with water. The crude product was purified by column chromatography by dry loading method to give the titled compound (0.13 g, 81% yield). mp 195.1-197.0° C. ¹H NMR (300 MHz, DMSO-d₆): δ 9.48 (s, 1H), 9.21 (s, 1H), 8.07 (s, 1H), 7.80 (d, J=9 Hz, 2H), 7.61-7.26 (m, 12H), 6.81 (s, 1H). MS (ESI) m/z: 502.12 (M+H⁺). Anal. Calcd for C₂₃H₁₈F₃N₅O₃S.0.36CH₄O: C, 54.69; H, 3.82; N, 13.65. Found: C, 54.69; H, 3.70; N, 13.44.

Example 2

Preparation of 1-Adamantan-1-yl-3-[1-(4-methanesulfonyl-phenyl)-5-phenyl-1H-pyrazol-3-ylmethyl]-urea (11a)

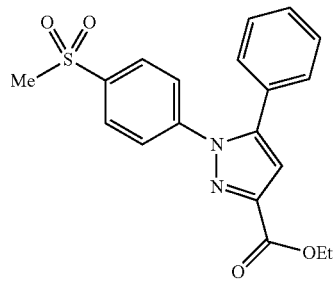 [SMILES: CCOC(=O)c1cc(-c2ccccc2)n(-c2ccc(S(C)(=O)=O)cc2)n1]

1-(4-Methanesulfonyl-phenyl)-5-phenyl-1H-pyrazole-3-carboxylic acid ethyl ester (3a). Compound 3a was synthesized in a manner similar to the synthesis of 3b using 4-(methylsulfonyl)phenylhydrazine hydrochloride (10 g, 44.7 mmol) to give 3a (13.6 g, 82% yield) as a white solid. mp 199.4-202.9° C. $^1$H NMR (300 MHz, DMSO-$d_6$): δ 7.99 (d, J=9 Hz, 2H), 7.58 (d, J=9 Hz, 2H), 7.43-7.38 (m, 3H), 7.34-7.27 (m, 2H), 7.17 (s, 1H), 4.34 (q, J=7, 2H), 3.27 (s, 3H), 1.31 (t, J=7, 3H).

General Procedure for the Synthesis of Hydroxymethylpyrazoles 8a and 8b. To a solution of compound 3a or 3b in THF was added LiAlH$_4$ (3.2 eq) at room temperature. The reaction mixture was stirred for 6 hours. EtOAC was added and excess LiAlH$_4$ was quenched by adding minimum amounts of water. The solution was dried with MgSO4 and white precipitates were filtered off. The filtrate was concentrated in vacuo. The crude product was purified by column chromatography (EtOAc/Hexanes in adequate proportions) to give the compound 8a or 8b.

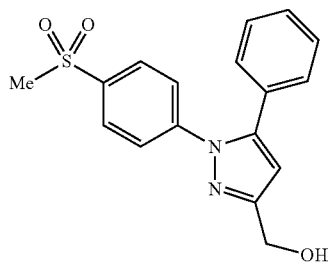 [SMILES: CS(=O)(=O)c1ccc(-n2nc(CO)cc2-c2ccccc2)cc1]

[1-(4-Methanesulfonyl-phenyl)-5-phenyl-1H-pyrazol-3-yl]-methanol (8a) was synthesized as a white solid (3.25 g, 76% yield) from the ester 3a (5 g, 17.1 mmol) by the general procedure for the synthesis of hydroxymethylpyrazoles 8a and 8b and purified by column chromatography with Hexanes/EtOAc (1:1). mp 126.5-128.5° C. $^1$H NMR (300 MHz, DMSO-$d_6$): δ 7.88 (d, J=9 Hz, 2H), 7.49 (d, J=9 Hz, 2H), 7.41-7.34 (m, 3H), 7.26-7.21 (m, 2H), 6.56 (s, 1H), 4.81 (d, J=6 Hz, 2H), 3.05 (s, 3H), 2.13 (t, J=6 Hz, 1H).

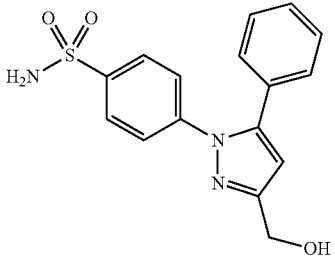 [SMILES: NS(=O)(=O)c1ccc(-n2nc(CO)cc2-c2ccccc2)cc1]

4-(3-Hydroxymethyl-5-phenyl-pyrazol-1-yl)-benzenesulfonamide (8b) was synthesized as a white solid (2.8 g, 75% yield) from ester 3b (4.18 g, 11.3 mmol) by the general procedure for the Synthesis of Hydroxymethylpyrazoles 8a and 8b and purified by column chromatography with Hexanes/EtOAc (4:6). mp 173.8-180.5° C. $^1$H NMR (300 MHz, DMSO-$d_6$): δ 7.81 (d, J=8 Hz, 2H), 7.50-7.35 (m, 7H), 7.30-7.23 (m, 2H), 6.64 (s, 1H), 5.28 (t, J=6 Hz, 1H), 4.53 (d, J=6 Hz, 2H).

General Procedure for the Synthesis of Azidomethylpyrazoles 9a and 9b.

To a solution of alcohol 8a or 8b in THF was added methanesulfonyl chloride (1.3 eq) followed by Et$_3$N (1.6 eq) at 0° C. The reaction mixture was stirred for 2 hours. After adding water, the product was extracted with EtOAc. The organic layer was dried with MgSO$_4$ and the solvent was removed in vacuo. To a solution of a mesylate obtained, in 1,4-dioxane/water (1:1) was added NaN$_3$ (2.5 eq). The reaction mixture was heated at 80° C. for 3 hours. After cooling, the solvent were removed in vacuo. The residue was purified by column chromatography (EtOAc/Hexanes in adequate proportions) to give the compound 9a or 9b.

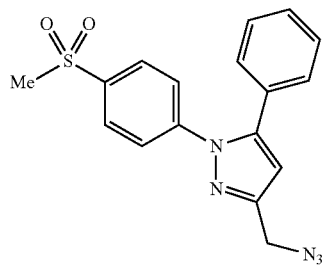 [SMILES: CS(=O)(=O)c1ccc(-n2nc(CN=[N+]=[N-])cc2-c2ccccc2)cc1]

3-Azidomethyl-1-(4-methanesulfonyl-phenyl)-5-phenyl-1H-pyrazole (9a) was synthesized as an white waxy solid (0.7 g, 99% yield) from alcohol 8a (0.5 g, 2 mmol) by the general procedure for the Synthesis of Azidomethylpyrazoles 9a and 9b and purified by column chromatography with Hexanes/EtOAc (6:4). $^1$H NMR (300 MHz, DMSO-$d_6$): δ 7.95 (d, J=9 Hz, 2H), 7.51 (d, J=9 Hz, 2H), 7.45-7.39 (m, 3H), 7.33-7.26 (m, 2H), 6.76 (s, 1H), 4.53 (s, 2H), 3.26 (s, 3H).

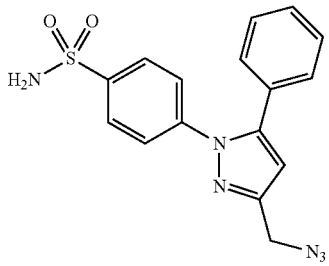 [SMILES: [N-]=[N+]=NCc1cc(-c2ccccc2)n(-c2ccc(S(N)(=O)=O)cc2)n1]

4-(3-Azidomethyl-5-phenyl-pyrazol-1-yl)-benzenesulfonamide (9b) was synthesized as a white waxy solid (0.48 g, 90% yield) from ester 8b (0.5 g, 1.52 mmol) by the general procedure for the synthesis of azidomethylpyrazoles 9a and 9b and purified by column chromatography with Hexanes/EtOAc (1:1). $^1$H NMR (300 MHz, DMSO-$d_6$): δ 7.83 (d, J=9 Hz, 2H), 7.51-7.37 (m, 7H), 7.31-7.24 (m, 2H), 6.75 (s, 1H), 4.53 (s, 2H).

General Procedure for the Synthesis of Azidomethylpyrazoles 10a and 10b.

To a solution of 9a or 9b in EtOAc was added 10% palladium on carbon. The solution was filled with H$_2$ and the reaction mixture was stirred for 2 hours. After the solution was filtered through Celite, the filtrate was concentrated in vacuo. The crude product was used for the next step without further purification.

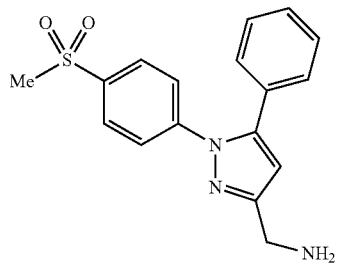 [SMILES: CS(=O)(=O)c1ccc(-n2nc(CN)cc2-c2ccccc2)cc1]

C-[1-(4-Methanesulfonyl-phenyl)-5-phenyl-1H-pyrazol-3-yl]-methylamine (10a). 91% yield. $^1$H NMR (300 MHz, CDCl$_3$): δ 7.87 (d, J=9 Hz, 2H), 7.48 (d, J=9 Hz, 2H), 7.40-7.32 (m, 3H), 7.26-7.19 (m, 2H), 6.48 (s, 1H), 3.97 (s, 2H), 3.04 (s, 3H), 1.65 (s, 2H).

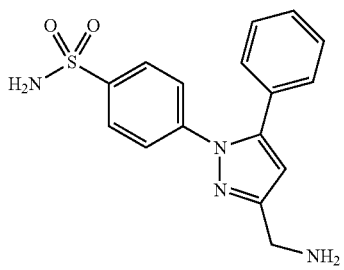 [SMILES: NCc1cc(-c2ccccc2)n(-c2ccc(S(N)(=O)=O)cc2)n1]

4-(3-Aminomethyl-5-phenyl-pyrazol-1-yl)-benzene-sulfonamide (10b). 90% yield.

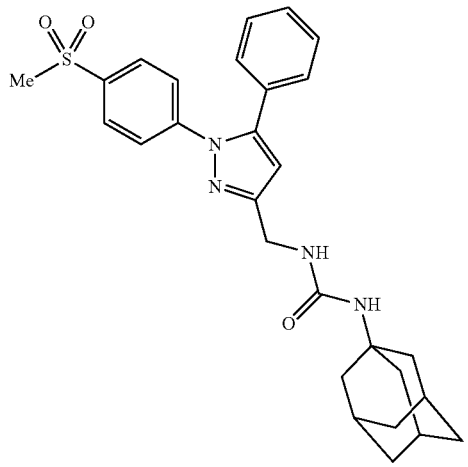 [SMILES: CS(=O)(=O)c1ccc(-n2nc(CNC(=O)NC34CC5CC(CC(C5)C3)C4)cc2-c2ccccc2)cc1]

1-Adamantan-1-yl-3-[1-(4-methanesulfonyl-phenyl)-5-phenyl-1H-pyrazol-3-ylmethyl]-urea (11a). The titled compound was prepared in 68% yield from 1-adamantyl isocyanate using the procedure detailed for compound 7. mp 150.0-155.3° C. $^1$H NMR (300 MHz, DMSO-d$_6$): δ 7.93 (d, J=9 Hz, 2H), 7.48 (d, J=9 Hz, 2H), 7.44-7.38 (m, 3H), 7.30-7.23 (m, 2H), 6.54 (s, 1H), 6.13 (t, J=6 Hz, 1H), 5.71 (s, 1H), 4.22 (d, J=6 Hz, 2H), 3.25 (s, 1H), 2.04-1.96 (m, 3H), 1.90-1.85 (m, 6H), 1.63-1.57 (m, 6H). MS (ESI) m/z: 505.22 (M+H$^+$). Anal. Calcd for C$_{28}$H$_{32}$N$_4$O$_3$S: C, 66.64; H, 6.39; N, 11.10. Found: C, 66.46; H, 6.31; N, 10.86.

Example 3

Preparation of 1-Cycloheptyl-3-[1-(4-methanesulfonyl-phenyl)-5-phenyl-1H-pyrazol-3-ylmethyl]-urea (11b)

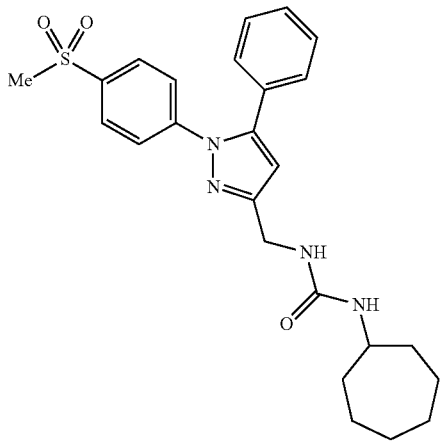 [SMILES: CS(=O)(=O)c1ccc(-n2nc(CNC(=O)NC3CCCCCC3)cc2-c2ccccc2)cc1]

1-Cycloheptyl-3-[1-(4-methanesulfonyl-phenyl)-5-phenyl-1H-pyrazol-3-ylmethyl]-urea (11b). The titled compound was prepared in 68% yield from cycloheptyl isocyanate using the procedure detailed for compound 7. mp 103.9-109.9° C. $^1$H NMR (300 MHz, DMSO-d$_6$): δ 7.93 (d, J=9 Hz, 2H), 7.48 (d, J=9 Hz, 2H), 7.44-7.38 (m, 3H), 7.29-7.24 (m, 2H), 6.54 (s, 1H), 6.18 (t, J=6 Hz, 1H), 5.94 (d, J=8 Hz, 1H), 4.26 (d, J=6 Hz, 2H), 3.66-3.54 (m, 1H), 3.25 (s, 3H), 1.82-1.70 (m, 2H), 1.61-1.29 (m, 10H). MS (ESI) m/z: 467.21 (M+H$^+$). Anal. Calcd for C$_{25}$H$_{30}$N$_4$O$_3$S.0.25CH$_4$O: C, 63.90; H, 6.58; N, 11.80. Found: C, 63.91; H, 6.42; N, 11.92.

Example 4

Preparation of 1-[1-(4-Methanesulfonyl-phenyl)-5-phenyl-1H-pyrazol-3-ylmethyl]-3-phenyl-urea (11c)

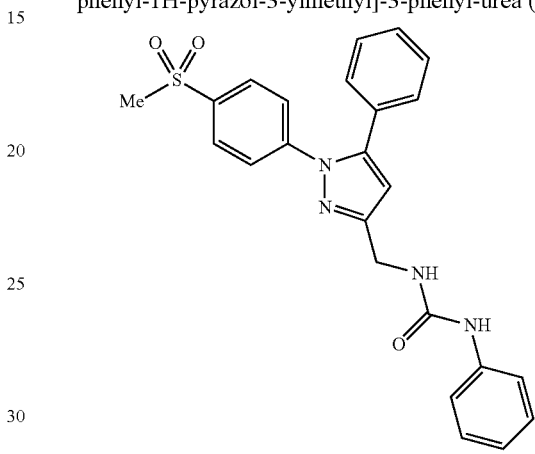

1-[1-(4-Methanesulfonyl-phenyl)-5-phenyl-1H-pyrazol-3-ylmethyl]-3-phenyl-urea (11c). The titled compound was prepared in 68% yield from phenyl isocyanate using the procedure detailed for compound 7. mp 95.7-104.2° C. $^1$H NMR (300 MHz, DMSO-d$_6$): δ 8.62 (s, 1H), 7.94 (d, J=9 Hz, 2H), 7.50 (d, J=9 Hz, 2H), 7.43-7.37 (m, 5H), 7.31-7.18 (m, 4H), 6.89 (t, J=7 Hz, 1H), 6.67-6.61 (m, 1H), 6.62 (s, 1H), 4.38 (d, J=6 Hz, 2H), 3.25 (s, 3H). MS (ESI) m/z: 447.15 (M+H$^+$). Anal. Calcd for C$_{24}$H$_{22}$N$_4$O$_3$S: C, 64.56; H, 4.97; N, 12.55. Found: C, 64.23; H, 5.07; N, 12.33.

Example 5

Preparation of 1-[1-(4-Methanesulfonyl-phenyl)-5-phenyl-1H-pyrazol-3-ylmethyl]-3-(4-trifluoromethoxy-phenyl)-urea (11d)

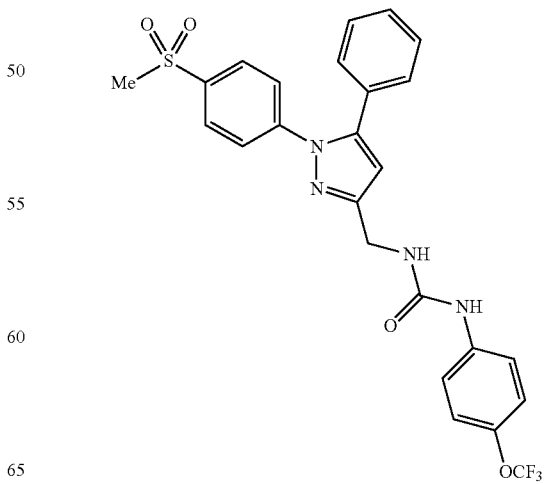

1-[1-(4-Methanesulfonyl-phenyl)-5-phenyl-1H-pyrazol-3-ylmethyl]-3-(4-trifluoromethoxy-phenyl)-urea (11d). The titled compound was prepared in 68% yield from 4-(trifluoromethoxy)phenyl isocyanate using the procedure detailed for compound 7. mp 152.9-156.3° C. $^1$H NMR (300 MHz, DMSO-d$_6$): δ 8.87 (s, 1H), 7.94 (d, J=9 Hz, 2H), 7.55-7.46 (m, 4H), 7.43-7.37 (m, 3H), 7.31-7.19 (m, 4H), 6.73 (t, J=6 Hz, 1H), 6.62 (s, 1H), 4.39 (d, J=6 Hz, 2H), 3.25 (s, 3H). MS (ESI) m/z: 531.13 (M+H$^+$). Anal. Calcd for C$_{25}$H$_{21}$F$_3$N$_4$O$_4$S: C, 56.60; H, 3.99; N, 10.56. Found: C, 56.42; H, 3.93; N, 10.35.

Example 6

Preparation of 1-[1-(4-Methanesulfonyl-phenyl)-5-phenyl-1H-pyrazol-3-ylmethyl]-3-(4-trifluoromethyl-phenyl)-urea (11e)

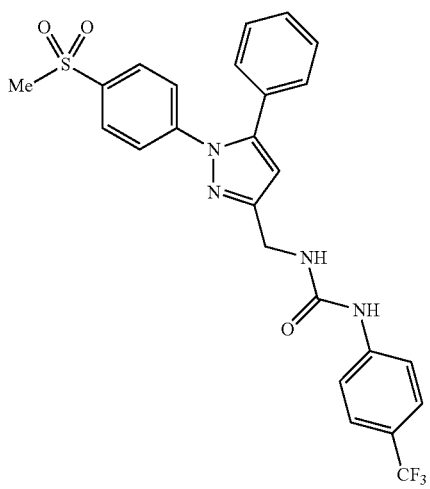 [SMILES: CS(=O)(=O)c1ccc(-n2nc(CNC(=O)Nc3ccc(C(F)(F)F)cc3)cc2-c2ccccc2)cc1]

1-[1-(4-Methanesulfonyl-phenyl)-5-phenyl-1H-pyrazol-3-ylmethyl]-3-(4-trifluoromethyl-phenyl)-urea (11e). The titled compound was prepared in 68% yield from 4-(trifluoromethyl)phenyl isocyanate using the procedure detailed for compound 7. mp 129.3-131.7° C. $^1$H NMR (300 MHz, DMSO-d$_6$): δ 9.09 (s, 1H), 7.94 (d, J=9 Hz, 2H), 7.65-7.54 (m, 4H), 7.50 (d, J=9 Hz, 2H), 7.43-7.38 (m, 3H), 7.31-7.25 (m, 2H), 6.83 (t, J=6 Hz, 1H), 6.64 (s, 1H), 4.41 (d, J=6 Hz, 2H), 3.25 (s, 3H). MS (ESI) m/z: 515.14 (M+H$^+$). Anal. Calcd for C$_{25}$H$_{21}$F$_3$N$_4$O$_3$S.0.375CH$_4$O: C, 57.88; H, 4.31; N, 10.64. Found: C, 57.88; H, 4.31; N, 10.36.

Example 7

Preparation of 1-[1-(4-Methanesulfonyl-phenyl)-5-phenyl-1H-pyrazol-3-ylmethyl]-3-(3-trifluoromethyl-phenyl)-urea (11f)

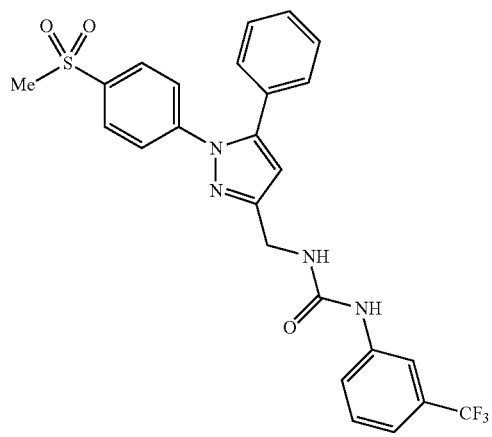 [SMILES: CS(=O)(=O)c1ccc(-n2nc(CNC(=O)Nc3cccc(C(F)(F)F)c3)cc2-c2ccccc2)cc1]

1-[1-(4-Methanesulfonyl-phenyl)-5-phenyl-1H-pyrazol-3-ylmethyl]-3-(3-trifluoromethyl-phenyl)-urea (11f). The titled compound was prepared in 68% yield from 3-(trifluoromethyl)phenyl isocyanate using the procedure detailed for compound 7. mp 107.5-113.0° C. $^1$H NMR (300 MHz, DMSO-d$_6$): δ 9.05 (s, 1H), 8.00 (s, 1H), 7.94 (d, J=9 Hz, 2H), 7.56-7.36 (m, 7H), 7.32-7.21 (m, 3H), 6.82 (t, J=6 Hz, 1H), 6.63 (s, 1H), 4.40 (d, J=6 Hz, 2H), 3.25 (s, 3H). MS (ESI) m/z: 515.13 (M+H$^+$).

Example 8

Preparation of 4-{5-Phenyl-3-[3-(3-trifluoromethyl-phenyl)-ureidomethyl]-pyrazol-1-yl}-benzenesulfonamide (11g)

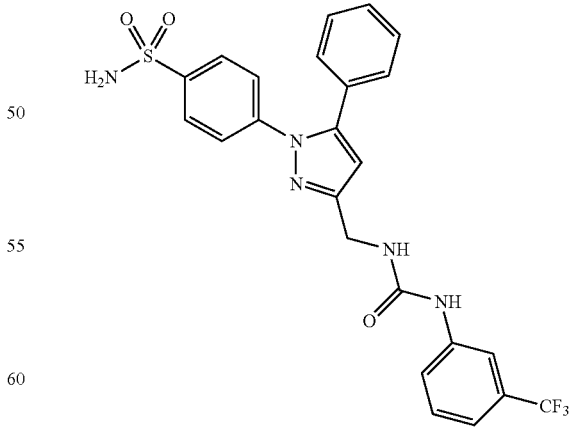

4-{5-Phenyl-3-[3-(3-trifluoromethyl-phenyl)-ureidomethyl]-pyrazol-1-yl}-benzenesulfonamide (11g). The titled compound was prepared in 68% yield from 3-(trifluoromethyl)phenyl isocyanate using the procedure detailed for compound 7. mp 184.6-189.6° C. $^1$H NMR (300 MHz, DMSO-d$_6$): δ 9.04 (s, 1H), 8.00 (s, 1H), 7.81 (d, J=9 Hz, 2H), 7.56-7.35 (m, 9H), 7.30-7.21 (m, 3H), 6.81 (t, J=6 Hz, 1H), 6.61 (s, 1H), 4.39 (d, J=6 Hz, 2H). MS (ESI) m/z: 516.13 (M+H$^+$).

Example 9

Preparation of 4-(5-Phenyl-3-{2-[3-(3-trifluoromethyl-phenyl)-ureido]-ethyl}-pyrazol-1-yl)-benzenesulfonamide (15)

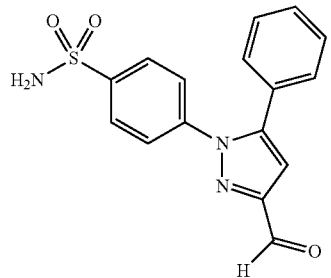 [SMILES: NS(=O)(=O)c1ccc(-n2nc(C=O)cc2-c2ccccc2)cc1]

4-(3-Formyl-5-phenyl-pyrazol-1-yl)-benzenesulfonamide (12b). To a solution of alcohol 8b (3 g, 9.1 mmol) and 3 g of powdered 4 Å molecular sieves in 150 mL of DCM, was added PCC (2.94 g, 13.7 mmol) at room temperature. After 6 hours, the reaction mixture was filtered through a 0.75-in. pad of Celite. The filtrate was concentrated in vacuo then the residue was purified by column chromatography to afford the titled compound (2.1 g, 70%) as a white solid. mp 177.3-179.8° C. $^1$H NMR (300 MHz, DMSO-d$_6$): δ 10.03 (s, 1H), 7.88 (d, J=8 Hz, 2H), 7.61-7.49 (m, 4H), 7.48-7.37 (m, 3H), 7.35-7.26 (m, 2H), 7.20 (s, 1H).

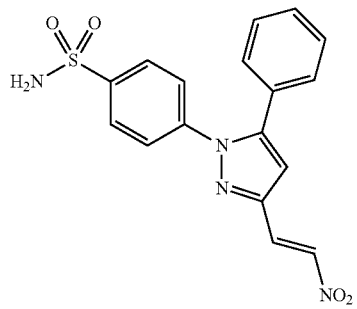 [SMILES: NS(=O)(=O)c1ccc(-n2nc(/C=C/[N+](=O)[O-])cc2-c2ccccc2)cc1]

4-[3-((E)-2-Nitro-vinyl)-5-phenyl-pyrazol-1-yl]-benzenesulfonamide (13). To a solution of aldehyde 10 (0.96 g, 2.9 mmol) in MeNO$_2$ (5.9 mL, 109 mmol) was added AcONH$_4$ (0.34 g, 4.4 mmol). The reaction mixture was refluxed for 1 hours. After cooling, MeNO$_2$ was evaporated in vacuo. The residue was purified by column chromatography with Hexanes/EtOAc (7:3) to give the corresponding nitroethylene compound (0.5 g, 46%) as a yellow solid. mp 189.2-191.8° C. $^1$H NMR (300 MHz, DMSO-d$_6$): δ 8.24 (d, J=14 Hz, 1H), 8.01 (d, J=14 Hz, 1H), 7.85 (d, J=9 Hz, 2H), 7.54-7.47 (m, 4H), 7.46-7.40 (m, 3H), 7.37 (s, 1H), 7.32-7.26 (m, 2H).

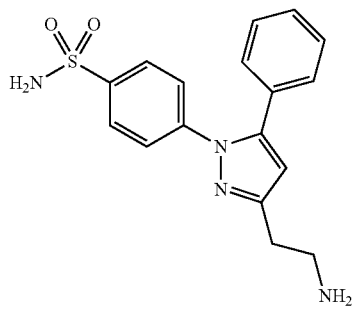 [SMILES: NCCc1cc(-c2ccccc2)n(-c2ccc(S(N)(=O)=O)cc2)n1]

4-[3-(2-Amino-ethyl)-5-phenyl-pyrazol-1-yl]-benzenesulfonamide (14). To a solution of the compound above (0.42 g, 1.1 mmol) in 10 ml of THF was added LiAlH$_4$ (0.21 g, 5.7 mmol) at room temperature. The reaction mixture was stirred for 6 hours and quenched by adding water (10 mL). The mixture was extracted with EtOAc and the combined organic layers were dried with MgSO4. The solution was evaporated in vacuo. The crude product was used next step without further purification (0.3 g, 77% yield). mp 189.2-191.8° C. $^1$H NMR (300 MHz, DMSO-d$_6$): δ 7.79 (d, J=9 Hz, 2H), 7.43-7.36 (m, 5H), 7.28-7.23 (m, 2H), 6.55 (s, 1H), 5.23-3.88 (m, 4H), 2.88 (t, J=7 Hz, 2H), 2.71 (t, J=7 Hz, 2H).

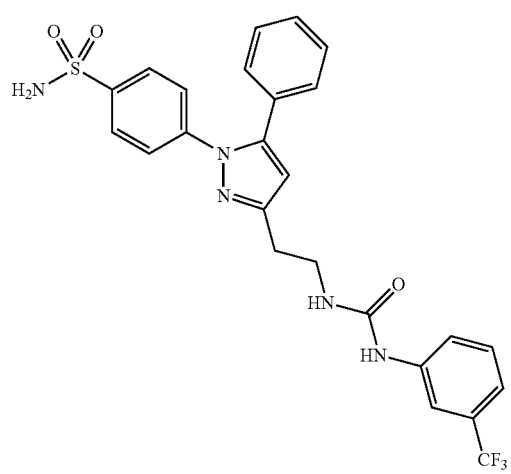 [SMILES: NS(=O)(=O)c1ccc(-n2nc(CCNC(=O)Nc3cccc(C(F)(F)F)c3)cc2-c2ccccc2)cc1]

4-(5-Phenyl-3-{2-[3-(3-trifluoromethyl-phenyl)-ureido]-ethyl}-pyrazol-1-yl)-benzenesulfonamide (15). The titled compound was prepared in 84% yield from 3-trifluoromethylphenyl isocyanate using the procedure detailed for compound 7. mp 121.9-124.7° C. $^1$H NMR (300 MHz, DMSO-d$_6$): δ 8.97 (s, 1H), 8.00 (s, 1H), 7.80 (d, J=8 Hz, 2H), 7.52-7.36 (m, 8H), 7.29-7.20 (m, 4H), 6.61 (s, 1H), 6.41 (t, J=6 Hz, 1H), 3.49 (dd, J=13 and 7 Hz, 2H), 2.85 (t, J=7 Hz, 2H). MS (ESI) m/z: 530.15 (M+H$^+$).

Example 10

Preparation of 1-{3-[1-(4-Methanesulfonyl-phenyl)-5-phenyl-1H-pyrazol-3-yl]-propyl}-3-(3-trifluoromethyl-phenyl)-urea (21a)

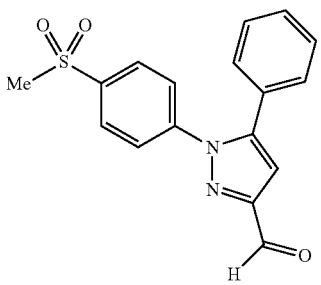 [SMILES: CS(=O)(=O)c1ccc(-n2nc(C=O)cc2-c2ccccc2)cc1]

1-(4-Methanesulfonyl-phenyl)-5-phenyl-1H-pyrazole-3-carbaldehyde (12a). The titled compound was prepared in 65% yield from the compound 3a using the procedure detailed for compound 12b. mp 133.0-135.5° C. $^1$H NMR (300 MHz, DMSO-d$_6$): δ 10.03 (s, 1H), 8.02 (d, J=9 Hz, 2H), 7.63 (d, J=9 Hz, 2H), 7.47-7.39 (m, 3H), 7.37-7.29 (m, 2H), 7.22 (s, 1H), 3.29 (s, 3H).

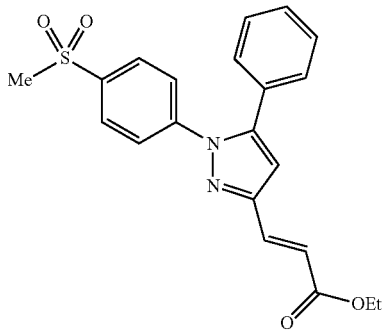 [SMILES: CCOC(=O)/C=C/c1cc(-c2ccccc2)n(-c2ccc(S(C)(=O)=O)cc2)n1]

(E)-3-[1-(4-Methanesulfonyl-phenyl)-5-phenyl-1H-pyrazol-3-yl]-acrylic acid ethyl ester (16). To a solution of aldehyde 12a (1.4 g, 4.3 mmol) and triethyl phosphonoacetate (0.94 mL, 4.73 mmol) in 50 mL of THF was added 60% sodium hydride in oil (0.19 g, 4.73 mmol) at 0° C. The reaction mixture was stirred for 1 hour. The reaction was quenched by adding 5 mL of water, the mixture was extracted with EtOAc. After drying with MgSO$_4$, the solvent was removed in vacuo. The residue was purified by column chromatography with 7:3 (hexanes:EtOAc) to give the titled compound (1.32 g, 77% yield) as a white solid. mp 163.5-168.4° C. $^1$H NMR (300 MHz, DMSO-d$_6$): δ 7.96 (d, J=9 Hz, 2H), 7.58 (d, J=16 Hz, 1H), 7.55 (d, J=9 Hz, 2H), 7.47-7.40 (m, 3H), 7.34-7.27 (m, 2H), 7.28 (s, 1H), 6.72 (d, J=16 Hz, 1H), 4.21 (q, J=7 Hz, 2H), 3.27 (s, 3H), 1.27 (t, J=7 Hz, 3H).

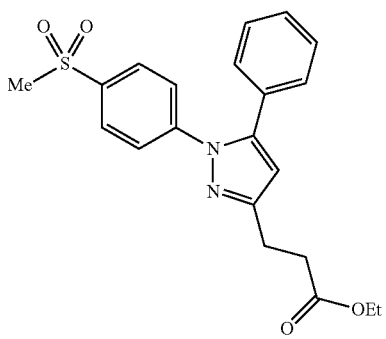 [SMILES: CCOC(=O)CCc1cc(-c2ccccc2)n(-c2ccc(S(C)(=O)=O)cc2)n1]

3-[1-(4-Methanesulfonyl-phenyl)-5-phenyl-1H-pyrazol-3-yl]-propionic acid ethyl ester (17). To a solution of 16 (0.17 g, 0.42 mmol) in 5 mL of EtOAc was added 10% palladium on carbon. The solution was filled with H$_2$ and the reaction mixture was stirred for 2 hours. After the solution was filtered through Celite, the filtrate was concentrated in vacuo. Purification by column chromatography (3:7 EtOAc-hexanes) gave the title compound, 0.15 g (90%) as a white solid. mp 96.5-99.1° C. $^1$H NMR (300 MHz, DMSO-d$_6$): δ 7.91 (d, J=9 Hz, 2H), 7.45 (d, J=9 Hz, 2H), 7.44-7.37 (m, 3H), 7.29-7.23 (m, 2H), 6.57 (s, 1H), 4.09 (q, J=7 Hz, 2H), 3.24 (s, 3H), 2.93 (t, J=7 Hz, 2H), 2.74 (t, J=7 Hz, 2H), 1.18 (t, J=7 Hz, 3H).

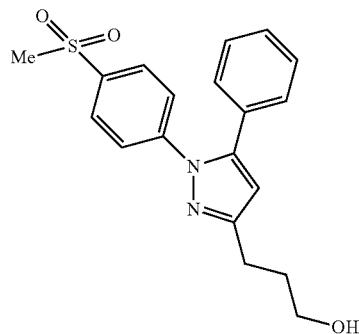 [SMILES: CS(=O)(=O)c1ccc(-n2nc(CCCO)cc2-c2ccccc2)cc1]

3-[1-(4-Methanesulfonyl-phenyl)-5-phenyl-1H-pyrazol-3-yl]-propan-1-ol (18a). To a solution of ester 17 (1.27 g, 4 mmol) in 40 mL of THF was added LiAlH$_4$ (0.24 mg, 6.4 mmol). The reaction mixture was stirred for 6 hours at room temperature. EtOAC (5 mL) and water (10 mL) were added successively. The solvent was removed in vacuo and the resulting solid was filtered. The crude product was purified by column chromatography (EtOAc/Hexanes=7:3) to give the titled compound (0.97 g, 85%) as a white solid mp 119.5-123.4° C. $^1$H NMR (300 MHz, DMSO-d$_6$): δ 7.91 (d, J=9 Hz, 2H), 7.46 (d, J=9 Hz, 2H), 7.43-7.37 (m, 3H), 7.31-7.25 (m, 2H), 6.56 (s, 1H), 4.52 (t, J=5 Hz, 1H), 3.54-3.46 (m, 2H), 3.24 (s, 3H), 2.79-2.60 (m, 2H), 1.88-1.77 (m, 2H).

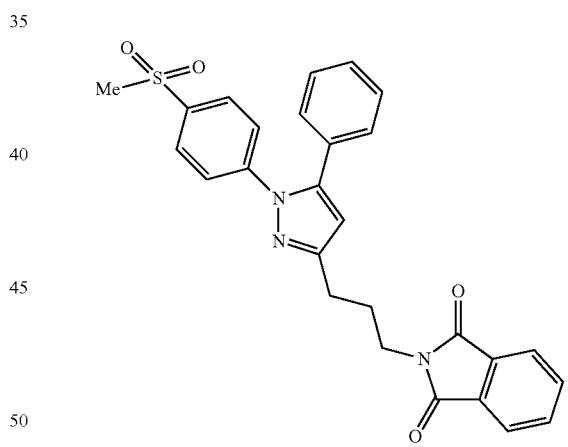

2-{3-[1-(4-Methanesulfonyl-phenyl)-5-phenyl-1H-pyrazol-3-yl]-propyl}-isoindole-1,3-dione (19). To a solution of alcohol 18 (0.3 g, 0.84 mmol), PPh3 (0.22 g, 0.84 mmol), and phthalimide (0.12 g, 0.84 mmol) in 10 mL of THF was added dropwise DIAD (0.17 g, 0.84 mmol), at room temperature. The reaction mixture was stirred overnight. The solvent was evaporated, and the residue was purified by column chromatography with hexanes/EtOAc (1:1) to afford 0.37 g (90%) of the title compound as a white solid. mp 62.4-72.2° C. $^1$H NMR (300 MHz, DMSO-d$_6$): δ 7.88 (d, J=8 Hz, 2H), 7.83-7.74 (m, 5H), 7.43-7.29 (m, 4H), 7.17-7.09 (m, 2H), 6.51 (s, 1H), 3.72 (t, J=7 Hz, 2H), 3.24 (s, 3H), 2.71 (t, J=7 Hz, 2H), 2.15-2.02 (m, 2H).

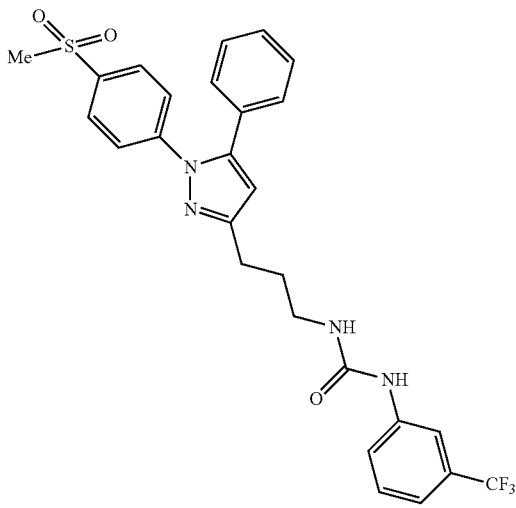 [SMILES: CS(=O)(=O)c1ccc(-n2nc(CCCNC(=O)Nc3cccc(C(F)(F)F)c3)cc2-c2ccccc2)cc1]

1-{3-[1-(4-Methanesulfonyl-phenyl)-5-phenyl-1H-pyrazol-3-yl]-propyl}-3-(3-trifluoromethyl-phenyl)-urea (21a). 35 wt % Hydrazine hydrate (0.16 g, 1.73 mmol) was added to a solution of compound 19 (0.42 g, 0.86 mmol) in CH$_2$Cl$_2$ (15 mL) followed by MeOH (15 mL) at room temperature. The reaction mixture was stirred for 1 day. The white precipitates were filtered off and the solvent was removed in vacuo. The residue was dissolved in aqueous 1N HCl solution and washed with CH$_2$Cl$_2$. Aqueous layer was basified with excess 1N NaOH solution and then extracted with CH$_2$Cl$_2$. After drying with MgSO$_4$, the solvent was evaporated affording the amine 20. To a solution of amine obtained was an added 3-trifluoromethylphenyl isocyanate (0.16 g, 0.86 mmol). The reaction mixture was stirred overnight. After adding water, precipitates were collected by suction filter. The white solid was purified by column chromatography with hexanes/EtOAc (1:1) to give the titled compound (0.37 g, 80 mmol) as a white solid. mp 150.1-151.8° C. $^1$H NMR (300 MHz, DMSO-d$_6$): δ 8.86 (s, 1H), 7.99 (s, 1H), 7.91 (d, J=9 Hz, 2H), 7.53-7.36 (m, 7H), 7.31-7.25 (m, 2H), 7.24-7.19 (m, 1H), 6.59 (s, 1H), 6.39 (t, J=6 Hz, 1H), 3.26-3.17 (m, 2H), 3.24 (s, 3H), 2.70 (t, J=8 Hz, 2H), 1.94-1.80 (m, 2H). MS (ESI) m/z: 543.17 (M+H$^+$). Anal. Calcd for C$_{27}$H$_{25}$F$_3$N$_4$O$_3$S: C, 59.77; H, 4.64; N, 10.33. Found: C, 59.77; H, 4.70; N, 10.23.

Example 11

Preparation of 4-(5-Phenyl-3-{3-[3-(3-trifluoromethyl-phenyl)-ureido]-propyl}-pyrazol-1-yl)-benzenesulfonamide (21b)

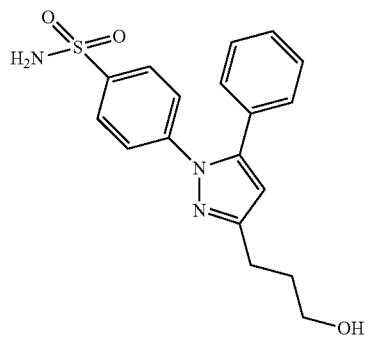 [SMILES: NS(=O)(=O)c1ccc(-n2nc(CCCO)cc2-c2ccccc2)cc1]

4-[3-(3-Hydroxy-propyl)-5-phenyl-pyrazol-1-yl]-benzenesulfonamide (18b). A 60% dispersion of sodium hydride in mineral oil (4.0 g, 100 mmol) was twice washed with hexane (100 mL each) and dried under a stream of nitrogen. Ether (300 mL) was added followed by dropwise addition of ethanol (0.25 mL) and γ-butyrolactone (4.0 mL, 52 mmol). The mixture was cooled to 10° C. and acetophenone (5.8 mL, 50 mmol) in ether (40 mL) was added dropwise over 1 hour. The mixture was warmed to 25° C. and stirred overnight. The mixture was cooled to 0° C. and quenched with ethanol (5 mL) followed by 10% aqueous ammonium sulfate (100 mL). The organic solution was separated, dried over Na$_2$SO$_4$ and concentrated. The residue was chromatographed on silica gel with 1:1 hexane/ethyl acetate to give the desired diketone (3.4 g, 33%) as oil. Pyridine (0.34 mL, 4.2 mmol) and the diketone (700 mg, 3.4 mmol) in methanol (3 mL) were added to slurry of 4-sulfonamidophenylhydrazine·HCl (750 mg, 3.4 mmol) in methanol (8 mL). The mixture was stirred at 25° C. overnight and concentrated in vacuo. The residue was dissolved in methylene chloride and the solution washed with 1N HCl. The organic solution was separated, dried and concentrated. The residue was chromatographed on silica gel using ethyl acetate to give the desired pyrazole (1 g, 90%) as a solid. mp 203.5-205.4° C. $^1$H NMR (300 MHz, DMSO-d$_6$): δ 7.79 (d, J=9 Hz, 2H), 7.45-7.35 (m, 7H), 7.28-7.23 (m, 2H), 6.53 (s, 1H), 4.51 (t, J=5 Hz, 1H), 3.50 (dd, J=12 and 6 Hz, 2H), 2.84-2.56 (m, 2H), 1.88-1.77 (m, 2H).

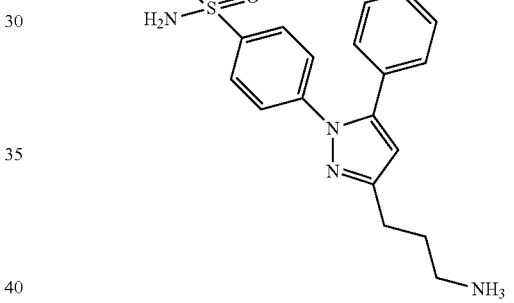

4-[3-(3-Azido-propyl)-5-phenyl-pyrazol-1-yl]-benzenesulfonamide (22). The titled compound was prepared in 88% yield using the compound above using the procedure detailed for compound 9b. mp 114.0-115.6° C. $^1$H NMR (300 MHz, DMSO-d$_6$): δ 7.80 (d, J=9 Hz, 2H), 7.48-7.36 (m, 7H), 7.28-7.23 (m, 2H), 6.58 (s, 1H), 3.46 (t, J=7 Hz, 2H), 2.72 (t, J=8 Hz, 2H), 2.00-1.89 (m, 2H).

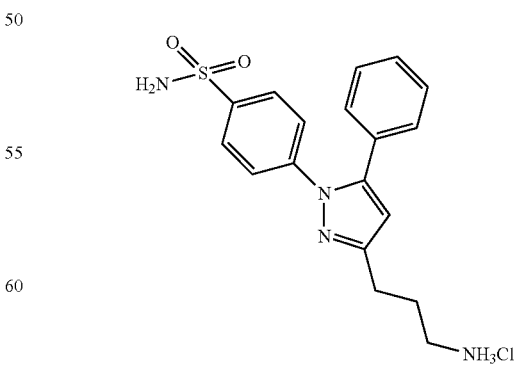

3-[5-Phenyl-1-(4-sulfamoyl-phenyl)-1H-pyrazol-3-yl]-propyl-ammonium; chloride (20b). The titled compound was prepared in 68% yield from 1-adamantyl isocyanate using the procedure detailed for compound 7 except the residue was prepared as an HCl salt with anhydrous HCl (g). $^1$H NMR (300 MHz, TFA-d): δ 8.07 (d, J=8 Hz, 2H), 7.57 (d, J=8.18 Hz, 2H), 7.50-7.43 (m, 1H), 7.40-7.32 (m, 2H), 7.26-7.21 (m, 2H), 7.05 (br s, 2H), 6.88 (s, 1H), 3.48-3.36 (m, 2H), 3.26-3.06 (m, 2H), 2.51-2.35 (m, 2H).

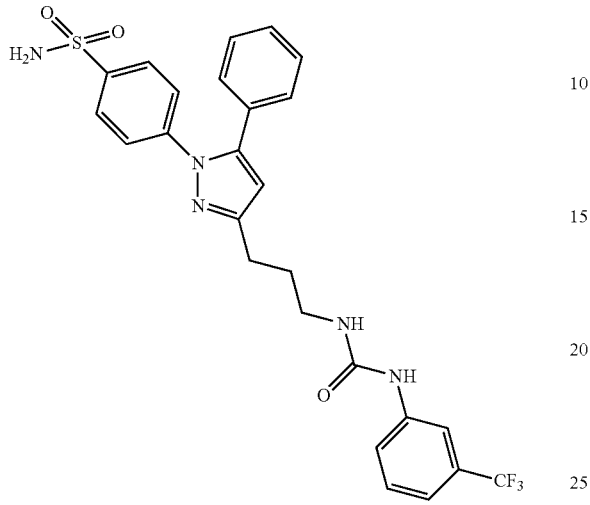

4-(5-Phenyl-3-{3-[3-(3-trifluoromethyl-phenyl)-ureido]-propyl}-pyrazol-1-yl)-benzenesulfonamide (21b). The titled compound was prepared in 84% yield from 3-(trifluoromethyl)phenyl isocyanate using the procedure detailed for compound 7. mp 175.5-176.4° C. $^1$H NMR (300 MHz, DMSO-$d_6$): δ 8.85 (s, 1H), 7.98 (s, 1H), 7.79 (d, J=9 Hz, 2H), 7.53-7.35 (m, 9H), 7.29-7.18 (m, 3H), 6.57 (s, 1H), 6.38 (t, J=6 Hz, 1H), 3.25-3.17 (m, 2H), 2.69 (t, J=8 Hz, 2H), 1.94-1.80 (m, 2H). MS (ESI) m/z: 544.16 (M+H$^+$). Anal. Calcd for $C_{26}H_{24}F_3N_5O_3S$: C, 57.45; H, 4.45; N, 12.88. Found: C, 57.31; H, 4.46; N, 12.74.

Example 12

Preparation of 4-(3-{3-[3-(2,6-Dimethyl-phenyl)-ureido]-propyl}-5-phenyl-pyrazol-1-yl)-benzenesulfonamide (21d)

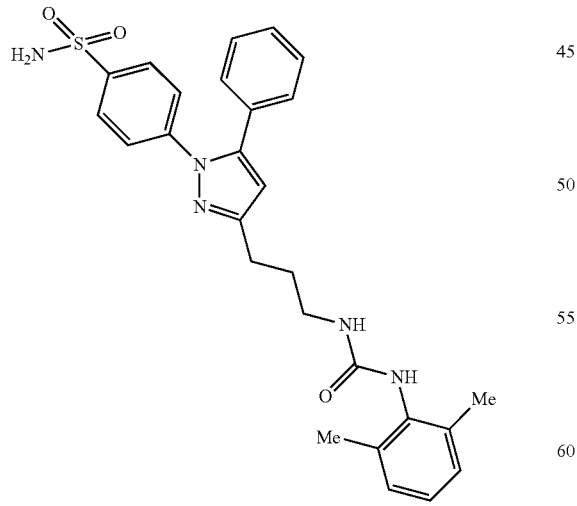

4-(3-{3-[3-(2,6-Dimethyl-phenyl)-ureido]-propyl}-5-phenyl-pyrazol-1-yl)-benzenesulfonamide (21d). The titled compound was prepared in 86% yield from 2,6-(dimethyl)lphenyl isocyanate using the procedure detailed for compound 7. mp 137.9-140.7° C. $^1$H NMR (300 MHz, DMSO-$d_6$): δ 7.79 (d, J=9 Hz, 2H), 7.46-7.34 (m, 7H), 7.29-7.16 (m, 4H), 7.14-7.07 (m, 2H), 6.55 (s, 1H), 3.33-3.30 (m, 1H), 3.22-3.10 (m, 2H), 2.75-2.61 (m, 2H), 1.90-1.73 (m, 2H), 1.12 (d, J=7 Hz, 6H). MS (ESI) m/z: 560.27 (M+H$^+$).

Example 13

Preparation of 4-{5-Phenyl-3-[3-(3-phenyl-ureido)-propyl]-pyrazol-1-yl}-benzenesulfonamide (21e)

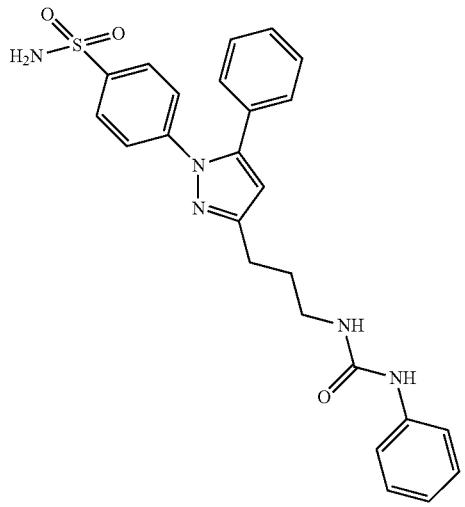 [SMILES: NS(=O)(=O)c1ccc(-n2nc(CCCNC(=O)Nc3ccccc3)cc2-c2ccccc2)cc1]

4-{5-Phenyl-3-[3-(3-phenyl-ureido)-propyl]-pyrazol-1-yl}-benzenesulfonamide (21e). The titled compound was prepared in 90% yield from phenyl isocyanate using the procedure detailed for compound 7. mp 171.0-172.1° C. $^1$H NMR (300 MHz, DMSO-$d_6$): δ 8.43 (s, 1H), 7.79 (d, J=9 Hz, 2H), 7.47-7.36 (m, 9H), 7.29-7.16 (m, 4H), 6.87 (t, J=7 Hz, 1H), 6.57 (s, 1H), 6.23 (t, J=6 Hz, 1H), 3.25-3.14 (m, 2H), 2.69 (t, J=8 Hz, 2H), 1.92-1.78 (m, 2H). MS (ESI) m/z: 476.18 (M+H$^+$). Anal. Calcd for $C_{25}H_{25}N_5O_3S \cdot 0.3CH_4O$: C, 62.63; H, 5.44; N, 14.43. Found: C, 62.63; H, 5.34; N, 14.41.

Example 14

Preparation of 4-{3-[3-(3-Adamantan-1-yl-ureido)-propyl]-5-phenyl-pyrazol-1-yl}-benzenesulfonamide (21f)

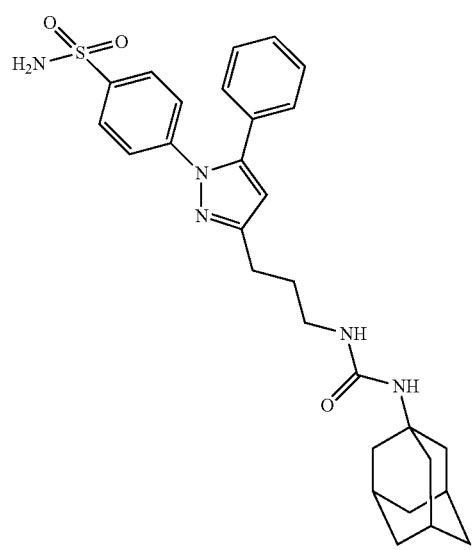 [SMILES: NS(=O)(=O)c1ccc(-n2nc(CCCNC(=O)NC34CC5CC(CC(C5)C3)C4)cc2-c2ccccc2)cc1]

4-{3-[3-(3-Adamantan-1-yl-ureido)-propyl]-5-phenyl-pyrazol-1-yl}-benzenesulfonamide (21f). The titled compound was prepared in 84% yield from 1-adamantyl isocyanate using the procedure detailed for compound 7. mp 139.4-143.5° C. $^1$H NMR (300 MHz, CDCl$_3$): δ 7.75 (d, J=9 Hz, 2H), 7.37-7.28 (m, 5H), 7.21-7.15 (m, 2H), 6.36 (s, 1H), 5.70-5.64 (m, 2H), 4.68-4.60 (m, 1H), 4.29 (s, 1H), 3.23 (q, J=7 Hz, 2H), 2.78 (t, J=7, 2H), 2.08-1.87 (m, 9H), 1.67-1.59 (m, 6H), 1.29-1.22 (m, 2H). MS (ESI) m/z: 534.25 (M+H$^+$).

Example 15

Preparation of 4-{3-[3-(3-Cycloheptyl-ureido)-propyl]-5-phenyl-pyrazol-1-yl}-benzenesulfonamide (21g)

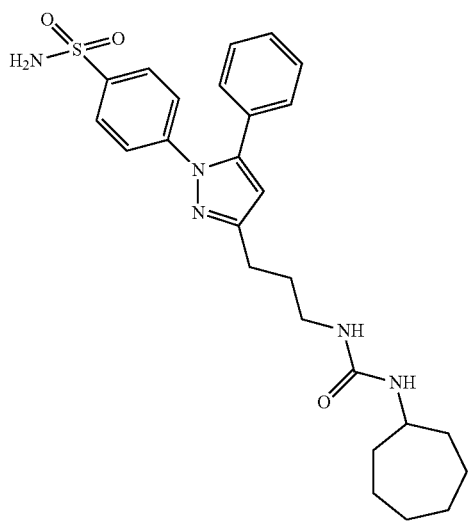 [SMILES: NS(=O)(=O)c1ccc(-n2nc(CCCNC(=O)NC3CCCCCC3)cc2-c2ccccc2)cc1]

4-{3-[3-(3-Cycloheptyl-ureido)-propyl]-5-phenyl-pyrazol-1-yl}-benzenesulfonamide (21g). The titled compound was prepared in 91% yield from cycloheptyl isocyanate using the procedure detailed for compound 7. mp 164.2-169.8° C. $^1$H NMR (300 MHz, DMSO-d$_6$): δ 7.79 (d, J=9 Hz, 2H), 7.47-7.36 (m, 7H), 7.29-7.22 (m, 2H), 6.55 (s, 1H), 5.82-5.70 (m, 2H), 3.63-3.49 (m, 1H), 3.13-3.02 (m, 2H), 2.63 (t, J=8 Hz, 2H), 1.84-1.66 (m, 4H), 1.60-1.27 (m, 10H). MS (ESI) m/z: 496.24 (M+H$^+$).

Example 16

Preparation of 4-(3-{3-[3-(4-Chloro-phenyl)-ureido]-propyl}-5-phenyl-pyrazol-1-yl)-benzenesulfonamide (21h)

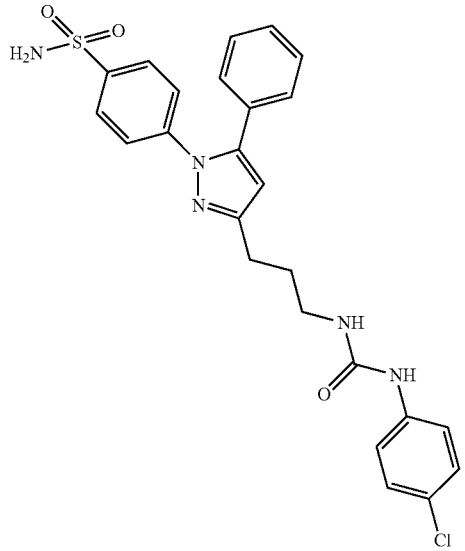 [SMILES: NS(=O)(=O)c1ccc(-n2nc(CCCNC(=O)Nc3ccc(Cl)cc3)cc2-c2ccccc2)cc1]

4-(3-{3-[3-(4-Chloro-phenyl)-ureido]-propyl}-5-phenyl-pyrazol-1-yl)-benzenesulfonamide (21h). The titled compound was prepared in 92% yield from 4-chlorophenyl isocyanate using the procedure detailed for compound 7. mp 103.2-110.4° C. $^1$H NMR (300 MHz, DMSO-d$_6$): δ 8.60 (s, 1H), 7.79 (d, J=9 Hz, 2H), 7.47-7.35 (m, 9H), 7.29-7.21 (m, 4H), 6.57 (s, 1H), 6.29 (t, J=6 Hz, 1H), 3.26-3.13 (m, 2H), 2.68 (t, J=8 Hz, 2H), 1.92-1.77 (m, 2H). MS (ESI) m/z: 510.14 (M+H$^+$). Anal. Calcd for C$_{25}$H$_{24}$ClN$_5$O$_3$S.MeOH: C, 58.22; H, 4.98; N, 13.31. Found: C, 58.18; H, 4.78; N, 13.25.

Example 17

Preparation of 4-(5-Phenyl-3-{3-[3-(4-trifluoromethyl-phenyl)-ureido]-propyl}-pyrazol-1-yl)-benzenesulfonamide (21i)

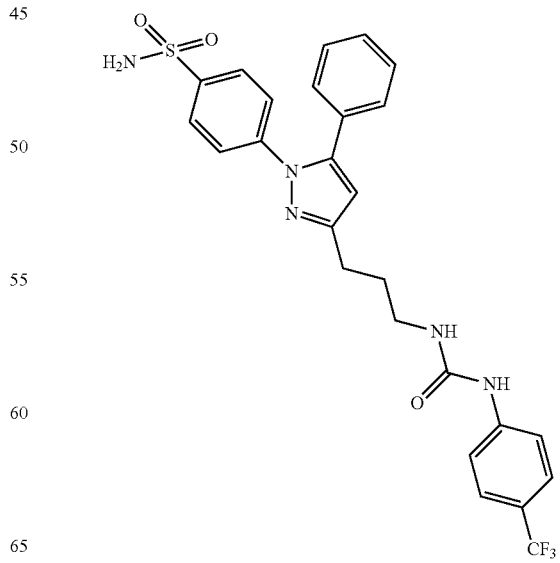

4-(5-Phenyl-3-{3-[3-(4-trifluoromethyl-phenyl)-ureido]-propyl}-pyrazol-1-yl)-benzenesulfonamide (21i). The titled compound was prepared in 85% yield from 3-trifluoromethylphenyl isocyanate using the procedure detailed for compound 7. mp 184.8-185.6° C. $^1$H NMR (300 MHz, DMSO-$d_6$): δ 8.90 (s, 1H), 7.79 (d, J=9 Hz, 2H), 7.63-7.53 (m, 4H), 7.46-7.36 (m, 7H), 7.28-7.22 (m, 2H), 6.57 (s, 1H), 6.41 (t, J=6 Hz, 1H), 3.27-3.15 (m, 2H), 2.69 (t, J=8 Hz, 2H), 1.93-1.78 (m, 2H). MS (ESI) m/z: 544.16 (M+H$^+$). Anal. Calcd for $C_{26}H_{24}F_3N_5O_3S$: C, 57.45; H, 4.45; N, 12.88. Found: C, 57.50; H, 4.47; N, 12.72.

Example 18

Preparation of 4-(5-Phenyl-3-{3-[3-(4-trifluoromethoxy-phenyl)-ureido]-propyl}-pyrazol-1-yl)-benzenesulfonamide (21j)

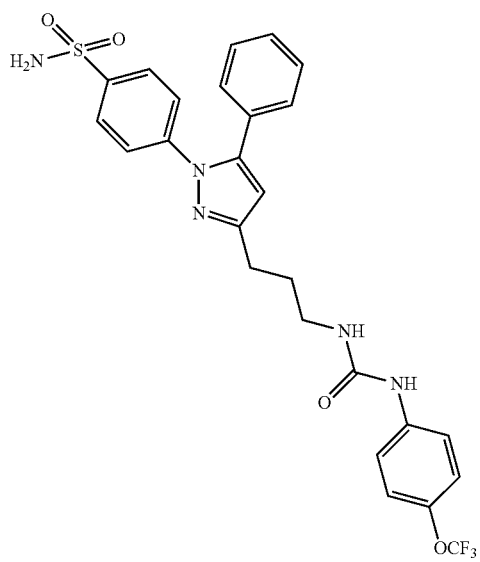 [SMILES: NS(=O)(=O)c1ccc(-n2nc(CCCNC(=O)Nc3ccc(OC(F)(F)F)cc3)cc2-c2ccccc2)cc1]

4-(5-Phenyl-3-{3-[3-(4-trifluoromethoxy-phenyl)-ureido]-propyl}-pyrazol-1-yl)-benzenesulfonamide (21j). The titled compound was prepared in 84% yield from 3-trifluoromethylphenyl isocyanate using the procedure detailed for compound 7. mp 205.7-206.6° C. $^1$H NMR (300 MHz, DMSO-$d_6$): δ 8.67 (s, 1H), 7.79 (d, J=9 Hz, 2H), 7.49 (d, J=9 Hz, 2H), 7.45-7.36 (m, 7H), 7.29-7.18 (m, 4H), 6.57 (s, 1H), 6.30 (t, J=5 Hz, 1H), 3.27-3.15 (m, 2H), 2.68 (t, J=8 Hz, 2H), 1.92-1.79 (m, 2H). MS (ESI) m/z: 560.16 (M+H$^+$). Anal. Calcd for $C_{26}H_{24}F_3N_5O_4S$: C, 55.81; H, 4.32; N, 12.52. Found: C, 55.82; H, 4.19; N, 12.41.

Example 19

Preparation of 1-[5-tert-Butyl-1-(4-methanesulfonyl-phenyl)-1H-pyrazol-3-ylmethyl]-3-(3-trifluoromethyl-phenyl)-urea (11h)

Compound 11h was prepared according to the scheme below:

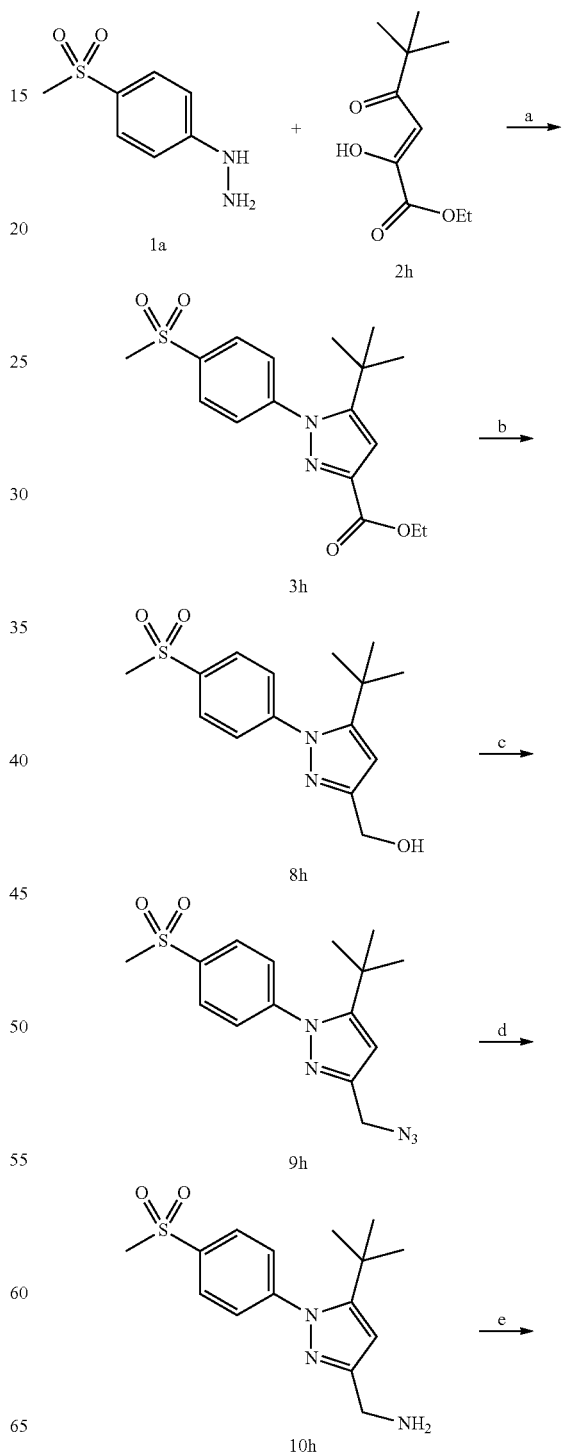

-continued

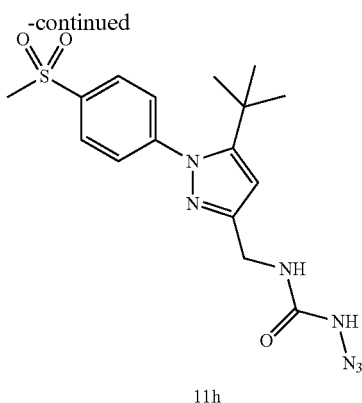

11h

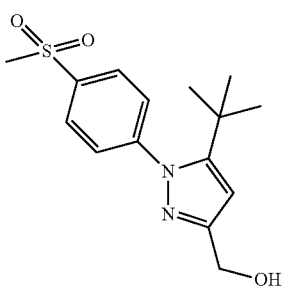 [SMILES: CC(C)(C)c1cc(CO)nn1-c1ccc(S(C)(=O)=O)cc1]

5-tert-Butyl-1-(4-methanesulfonyl-phenyl)-1H-pyrazole-3-carboxylic acid ethyl ester (3h). To a solution of 1M NaHMDS in THF in 120 mL of THF was added dropwise pinacolin (3.1 mL, 25 mmol) at 78° C. After 1 hour, diethyl oxalate (3.7 mL, 27.5 mmol) was added dropwise. The reaction mixture was allowed to warm up to room temperature and stirred overnight. The reaction was quenched by adding 1N HCl solution (50 mL). The reaction mixture was extracted with EtOAc and dried with MgSO$_4$. The mixture was concentrated in vacuo. The product 2h was used without further purification. To a solution of 2h (1 g, 5 mmol) in EtOH (50 mL) was added 4-methylsulfonylphenylhydrazine 1a (1.22 g, 5.5 mmol) at room temperature. The reaction mixture was stirred overnight and refluxed for 3 hour. After cooling, the solvent was removed in vacuo. The resulting solid was purified by column chromatography with hexanes/EtOAc (1:1) to afford the titled compound (1 g, 57% yield) as a white solid. mp 174.9-177.6° C. $^1$H NMR (300 MHz, DMSO-d$_6$): δ 8.11 (d, J=9 Hz, 2H), 7.80 (d, J=9 Hz, 2H), 6.76 (s, 1H), 4.27 (q, J=7 Hz, 2H), 3.35 (s, 3H), 1.27 (t, J=7 Hz, 3H), 1.16 (s, 9H).

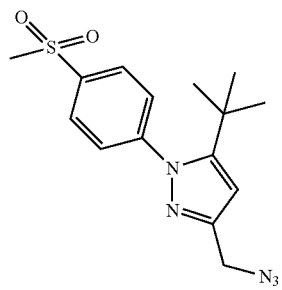 [SMILES: CC(C)(C)c1cc(CN=[N+]=[N-])nn1-c1ccc(S(C)(=O)=O)cc1]

[5-tert-Butyl-1-(4-methanesulfonyl-phenyl)-1H-pyrazol-3-yl]-methanol (8h). To a solution of compound 3h (0.8 g, 2.28 mmol) in 25 mL of THF was added LiAlH$_4$ (0.14 g, 3.65 mmol). The reaction mixture was stirred for 6 hours at room temperature. EtOAc (50 mL) and water (50 mL) were added successively. The solvent was removed in vacuo and the resulting solid was filtered. The crude product was purified by column chromatography (EtOAc/Hexanes=7/3) to give the titled compound (0.56 g, 80% yield) as a white solid. mp 143.0-146.5° C. $^1$H NMR (300 MHz, DMSO-d$_6$): δ 8.06 (d, J=8 Hz, 2H), 7.68 (d, J=8 Hz, 2H), 6.26 (s, 1H), 5.10 (t, J=6 Hz, 1H), 4.39 (d, J=6 Hz, 2H), 3.32 (s, 3H), 1.14 (s, 9H).

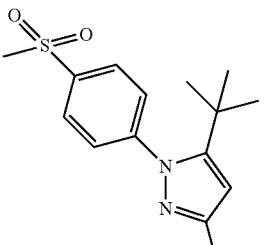

3-Azidomethyl-5-tert-butyl-1-(4-methanesulfonyl-phenyl)-1H-pyrazole (9h). To a solution of alcohol 8h (0.5 g, 1.6 mmol) in 20 mL of THF was added methanesulfonyl chloride (0.14 mL, 1.76 mmol) followed by Et$_3$N (0.28 mL, 2 mmol) at 0° C. The reaction mixture was stirred for 2 hours. After adding water (20 mL), the product was extracted with EtOAc. The organic layer was dried with MgSO$_4$ and the solvent was removed in vacuo. To a solution of mesylate obtained in 1,4-dioxane (10 mL) and water (10 mL) was added NaN$_3$ (0.26 g, 4 mmol). The reaction mixture was heated at 80° C. for 3 hours. After cooling, the solvent was removed in vacuo. The residue was purified by column chromatography with hexanes/EtOAc (1:1) to give the titled compound (0.48 g, 90%) as a white solid. mp 115.4-117.3° C. $^1$H NMR (300 MHz, DMSO-d$_6$): δ 8.08 (d, J=8 Hz, 2H), 7.72 (d, J=8 Hz, 2H), 6.34 (s, 1H), 4.38 (s, 2H), 3.34 (s, 3H), 1.15 (s, 9H).

C-[5-tert-Butyl-1-(4-methanesulfonyl-phenyl)-1H-pyrazol-3-yl]-methylamine (10h). To a solution of 9h (0.4 g, 1.2 mmol) in EtOAc was added 10% palladium on carbon. The solution was filled with H$_2$ and the reaction mixture was stirred for 2 hours. After the solution was filtered through Celite, the filtrate was concentrated in vacuo. Purification by recrystallization with DCM/hexanes gave the title compound 10h, 0.35 g (95%) as a white solid. mp 137.5-145.1° C. $^1$H NMR (300 MHz, DMSO-d$_6$): δ 8.05 (d, J=8 Hz, 2H), 7.67 (d, J=8 Hz, 2H), 6.27 (s, 1H), 3.62 (s, 2H), 3.32 (s, 3H), 2.07-1.83 (m, 2H), 1.14 (s, 9H).

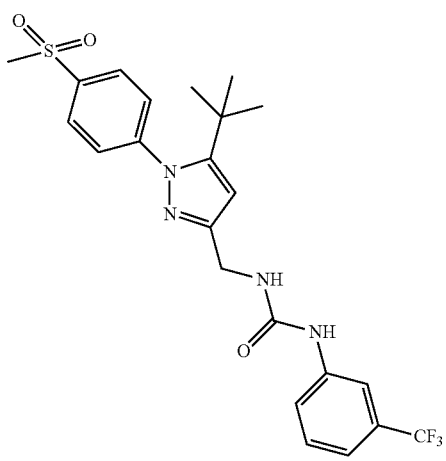 [SMILES: CC(C)(C)c1cc(CNC(=O)Nc2cccc(C(F)(F)F)c2)nn1-c1ccc(S(C)(=O)=O)cc1]

1-[5-tert-Butyl-1-(4-methanesulfonyl-phenyl)-1H-pyrazol-3-ylmethyl]-3-(3-trifluoromethyl-phenyl)-urea (11h). To a solution of compound amine 10h (0.15 g, 0.49 mmol) in 5 mL of DMF was added 3-(trifluoromethyl)phenyl isocyanates (92 mg, 0.49 mmol) followed by Et$_3$N (0.08 mL, 0.54 mmol) at 0° C. The reaction mixture was stirred overnight. The reaction mixture was poured into water, and the resulting precipitates were collected and washed with water. The crude product was recrystallized from DCM/hexanes to afford 0.19 g (80%) of the titled compound 11h as a white solid. mp 161.9-165.0° C. $^1$H NMR (300 MHz, DMSO-d$_6$): δ 9.00 (s, 1H), 8.07 (d, J=8 Hz, 2H), 7.98 (s, 1H), 7.71 (d, J=8 Hz, 2H), 7.53-7.41 (m, 2H), 7.26-7.20 (m, 1H), 6.67 (t, J=5 Hz, 1H), 6.24 (s, 1H), 4.27 (d, J=5 Hz, 2H), 3.33 (s, 3H), 1.17-1.12 (m, 9H). MS (ESI) m/z: 495.17 (M+H$^+$). Anal. Calcd for C$_{23}$H$_{25}$F$_3$N$_4$O$_3$S: C, 55.86; H, 5.10; N, 11.33. Found: C, 55.80; H, 5.20; N, 11.20.

Example 20

Preparation of 4-(5-p-Tolyl-3-[3-{3-(3-trifluoromethyl-phenyl)-ureido]-propyl}-pyrazol-1-yl)-benzenesulfonamide (21c)

Compound 21c was prepared according to the scheme below:

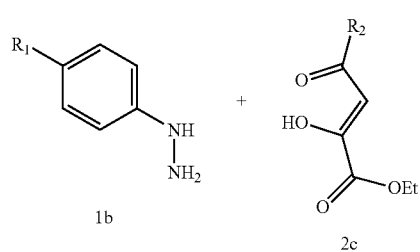

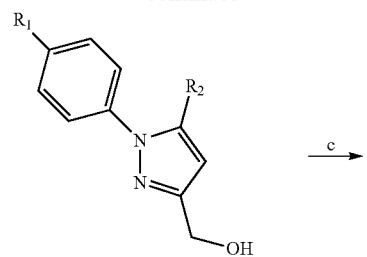

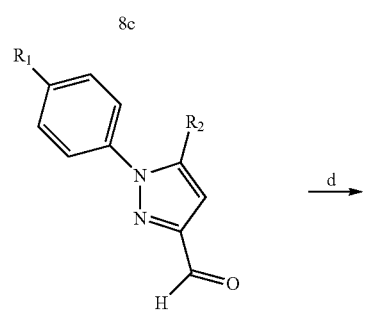

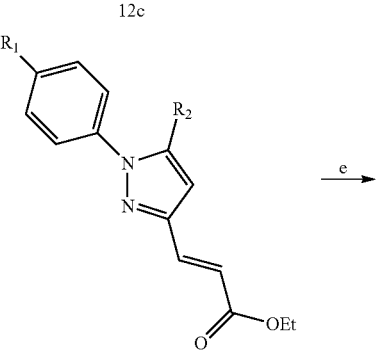

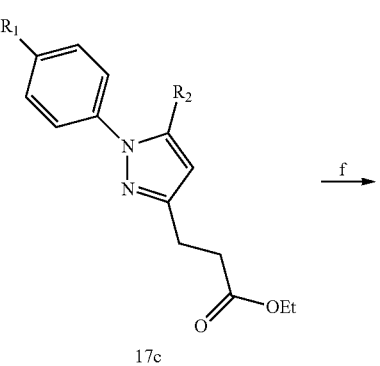

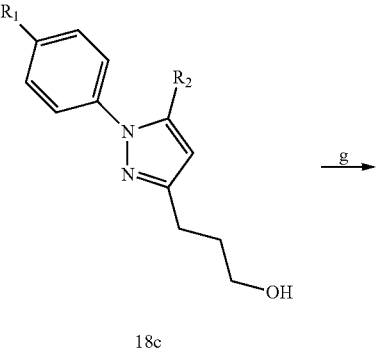

-continued

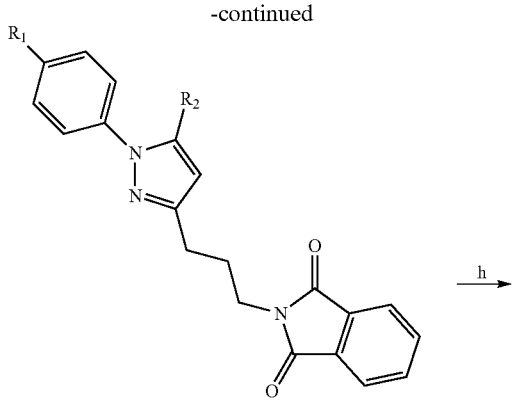

19c

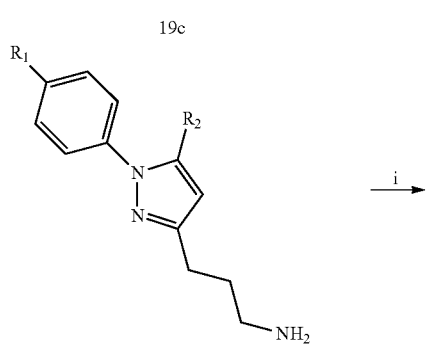

20c

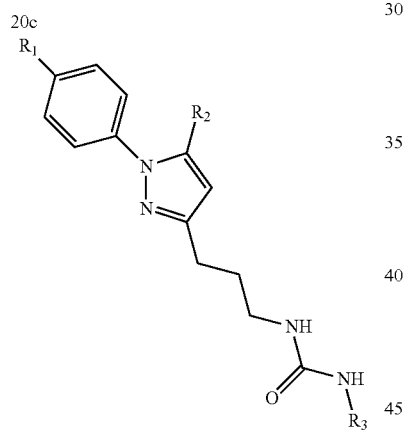

21c 1-(4-Sulfamoyl-phenyl)-5-p-tolyl-1H-pyrazole-3-carboxylic acid ethyl ester (3c). To a solution of 26.8 mL (26.8 mmol) of NaHMDS (1.0 M solution in THF) in THF (120 mL) was added a solution of 4'-methylacetophenone (3.35 g, 25 mmol) in 30 mL of THF at −78° C. After 1 hour, 3.7 mL (27.5 mmol) of diethyl oxalate was added dropwise. The reaction mixture was allowed to warm to room temperature and stirred overnight. The solvent was removed in vacuo and the resulting yellowish solid was filtered and washed with 100 mL of ethyl ether to give a sodium salt of 2c (5 g, 78%). The resulting sodium salt (was then suspended in EtOH (200 mL) and 4.8 g (21.5 mmol) of 4-amidosulfonylphenylhydrazine 1b was added at room temperature. After 1 hour, 1.1 mL of AcOH was added and the reaction mixture was refluxed for 2 hours. After cooling, the solvent was removed in vacuo. The resulting solid was purified by recrystallization with MeOH to afford the titled compound (5.6 g, 75% yield) as a white solid. mp 219.9-222.5° C. $^1$H NMR (300 MHz, DMSO-d$_6$): δ 7.87 (d, J=9 Hz, 2H), 7.58-7.52 (m, 2H), 7.51 (d, J=9 Hz, 2H), 7.21 (d, J=8 Hz, 2H), 7.17 (d, J=8 Hz, 2H), 7.11 (s, 1H), 4.34 (q, J=7 Hz, 2H), 2.31 (s, 3H), 1.32 (t, J=7 Hz, 3H).

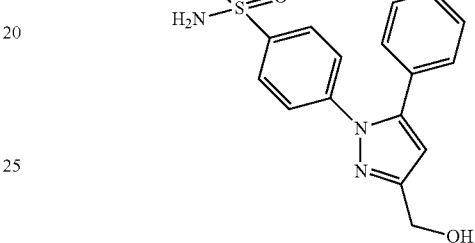

4-(3-Hydroxymethyl-5-p-tolyl-pyrazol-1-yl)-benzenesulfonamide (8c). To a solution of compound 3c (4 g, 1.04 mmol) in 20 mL of THF was added LiAlH$_4$ (1.26 g, 33.2 mmol). The reaction mixture was stirred for 6 hours at room temperature. EtOAC (30 mL) and water (30 mL) were added successively. The solvent was removed in vacuo and the resulting solid was filtered. The crude product was purified by column chromatography (EtOAc/Hexanes in adequate proportions) to give the compound (2.85 g, 80%) as a white solid. mp 165.9-169.3° C. $^1$H NMR (300 MHz, DMSO-d$_6$): δ 7.81 (d, J=9 Hz, 2H), 7.48-7.43 (m, 2H), 7.41 (d, J=9 Hz, 2H), 7.21 (d, J=8 Hz, 2H), 7.14 (d, J=8 Hz, 2H), 6.59 (s, 1H), 5.26 (t, J=6 Hz, 1H), 4.51 (d, J=6 Hz, 2H), 2.31 (s, 3H).

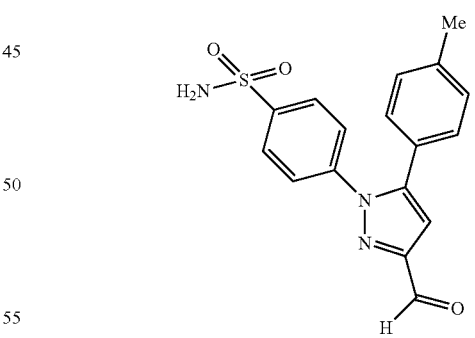

4-(3-Formyl-5-p-tolyl-pyrazol-1-yl)-benzenesulfonamide (12c). To a solution of alcohol 8c (0.46 g, 1.34 mmol) and 0.43 g of powdered 4 Å molecular sieves in 20 mL of DCM, was added PCC (0.43 g, 2.0 mmol) at room temperature. After 6 hours, the reaction mixture was filtered through a 0.75-in. pad of Celite. The filtrate was concentrated in vacuo then the residue was purified by column chromatography to afford the titled compound (0.21 g, 46%) as a white solid. mp 195.9-197.9° C. $^1$H NMR (300 MHz, DMSO-d$_6$): δ 10.01 (s, 1H), 7.88 (d, J=9 Hz, 2H), 7.56 (d, J=9 Hz, 2H), 7.55-7.52 (m, 2H), 7.25-7.17 (m, 4H), 7.15 (s, 1H), 2.32 (s, 3H).

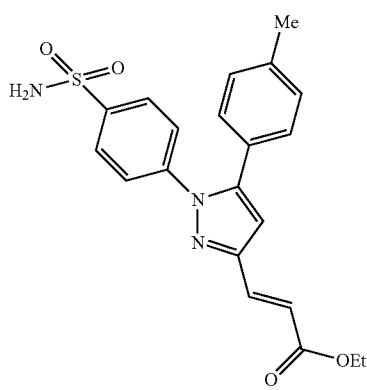 [SMILES: CCOC(=O)/C=C/c1cc(-c2ccc(C)cc2)n(-c2ccc(S(N)(=O)=O)cc2)n1]

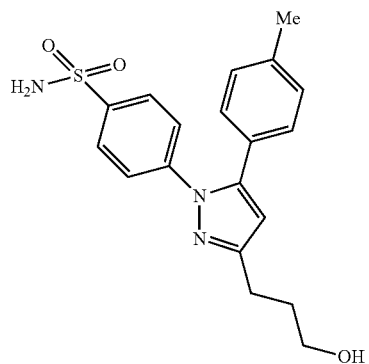

(E)-3-[1-(4-Sulfamoyl-phenyl)-5-p-tolyl-1H-pyrazol-3-yl]-acrylic acid ethyl ester (16c). To a solution of aldehyde 12c (0.16 g, 0.47 mmol) and triethyl phosphonoacetate (0.12 g, 0.52 mmol) in 5 mL of THF was added 60% sodium hydride in oil (21 mg, 0.52 mmol) at 0° C. The reaction mixture was stirred for 1 hour. After adding 5 mL of water, the mixture was extracted with EtOAc. After drying with MgSO4, the solvent was removed in vacuo. The resulting white solid was filtered and washed with hexanes to give the titled compound (0.14 g, 73% yield) as a white solid. mp 166.8-171.2° C. $^1$H NMR (300 MHz, CDCl$_3$): δ 7.88 (d, J=9 Hz, 2H), 7.72 (d, J=16 Hz, 1H), 7.45 (d, J=9 Hz, 2H), 7.20-7.08 (m, 4H), 6.70 (s, 1H), 6.52 (d, J=16 Hz, 1H), 4.90 (s, 2H), 4.27 (q, J=7 Hz, 2H), 2.38 (s, 3H), 1.34 (t, J=7 Hz, 3H).

4-[3-(3-Hydroxy-propyl)-5-p-tolyl-pyrazol-1-yl]-benzenesulfonamide (18c). To a solution of ester 17c (0.11 g, 0.27 mmol) in 5 mL of THF was added LiAlH$_4$ (32 mg, 0.85 mmol). The reaction mixture was stirred for 6 hours at room temperature. EtOAC (10 mL) and water (5 mL) were added successively. The solvent was removed in vacuo and the resulting solid was filtered. The crude product was purified by column chromatography (EtOAc/Hexanes in adequate proportions) to give the titled compound (80 mg, 81%) as a white solid. mp 123.4-125.6° C. $^1$H NMR (300 MHz, DMSO-d$_6$): δ 7.79 (d, J=9 Hz, 2H), 7.47-7.42 (m, 2H), 7.39 (d, J=9 Hz, 2H), 7.20 (d, J=8 Hz, 2H), 7.13 (d, J=8 Hz, 2H), 6.49 (s, 1H), 4.52 (t, J=5 Hz, 1H), 3.53-3.45 (m, 2H), 2.73-2.59 (m, 2H), 2.31 (s, 3H), 1.87-1.75 (m, 2H).

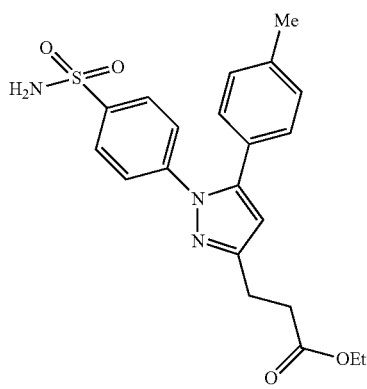 [SMILES: CCOC(=O)CCc1cc(-c2ccc(C)cc2)n(-c2ccc(S(N)(=O)=O)cc2)n1]

3-[1-(4-Sulfamoyl-phenyl)-5-p-tolyl-1H-pyrazol-3-yl]-propionic acid ethyl ester (17c). To a solution of 16c (0.13 g, 0.32 mmol) in 5 mL of EtOAc was added 10% palladium on carbon. The solution was filled with H$_2$ and the reaction mixture was stirred for 2 hours. After the solution was filtered through Celite, the filtrate was concentrated in vacuo. Purification by column chromatography (3:7 EtOAc-haxanes) gave the title compound, 0.11 g (84%) as a white solid. mp 116.5-117.2° C. $^1$H NMR (300 MHz, CDCl$_3$): δ 7.79 (d, J=9 Hz, 2H), 7.36 (d, J=9 Hz, 2H), 7.17-7.04 (m, 4H), 6.32 (s, 1H), 5.23 (s, 2H), 4.17 (q, J=7 Hz, 2H), 3.05 (t, J=8 Hz, 2H), 2.76 (t, J=8 Hz, 2H), 2.35 (s, 3H), 1.26 (t, J=7 Hz, 3H).

4-{3-[3-(1,3-Dioxo-1,3-dihydro-isoindol-2-yl)-propyl]-5-p-tolyl-pyrazol-1-yl}-benzenesulfonamide (19c). To a solution of alcohol 18c (0.1 g, 0.27 mmol), PPh$_3$ (0.11 g, 0.40 mmol), and phthalimide (60 mg, 0.40 mmol) in 5 mL of THF was added dropwise DIAD (54 mg, 0.27 mmol) at room temperature. The reaction mixture was stirred overnight. The solvent was evaporated, and the resulting solid was recrystallized from methanol to afford 0.53 g (87%) of the title compound as a white solid. $^1$H NMR (300 MHz, CDCl$_3$): δ 7.84-7.76 (m, 1H), 7.70-7.65 (m, 1H), 7.34 (d, J=8.76 Hz, 1H), 7.11 (d, J=7.89 Hz, 1H), 7.00 (d, J=8.15 Hz, 1H), 6.33 (s, 1H), 4.96 (s, 1H), 3.85 (t, J=6.96, 6.96 Hz, 1H), 2.80 (t, J=7.47, 7.47 Hz, 1H), 2.35 (s, 1H), 2.24-2.13 (m, 1H).

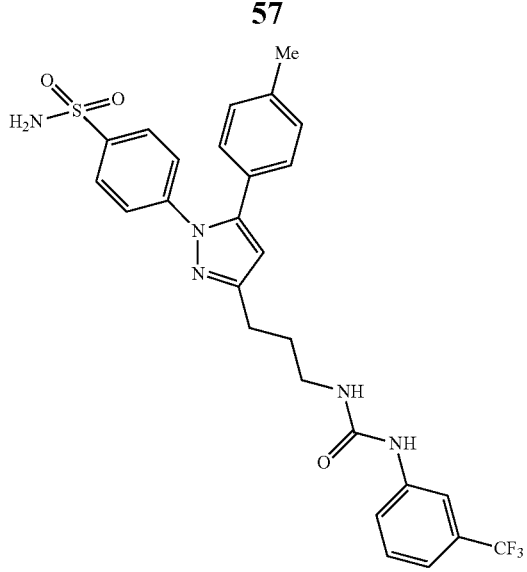

4-(5-p-Tolyl-3-{3-[3-(3-trifluoromethyl-phenyl)-ureido]-propyl}-pyrazol-1-yl)-benzenesulfonamide (21c). 35 wt % Hydrazine hydrate (0.11 g, 1.2 mmol) was added to a solution of compound 19c (0.3 g, 0.62 mmol) in DCM (5 mL) followed by MeOH (5 mL) at room temperature. The reaction mixture was allowed to stir overnight. The resulting white precipitates were filtered off and the solvent was removed in vacuo. The resulting white solids were dissolved in aqueous 1N HCl solution and washed with DCM. Aqueous layer was basified with excess 1N NaOH solution and then extracted with DCM. After drying with $MgSO_4$, the solvent was evaporated affording crude amine 20c, which was used in the next step without further purification. To a solution of compound amine obtained in DMF was added 3-(trifluoromethyl)phenyl isocyanates (0.12 g, 0.62 mmol) followed by $Et_3N$ (0.09 mL, 0.62 mmol) at 0° C. The reaction mixture was stirred overnight. The reaction mixture was poured into water, and the resulting precipitates were collected and washed with water. The crude product was recrystallized from DCM/hexanes to afford 0.24 g (71%) of the titled compound as a white solid. $^1$H NMR (300 MHz, DMSO-$d_6$): δ 8.85 (s, 1H), 7.98 (s, 1H), 7.79 (d, J=9 Hz, 2H), 7.53-7.36 (m, 5H), 7.24-7.17 (m, 4H), 7.13 (d, J=8 Hz, 2H), 6.52 (s, 1H), 6.38 (t, J=6 Hz, 1H), 3.27-3.14 (m, 2H), 2.72-2.62 (m, 2H), 2.31 (s, 3H), 1.92-1.78 (m, 2H).

Example 21

Molecular Modeling

Molecular modeling was performed using "Scigress Explorer Standard ver. 7.7.0.49" software (Fujitsu Computer Systems Corporation). The atomic coordinates of the crystal structures of human sEH complex with CIU (N-cyclohexyl-N'-(4-iodophenyl)urea) and of murine COX-2 complexed with SC-558 (1-phenylsulfonamide-3-trifluoromethyl-5-parabromophenylpyrazole) were retrieved from Protein Data Bank (entry 1VJ5 and 1CX2, respectively). 21i was docked into the ligand-binding pocket manually by superposition with the parent molecule (CIU or SC-558) and minimized on MM geometry (MM3). The image was produced using freewares VMD 1.8.6 (Molecular Modeling. Molecular modeling was performed using "Scigress Explorer Standard ver. 7.7.0.49" software (Fujitsu Computer Systems Corporation). The atomic coordinates of the crystal structures of human sEH complex with CIU (N-cyclohexyl-N'-(4-iodophenyl)urea) and of murine COX-2 complexed with SC-558 (1-phenylsulfonamide-3-trifluoromethyl-5-parabromophenylpyrazole) were retrieved from Protein Data Bank (entry 1VJ5 and 1CX2, respectively). 21i was docked into the ligand-binding pocket manually by superposition with the parent molecule (CIU or SC-558) and minimized on MM geometry (MM3). The image was produced using freewares VMD 1.8.6 (www.ks.uiuc.edu/Research/vmd) and POV-Ray 3.6 (www.povray.org).

Example 22 sEH $IC_{50}$ Assay

For the recombinant affinity assay, purified sEHs (human, mouse and rat) were used in a fluorescent-based assay to determine $IC_{50}$ values. Enzymes (~1 nM human sEH) were incubated with the inhibitors for 5 min in 25 mM Bis-Tris/HCl buffer (200 μL; pH 7.0) at 30° C. before substrate (cyano (2-methoxynaphthalen-6-yl)methyl trans-(3-phenyl-oxyran-2-yl)methyl carbonate, CMNPC) was added ($[S]_{final}$=5 μM). Activity was assessed by measuring the appearance of the fluorescent 6-methoxynaphthaldehyde product ($\lambda_{em.}$=330 nm, $\lambda_{ex.}$=465 nm) at 30° C. during a 10 min incubation (Spectramax M2; Molecular Device, Inc., Sunnyvale, Calif.). The $IC_{50}$ values represent the concentration of the inhibitors

TABLE 1

Elemental analysis of compounds 7, 11a-h, 15, and 21a-b, d-j.

| Compd. | Mol. Formula | Cald. | Found |
|---|---|---|---|
| 11a | $C_{28}H_{32}N_4O_3S$ | C, 66.64; H, 6.39; N, 11.10 | C, 66.46; H, 6.31; N, 10.86 |
| 11b | $C_{25}H_{30}N_4O_3S \cdot 0.25CH_4O$ | C, 63.90; H, 6.58; N, 11.80 | C, 63.91 ;H, 6.42; N, 11.92 |
| 11c | $C_{24}H_{22}N_4O_3S$ | C, 64.56; H, 4.97; N, 12.55 | C, 64.23; H, 5.07; N, 12.33 |
| 11d | $C_{25}H_{21}F_3N_4O_4S$ | C, 56.60; H, 3.99; N, 10.56 | C, 56.42; H, 3.93; N, 10.35 |
| 11e | $C_{25}H_{21}F_3N_4O_3S \cdot 0.375CH_4O$ | C, 57.88; H, 4.31; N, 10.64 | C, 57.88; H, 4.31; N, 10.36 |
| 11f | $C_{25}H_{21}F_3N_4O_3S$ | C, 58.36; H, 4.11; N, 10.89 | C, 58.74; H, 4.48; N, 10.58 |
| 11g | $C_{25}H_{20}F_3N_5O_3S$ | C, 55.92; H, 3.91; N, 13.59 | C, 56.11; H, 3.97; N, 13.49 |
| 11h | $C_{23}H_{25}F_3N_4O_3S$ | C, 55.86; H, 5.10; N, 11.33 | C, 55.80; H, 5.20; N, 11.20 |
| 7 | $C_{23}H_{18}F_3N_5O_3S \cdot 0.36CH_4O$ | C, 54.69; H, 3.82; N, 13.65 | C, 54.69; H, 3.70; N, 13.44 |
| 15 | $C_{25}H_{22}F_3N_5O_3S$ | C, 56.70; H, 4.19; N, 13.23 | C, 56.52; H, 4.35; N, 12.99 |
| 21a | $C_{27}H_{25}F_3N_4O_3S$ | C, 59.77; H, 4.64; N, 10.33 | C, 59.77; H, 4.70; N, 10.23 |
| 21b | $C_{26}H_{24}F_3N_5O_3S$ | C, 57.45; H, 4.45; N, 12.88 | C, 57.31 ;H, 4.46; N, 12.74 |
| 21d | $C_{31}H_{37}N_5O_3S$ | C, 66.52; H 6.66; N, 12.51 | C, 66.13; H, 6.67; N, 12.35 |
| 21e | $C_{25}H_{25}N_5O_3S \cdot 0.3CH_4O$ | C, 62.63; H, 5.44; N, 14.43 | C, 62.63; H, 5.34; N, 14.41 |
| 21f | $C_{29}H_{35}N_5O_3S$ | C, 65.27; H, 6.61; N, 13.12 | C, 65.40; H, 6.66; N, 12.94 |
| 21g | $C_{26}H_{33}N_5O_3S$ | C, 63.01; H, 6.71; N, 14.13 | C, 62.81; H, 6.64; N, 14.07 |
| 21h | $C_{25}H_{24}ClN_5O_3S \cdot 0.5CH_4O$ | C, 58.22; H, 4.98; N, 13.31 | C, 58.18; H, 4.78; N, 13.25 |
| 21i | $C_{26}H_{24}F_3N_5O_3S$ | C, 57.45; H, 4.45; N, 12.88 | C, 57.50; H, 4.47; N, 12.72 |
| 21j | $C_{26}H_{24}F_3N_5O_4S$ | C, 55.81; H, 4.32; N, 12.52 | C, 55.82; H, 4.19; N, 12.41 | which reduces the activity by 50%. These $IC_{50}$ values were calculated from at least three separate runs, each in triplicate, to obtain the statistics herein, e.g., standard deviation.

Example 23

Cyclooxygenase Inhibition Assay

The ability of the test compounds 7, 11a-g, 15, and 21a-j to inhibit ovine COX-1 and human recombinant COX-2 (% inhibition at 100 μM and $IC_{50}$ values (μM), respectively) was determined using an COX Fluorescent Inhibitor Screening Assay Kit (catalog number 700100, Cayman Chemical, Ann Arbor, Mich.) according to the manufacturer's instructions. Stock solutions of test compounds were dissolved in a minimum volume of DMSO. 10 μl of various concentrations of the test compound solutions, e.g., $[I]_{final}$ between 0.01 and 100 μM, were added to a series of supplied reaction buffer solutions (150 μl, 100 mM Tris-HCl, pH 8.0) with either COX-1 or COX-2 (10 μl) enzyme in the presence of Heme (10 μl) and a fluorometric substrate (10 μl). The reactions were initiated by quickly adding 10 μl of arachidonic acid solution and then incubated for two minutes at room temperature. Fluorescence of resorufin, which is produced by the reaction between $PGG_2$ and fluorometric substrate, ADHP (10-acetyl-3,7-dihydroxyphenoxazine), were analyzed with an excitation wavelength of 535 nm and an emission wavelength of 590 nm. The intensity of this fluorescence is proportional to the amount of resorufin, which is proportional to the amount of $PGG_2$ present in the well during the incubation. Percent inhibition was calculated by comparison from the 100% initial activity sample value (no inhibitor). The concentration of the test compound causing 50% inhibition of COX-2 ($IC_{50}$, μM) was calculated from the concentration-inhibition response curve using triplicate determinations.

TABLE 2

Inhibitory Activities of Compounds 7, 11a-h, 15, and 21a-j.

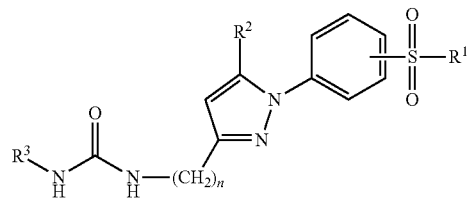

| Entry | $R_1$ | $R_2$ | $R_3$ | n | COX-2[a] $IC_{50}$ (μM)[c] | COX-1[a] (% inhibition)[d] | sEH[b] $IC_{50}$ (nM) |
|---|---|---|---|---|---|---|---|
| Celecoxib | | | | | 0.01 | 40.5 | >10,000 |
| Rofecoxib | | | | | 2 | 16.5 | >10,000 |
| Indomethacin | | | | | <100 | 83.6 | >10,000 |
| t-AUCB | | | | | >100 | 25.2 | 0.5 ± 0.1 |
| 11a | Me | phenyl | 1-adamantyl | 1 | >10 | 12.7 | 25 ± 1 |
| 11b | Me | phenyl | c-heptyl | 1 | >10 | 3.4 | 2.6 ± 0.3 |
| 11c | Me | phenyl | phenyl | 1 | >10 | 9.9 | 47 ± 4 |
| 11d | Me | phenyl | p-$CF_3$O-phenyl | 1 | 7 | 10.4 | 6.0 ± 0.5 |
| 11e | Me | phenyl | p-$CF_3$-phenyl | 1 | >10 | 10.7 | 110 ± 5 |
| 11f | Me | phenyl | m-$CF_3$-phenyl | 1 | 2.5 | 7.8 | 72 ± 8 |
| 11g | $NH_2$ | phenyl | m-$CF_3$-phenyl | 1 | 1 | 16.9 | 84 ± 6 |
| 11h | Me | t-butyl | m-$CF_3$-phenyl | 1 | >10 | 2.4 | 32 ± 3 |
| 7 | $NH_2$ | phenyl | m-$CF_3$-phenyl | 0 | 2 | 33.9 | 88 ± 5 |
| 15 | $NH_2$ | phenyl | m-$CF_3$-phenyl | 2 | 1 | 22.0 | 26 ± 3 |
| 21a | Me | phenyl | m-$CF_3$-phenyl | 3 | 3 | 6.4 | 3.4 ± 0.2 |
| 21b | $NH_2$ | phenyl | m-$CF_3$-Phenyl | 3 | 0.71 | 27.2 | 4.1 ± 0.4 |
| 21c | $NH_2$ | p-tolyl | m-$CF_3$-phenyl | 3 | 2.8 | 12.1 | 10 ± 1 |
| 21d | $NH_2$ | phenyl | 2,6-diMe-phenyl | 3 | >10 | 6.2 | 1550 ± 70 |
| 21e | $NH_2$ | phenyl | phenyl | 3 | >10 | 15.8 | 0.8 ± 0.1 |
| 21f | $NH_2$ | phenyl | 1-adamantyl | 3 | 7 | 6.7 | 0.5 ± 0.1 |
| 21g | $NH_2$ | phenyl | c-heptyl | 3 | 2 | 10.2 | 0.5 ± 0.1 |
| 21h | $NH_2$ | phenyl | p-Cl-phenyl | 3 | 6 | 15.2 | 0.8 ± 0.1 |
| 21i | $NH_2$ | phenyl | p-$CF_3$-phenyl | 3 | 1.26 | 22.7 | 0.9 ± 0.1 |
| 21j | $NH_2$ | phenyl | p-$CF_3$O-phenyl | 3 | 0.92 | 13.8 | 0.5 ± 0.1 |

[a]Values are the means ± SD of three independent experiments with COX Fluorescent Inhibitor Screening Assay Kit (Catalog No. 700100, Cayman Chemicals Inc., Ann Arbor, MI).
[b]Determined via a kinetic fluorescent assay, results are means ± SD of three separate experiments.
[c]Data points are triplicate average. Coefficient variation was observed between 5 and 10%.
[d]% inhibition at 100 μM concentration, such that the $IC_{50}$ for COX-1 is >100 μM for the compounds of the present invention.

Example 24

Pharmacokinetic Protocol in Mice and Rats

Pharmacokinetic Protocol in Mice.

All the animal experiments were performed according to protocols approved by the Animal Use and Care Committee of University of California, Davis. The PK study of Compounds 21b, e-j in a murine model was conducted according to the protocol as previously reported by Liu et al. Male CFW mice (8 week old, 24-30 g) were purchased from Charles River Laboratories. Compounds 21b, e-j (1 mg each) were dissolved in 1 mL of oleic ester-rich triglyceride containing 20% polyethylene glycol (average molecular weight: 400) to give a clear solution for oral administration. Cassette 1 contained compounds 21e, 21b, 21g, and rofecoxib, cassette 2, compounds 21i, 21j, 21f and celecoxib, cassette 3 compounds 21h, and t-AUCB. Each cassette was orally administered to 4 mice at a dose of 5 mg/kg in 120-150 μl of vehicle depending on animal weight. Blood (10 μL) was collected from the tail vein using a pipette tip rinsed with 7.5% EDTA(K3) at 0, 0.5, 1, 1.5, 2, 4, 6, 8, 24 hours after oral administration. The extraction of compounds from blood was performed by following our previous method except that ethyl acetate (200 μL) was added after the addition of internal solution I (10 μL, 500 nM solution of 1-(4-chloro-3-trifluoromethanylphenyl-3-(1-cyclopropanecarboxylpiperidin-4-yl)urea in methanol)) to each thawed blood sample instead of prior to the addition of internal solution I. Blood samples were analyzed using an Agilent 1200 Series HPLC equipped with a 4.6 mm×150 mm Inertsil ODS-4 3 μm column (GL Science Inc., Japan) held at 40° C. and coupled with an Applied Biosystems 4000 QTRAP hybrid, triple-quadrupole mass spectrometer. The instrument was equipped with a linear ion trap and a Turbo V ion source and was operated in negative ion MRM mode. The solvent system consisted of water/acetic acid (999/1 v/v, solvent A) and acetonitrile/acetic acid (999/1 v/v; solvent B). The gradient initially was 30% solvent B and was thereafter linearly increased to 100% solvent B in 5 min. This was maintained for 3 min, then the gradient was returned to 30% solvent B in 2 min. The flow rate was 0.4 mL/min. The injection volume was 10 μL and the samples were kept at 4° C. in the auto sampler. The PK parameters of individual mice were calculated by fitting the time dependent curve of blood inhibitor concentration to a non-compartmental analysis with the WinNonlin software (Pharsight, Mountain View, Calif.). Parameters determined include the time of maximum concentration (Tmax), maximum concentration (Cmax), half-life ($t_{1/2}$), and area under the concentration-time curve to terminal time (AUCt).

TABLE 3

PK Parameters of the Compounds 21b, e-j in Mice (A) by Oral Cassette Dosing at 5 mg/kg (n = 1) and in Rats (B) by Oral Administration at 1 mg/kg (n = 4).

| species | Inhibitors | $T_{max}$ (h) | $C_{max}$ (nM) | AUC (nM*h) | $t_{1/2}$ (h) |
|---|---|---|---|---|---|
| A | 21h | 0.8 | 190 | 375 | 2.4 |
|   | 21i | 0.8 | 260 | 980 | 2.6 |
|   | 21j | 0.8 | 290 | 1335 | 2.4 |
|   | 21e | 0.5 | 100 | 125 | 3.1 |
|   | 21b | 0.5 | 19 | 35 | 1.0 |
|   | 21g | 0.5 | 42 | 100 | 3.5 |
|   | 21f | 0.5 | 20 | 22 | 1.7 |
| B | 21i | 1.5 ± 0.6 | 415 ± 139 | 2764 ± 804 | 12.9 ± 3.8 |
|   | 21j | 1.0 ± 0.7 | 180 ± 71 | 1230 ± 521 | 11.6 ± 5.6 |

Pharmacokinetic Protocol in Rats.

Four male Sprague-Dawley rats (8 week old, 250-300 g) were used for pharmacokinetic study for dual inhibitors. Compounds 21i and 21j were given by oral administration at the dose of 1 mg/kg. Inhibitors were dissolved in oleic oil containing 10% polyethylene glycol 400 to form a clear solution. Blood (10 μL) was collected from the tail vein by using a pipette tip rinsed with 7.5% EDTA($K_3$) at 0, 0.5, 1, 1.5, 2, 4, 6, 8, and 24 hour after oral dosing with the inhibitor. Each blood sample was immediately transferred to a tube containing 50 μL of water and mixed by Vortex for 1 min, all samples were stored at −80° C. until analysis. Blood sample preparation and drug level quantification by LC/MS/MS were the same as previous study. The pharmacokinetic parameters of individual rat were calculated by fitting the data from blood concentration–time dependent curve to a non-compartmental analysis with the WinNonlin software (Pharsight, Mountain View, Calif.). Maximum concentration ($C_{max}$), Time of maximum concentration ($T_{max}$), half life ($t_{1/2}$), and area under the concentration-time curve to terminal time (AUC) were analyzed to characterize the pharmacokinetic profile of Compounds 21i and 21j.

Example 25

Von Frey Mechanical Nociceptive Assay

Rats weighing approximately 250-300 grams are brought to the testing apparatus and allowed to acclimate for 30 minutes. After 30 minutes the rats are tested with a von Frey aesthesiometer for their non-treated baseline withdrawal latency to mechanical stimulation. The von Frey apparatus is a raised metal mesh platform that has clear acrylic chambers to enclose rats but allow them to move freely. A rigid tip von Frey probe is used to probe the plantar surface of the rat hind paw though the mesh floor to elicit a withdrawal response. The measures recorded are grams of force applied to the hind paw required to elicit a withdrawal. The pretreatment baseline score is considered the pain-free baseline (BL) and is assigned 100% for further response calculations. For the pain assay one of three compounds sEHI, Celebrex, or compound 21i formulated in 100% PEG400 is injected subcutaneously 60 minutes prior to the intraplantar LPS injection. The rats are then tested at 15, 30, 60, 120, 180, 240, 300, and 360 minutes post LPS with the von Frey aesthesiometer for their withdrawal latency. Reported scores are an average of 6 male SD rats with SEM for the group. The measures are then calculated as a percent of the pretreatment baseline score.

Example 26

Angiogenesis Assay

Human umbilical vein endothelial cells (HUVEC, Clonetics®, Lonza) were cultured in EGM-2 basal medium with supplements (BulletKit, Lonza) according to the manufacturer's instructions. All experiments with HUVEC were conducted with cells from passage 2 to 5.
Cell Proliferation Assay
Cells (HUVEC, H-1, PC-3, A375, Met-1) were seeded into 96-well plates at $1.0$-$1.5 \times 10^3$ cells per well in 100 μL complete medium. After 24 h, the medium was replaced with fresh complete medium containing test compounds and the cells were incubated for another 72 hours. Cell viability was assessed by MTT assay (Sigma-Aldrich).
Tube Formation Assay
Endothelial tube formation assay was carried out using a slightly modified method described by Arnaoutova and Kleinman (*Nat. Protocols* 5, 628-635). Briefly, 96-well plates were coated with growth-factor reduced Matrigel (50 μL per well, BD Biosciences, San Jose, Calif.) at 37° C. for 30 min. HUVEC cells were seeded into the 96-well plates at $2 \times 10^4$ cells per well in 100 μL serum-free F-12K medium with or without test compounds and incubated for 6 h 37° C. in the incubator. Microscope image was recorded and analyzed by NIH Image J software.
Aorta Ring Assay
Mouse aorta ring assay was carried out using a slightly modified method described by Bellacen and Lewis (*J Vis Exp*, e1564). The 48-well plates were coated with 50 μL per well growth-factor reduced Matrigel at 37° C. for 30 min. The aorta of C57BL/6 mice was harvested, washed with cold serum-free F-12K medium 5-6 times, and cut to ~1 mm length pieces. The aorta ring was put in the center area of Matrigel-coated 48-well plates, then another 100 μL Matrigel was added into each well and incubated at 37° C. for another 30 min. Complete endothelial EGM-2 culture medium (500 μL per well) with or without test compounds was added into each well, incubated in 37° C. incubators for 6-12 days, microscope image was recorded and analyzed by NIH Image J software.

Matrix Metalloproteinase (MMP) Assay

MMP activity in PC-3 and HUVEC cells were carried out by zymography (*J Vis Exp*, e2445). Briefly, PC-3 cells or HUVEC cells in 6-well plates were treated with 21i in complete cell culture medium for 1-3 days. The medium was collected, centrifuged, and equal amount of protein was loaded onto 10% Novex® 10% Gelatin Zymogram gels (Invitrogen) for SDS-PAGE. After that, the gels were incubated at renaturing buffer for 30 min, followed with incubation at zymography developing buffer for 30 min at room temperature, and replaced with fresh developing buffer and incubated at 37° C. overnight. The gels were stained by Coomassie blue, and images were recorded and analyzed by NIH Image J software.

In Vivo Angiogenesis Assay

In vivo angiogenesis assay was carried out using Matrigel plug assay as described by Adini et al. (*J Immunol Methods* 342, 78-81). All procedures and animal care were performed in accordance with the protocols approved by the Institutional Animal Care and Use Committee of the University of California-Davis. Male C57BL/6 mice were purchased from Charles River Lab. After acclimation for 1 wk in a standard animal facility, the animals were lightly anesthesized using 1-4% isoflurane in oxygen (2 L/min) and placed on a heated stage to maintain body temperature at 37° C. Growth-factor reduced Matrigel (0.5 mL, BD Biosciences, San Jose, Calif.) mixed with 100 ng mouse VEGF 164 (R&D Systems, Minneapolis, Minn.), 20 U heparin (APP Pharmaceuticals, Schaumburg, Ill.), with or without test compounds were subcutaneously injected into the mice at the abdominal area. Each mouse was injected with two gels (with/without test compounds) symmetrically in the abdomen. After 4-7 days, the animals were euthanized and dissected to recover the implanted Matrigel plugs. Hemoglobin contents inside the Matrigel implants were analyzed by Drabkin's reagent (Sigma-Aldrich, St. Louis, Mont.).

In Vivo Met-1 Tumor Growth and Ultrasound Imaging

Cells derived from highly metastatic breast cancer Met-1 will be transplanted into the fat pads of FVB female mice. Once tumor size each approximately 3-5 mm, dual inhibitor 21i dissolved in a mixed solution of DMSO-H$_2$O will be administered by Alzet® micro-osmotic pump for 2 weeks (dose=0.1 mg/kg/day). Over this period, animals will be checked 3 times per week with ultrasound to mark changes in tumor growth and size. Ultrasound contrast agent microbubbles will also be administered during each ultrasound session by IV injection to track changes in tumor vasculature (*Invest Radiol* 46, 215-224).

Example 27

Cell Viability Analysis

Cells were plated at 10,000 cell per well in 96-well plates and allowed to attach overnight under the growth conditions described above. On the following day, celecoxib and the COX-2/sEH dual inhibitors were added to each well and incubated for the length of time as indicated. These compounds were dissolved in 100% DMSO and diluted with EMEM to the desired concentration of 0.1 μM, 1.0 μM, 10 μM, 25 μM, and 50 μM, with a final DMSO concentration of 0.1% for all cell-based in vitro studies. All studies included DMSO as a solvent control. Cell viability was determined using the MTT Cell Viability Assay Kit from ATCC according to manufacturer's instructions. The 96-well plates were measure at 570 nm using SpectroMax 190 plate reader (Molecular Devices, Sunnyvale, Calif.). The EC$_{50}$ values at which 50% of the cell viability as compared to the DMSO control were calculated using nonlinear regression analysis with the KaleidaGraph graphing program (Synergy Software). Each concentration was performed in triplicate per 96-well plate and EC$_{50}$ data are presented as the mean±standard deviation from at least 3 separate experiments performed on separate days.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A compound of Formula I:

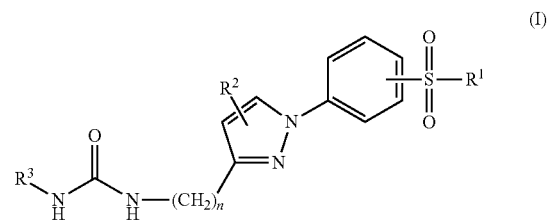

wherein
R$^1$ is selected from the group consisting of C$_{1-6}$ alkyl, —NR$^{1a}$R$^{1b}$ and cycloalkyl;
R$^{1a}$ and R$^{1b}$ are each independently selected from the group consisting of H and C$_{1-6}$ alkyl;
R$^2$ is selected from the group consisting of C$_{1-6}$ alkyl, cycloalkyl and aryl, wherein the cycloalkyl and aryl are each optionally substituted with C$_{1-6}$ alkyl;
R$^3$ is selected from the group consisting of cycloalkyl and aryl, each optionally substituted with from 1 to 3 R$^{3a}$ groups wherein each R$^{3a}$ is independently selected from the group consisting of C$_{1-6}$ alkyl, C$_{1-6}$ alkoxy, halogen, C$_{1-6}$ haloalkyl and C$_{1-6}$ haloalkoxy;
subscript n is an integer from 0 to 6;
and salts and optical isomers thereof.

2. The compound of claim 1, having the formula Ia:

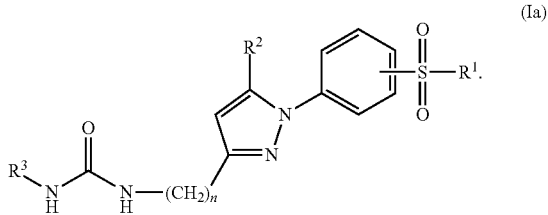

3. The compound of claim 1, having the formula Ib:

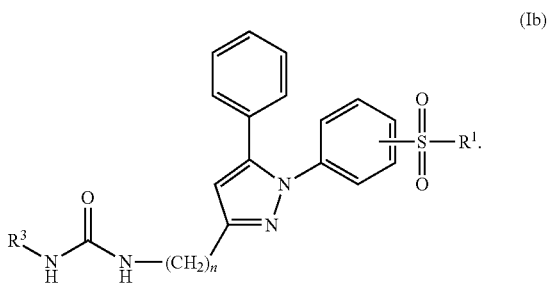

4. The compound of claim 1, having the formula Ic:

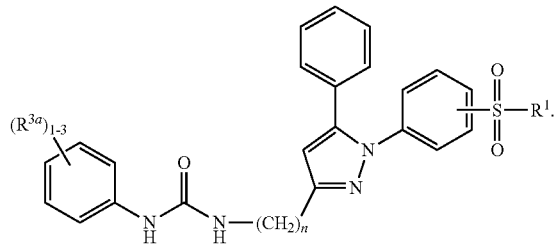
(Ic)

5. The compound of claim 1, wherein
   $R^1$ is selected from the group consisting of $C_{1-6}$ alkyl and —$NR^{1a}R^{1b}$;
   $R^{1a}$ and $R^{1b}$ are each independently selected from the group consisting of H and $C_{1-6}$ alkyl;
   $R^2$ is aryl, optionally substituted with $C_{1-6}$ alkyl; and
   $R^3$ is selected from the group consisting of cycloalkyl and aryl, each optionally substituted with from 1 to 3 $R^{3a}$ groups wherein each $R^{3a}$ is independently selected from the group consisting of $C_{1-6}$ alkyl, halogen, $C_{1-6}$ haloalkyl and $C_{1-6}$ haloalkoxy.

6. The compound of claim 1, wherein
   $R^1$ is selected from the group consisting of methyl, ethyl, propyl, —$NH_2$ and —$NMe_2$;
   $R^2$ is phenyl, optionally substituted with a member selected from the group consisting of methyl, ethyl and propyl; and
   $R^3$ is selected from the group consisting of cyclohexyl, cycloheptyl, cyclooctyl, adamantyl and phenyl, wherein the phenyl is optionally substituted with from 1 to 3 $R^{3a}$ groups wherein each $R^{3a}$ is independently selected from the group consisting of methyl, ethyl, propyl, Cl, Br, I, —$CF_3$ and —$OCF_3$.

7. The compound of claim 1, wherein the compound is selected from the group consisting of:

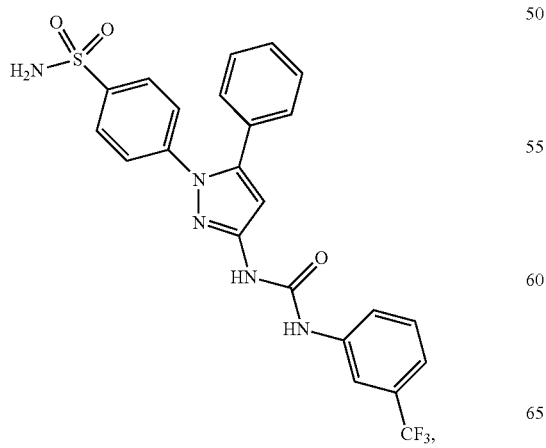

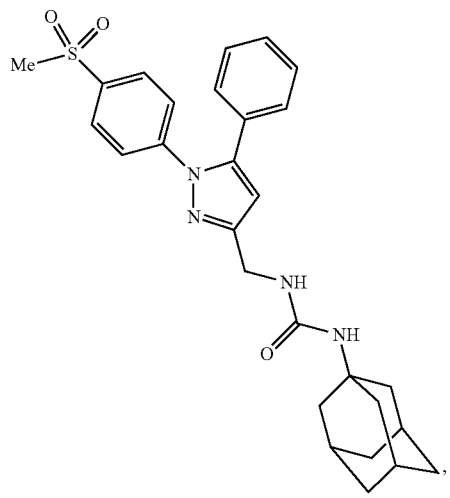

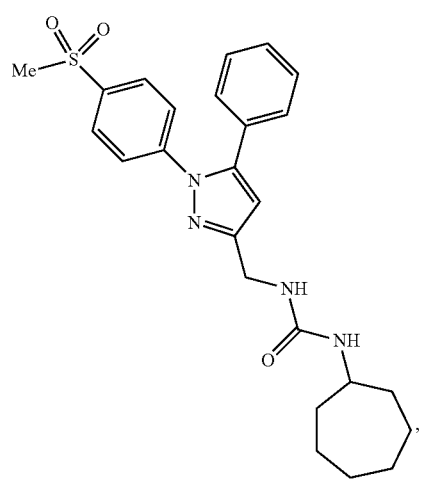

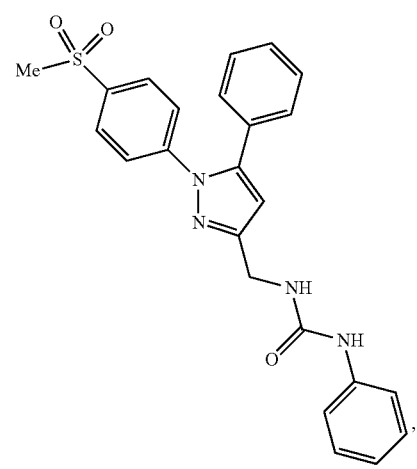

67
-continued
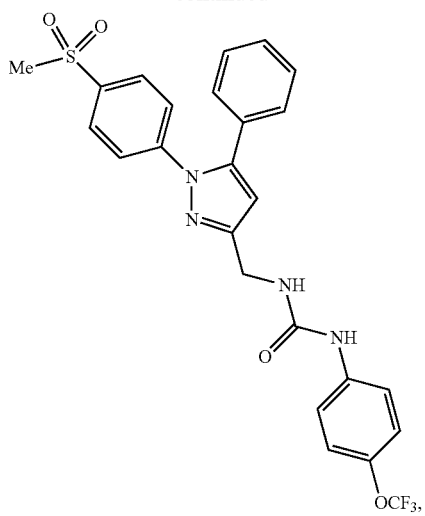
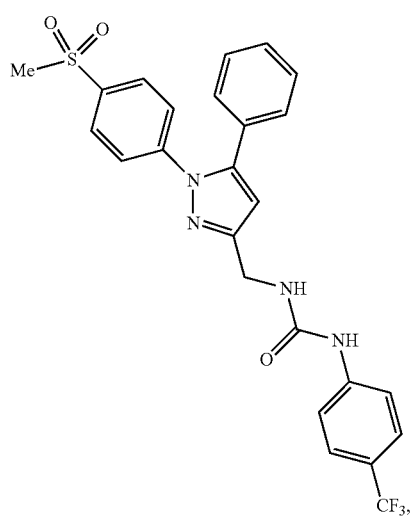
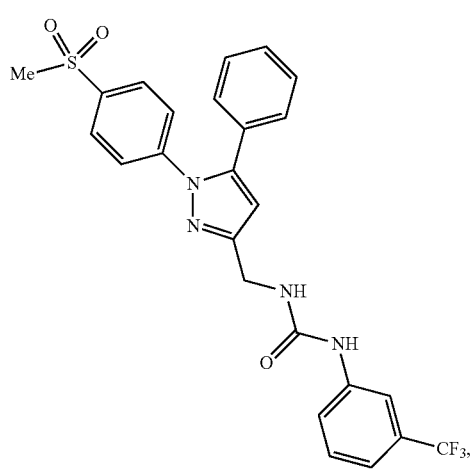
68
-continued
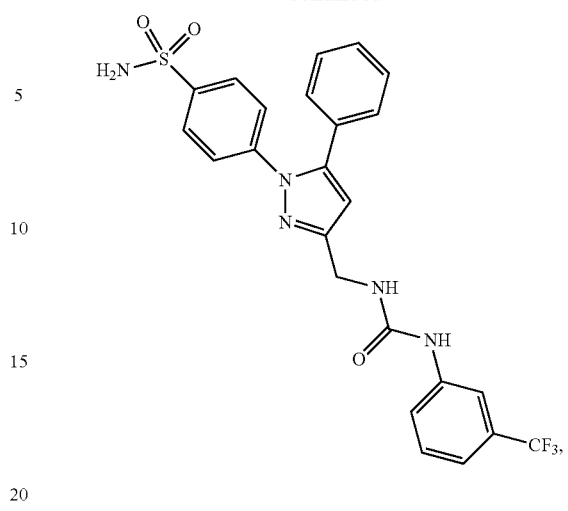
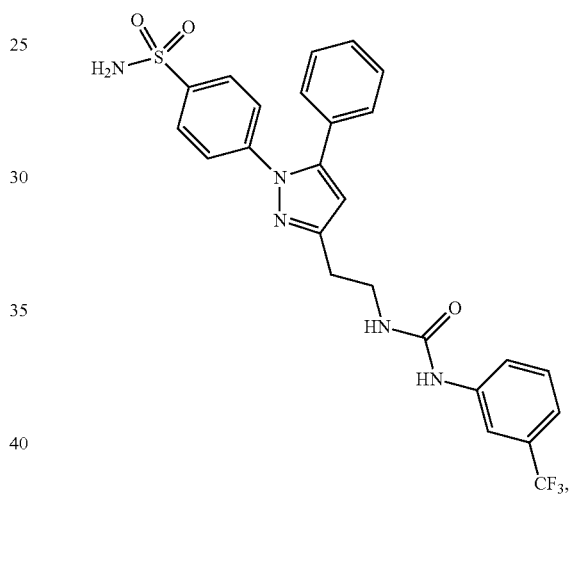
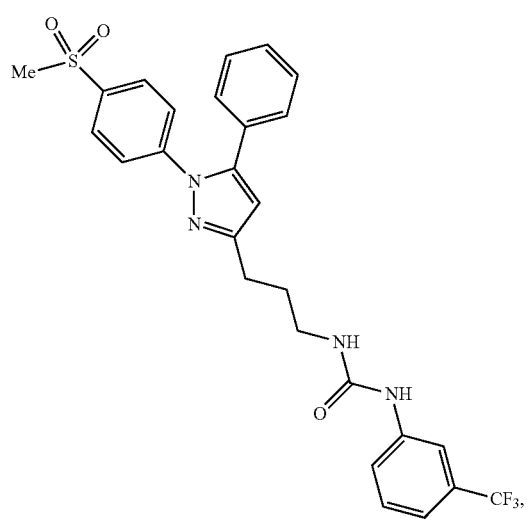

69
-continued
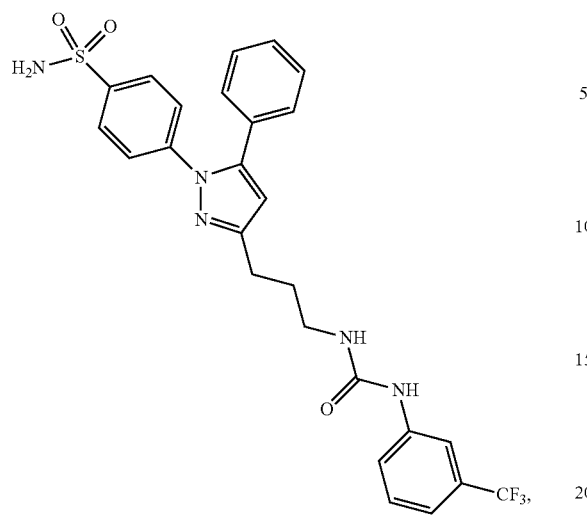
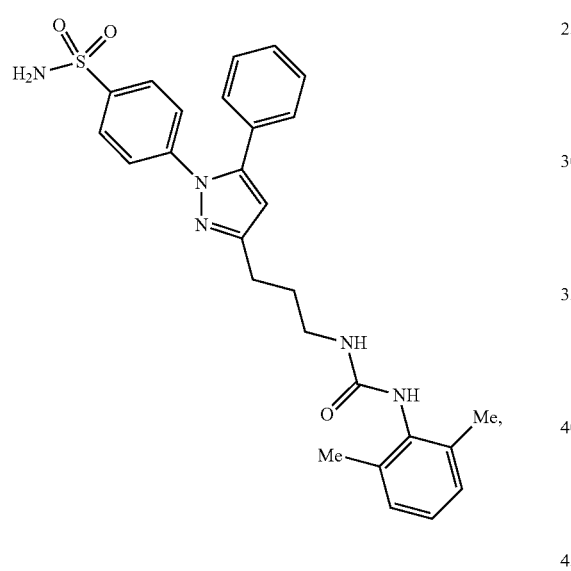
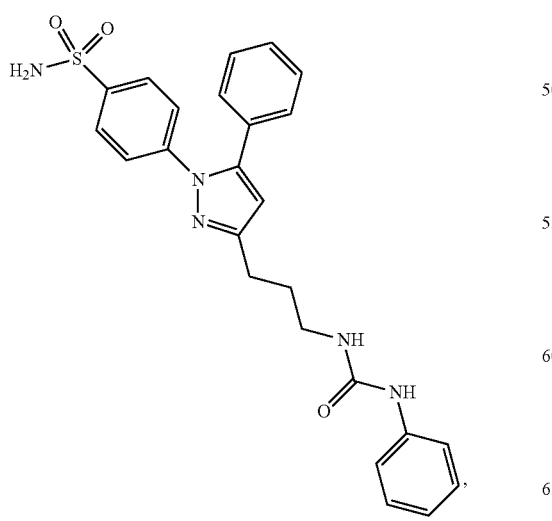
70
-continued
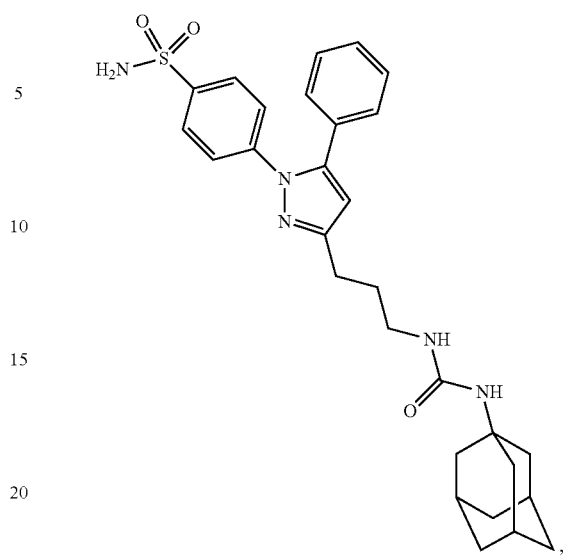
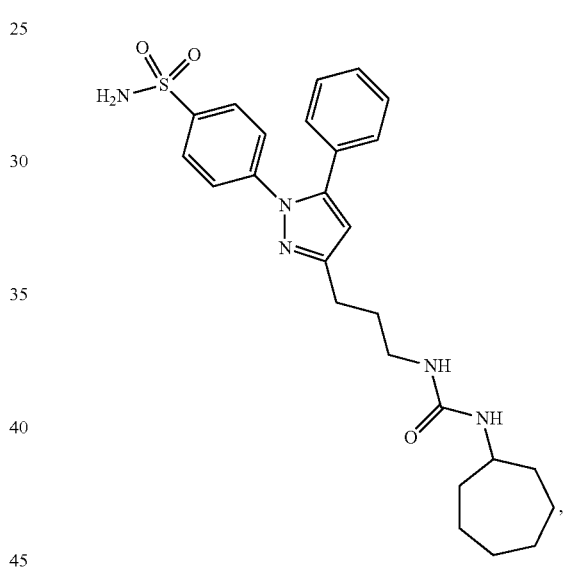
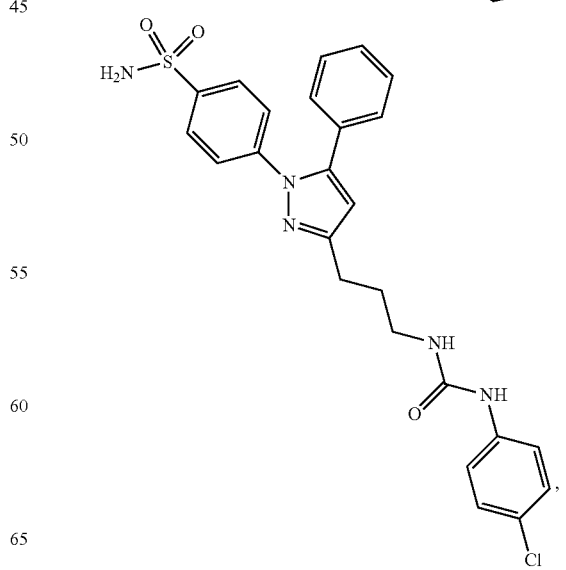

-continued

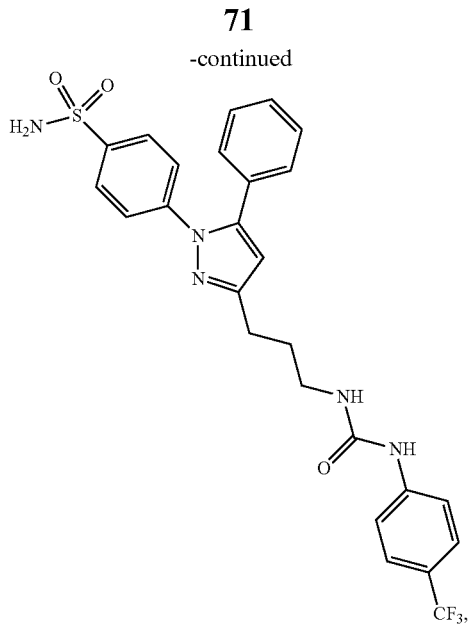

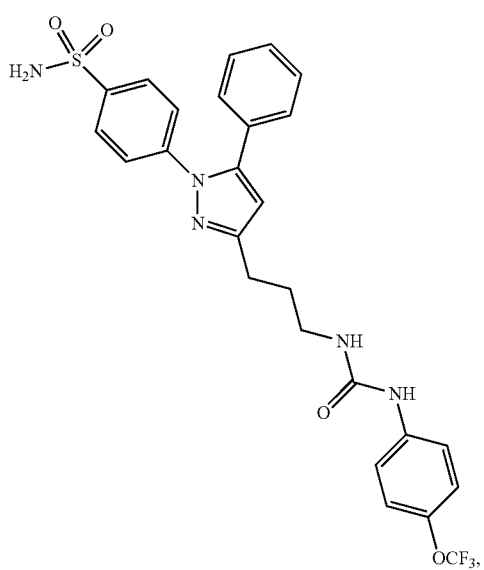

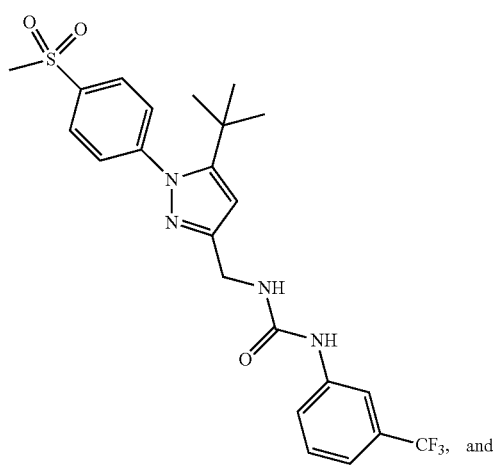

-continued

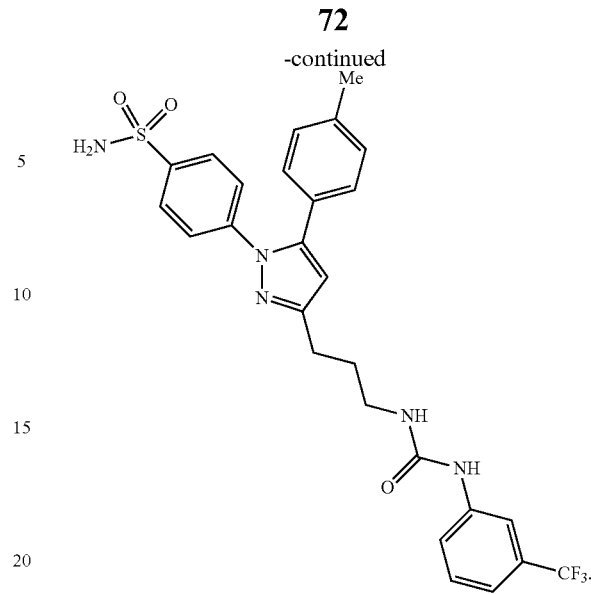

8. The compound of claim 1, wherein the compound is

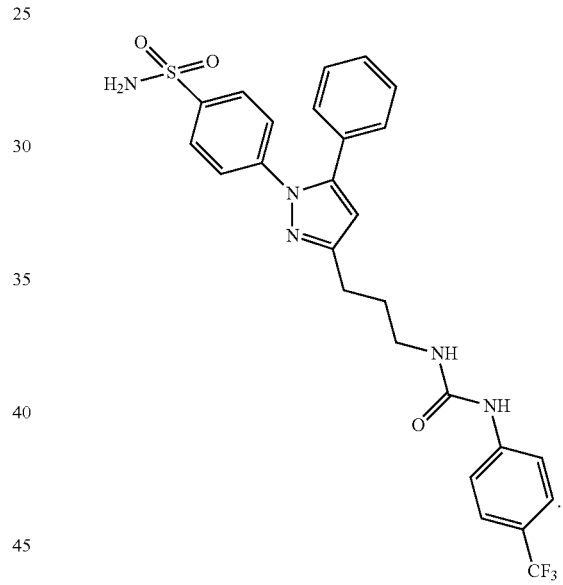

9. A pharmaceutical composition comprising a compound of claim 1 and a pharmaceutically acceptable excipient.

10. A method of inhibiting a soluble epoxide hydrolase (sEH), the method comprising contacting the sEH with a compound of claim 1 in an amount sufficient to inhibit the sEH, thereby inhibiting the sEH.

11. The method of claim 10, wherein the compound further inhibits an enzyme.

12. The method of claim 11, wherein the enzyme is a cyclooxygenase enzyme selected from the group consisting of cyclooxygenase-1 (COX-1) and cyclooxygenase-2 (COX-2).

13. The method of claim 10, wherein the sEH is inhibited without substantially inhibiting a cyclooxygenase enzyme selected from the group consisting of cyclooxygenase-1 (COX-1) and cyclooxygenase-2 (COX-2).

14. A method of inhibiting a cyclooxygenase enzyme selected from the group consisting of cyclooxygenase-1 (COX-1) and cyclooxygenase-2 (COX-2), the method comprising contacting the cyclooxygenase enzyme with a compound of claim 1 in an amount sufficient to inhibit the cyclooxygenase enzyme, thereby inhibiting the cyclooxygenase enzyme.

15. The method of claim 14, wherein the cyclooxygenase enzyme is COX-2.

16. The method of claim 15, wherein the COX-2 is inhibited without substantially inhibiting COX-1.

17. A method for monitoring the activity of a soluble epoxide hydrolase, the method comprising contacting the soluble epoxide hydrolase with an amount of a compound of claim 1 sufficient to produce a detectable change in the fluorescence of the soluble epoxide hydrolase by interacting with one or more tryptophan residues present in the catalytic site of said soluble epoxide hydrolase, thereby monitoring the activity of the soluble epoxide hydrolase.

18. A method of ameliorating the symptoms of breast and liver cancer, the method comprising administering to a subject in need thereof, a therapeutically effective amount of a compound of claim 1, thereby ameliorating the symptoms of breast and liver cancer.

19. A method of ameliorating the symptoms of breast and liver cancer, the method comprising contacting breast or liver cancer cells with a therapeutically effective amount of a compound of claim 1, thereby ameliorating the symptoms of breast and liver cancer.

20. The method of claim 19, wherein the contacting is performed in vitro.

21. A method of inhibiting cell proliferation, comprising contacting a cell with an effective amount of a compound of claim 1, thereby inhibiting cell proliferation.

22. The method of claim 21, wherein the cell is a human umbilical vein endothelial cell (HUVEC).

23. A method of reducing or inhibiting angiogenesis in a tissue, comprising contacting the tissue with an effective amount of a compound of claim 1, thereby reducing or inhibiting angiogenesis in the tissue.

* * * * *

UNITED STATES PATENT AND TRADEMARK OFFICE
CERTIFICATE OF CORRECTION

PATENT NO. : 9,096,532 B2
APPLICATION NO. : 13/993317
DATED : August 4, 2015
INVENTOR(S) : Bruce D. Hammock et al.

Page 1 of 1

It is certified that error appears in the above-identified patent and that said Letters Patent is hereby corrected as shown below:

In the second paragraph of the specification, column 1, lines 11-12, please insert --"This invention was made with Government support under Grant Nos. ES002710 and ES004699 awarded by the National Institutes of Health. The Government has certain rights in this invention."--

Signed and Sealed this
Twenty-second Day of March, 2016

Michelle K. Lee
*Director of the United States Patent and Trademark Office*